(12) United States Patent
Yabuta et al.

(10) Patent No.: US 7,807,421 B2
(45) Date of Patent: Oct. 5, 2010

(54) PROCESS FOR PRODUCTION OF BIOPTERIN COMPOUND

(75) Inventors: Masayuki Yabuta, Tatebayashi (JP); Kazuaki Furukawa, Tatebayashi (JP); Nobue Miyamoto, Higashimatsuyama (JP); Katsuhiko Yamamoto, Tatebayashi (JP); Kazuhiro Ohsuye, Ota (JP)

(73) Assignee: Asubio Pharma Co., Ltd., Tokyo (JP)

( * ) Notice: Subject to any disclaimer, the term of this patent is extended or adjusted under 35 U.S.C. 154(b) by 312 days.

(21) Appl. No.: 11/194,564

(22) Filed: Aug. 2, 2005

(65) Prior Publication Data

US 2006/0008869 A1    Jan. 12, 2006

Related U.S. Application Data

(63) Continuation of application No. 10/362,914, filed as application No. PCT/JP01/07395 on Aug. 28, 2001, now abandoned.

(30) Foreign Application Priority Data

Aug. 31, 2000    (JP)    .............................. 2000-262973

(51) Int. Cl.
| | |
|---|---|
| C12P 17/16 | (2006.01) |
| C12N 1/19 | (2006.01) |
| C12N 1/21 | (2006.01) |
| C12N 5/10 | (2006.01) |
| C12N 15/00 | (2006.01) |
| C12N 9/04 | (2006.01) |
| C12N 9/88 | (2006.01) |
| C12N 9/78 | (2006.01) |
| C12P 21/00 | (2006.01) |
| C12Q 1/34 | (2006.01) |
| C07K 14/00 | (2006.01) |
| C07H 21/00 | (2006.01) |

(52) U.S. Cl. ............... 435/118; 435/252.3; 435/252.31; 435/254.21; 435/252.33; 435/227; 435/232; 435/190; 435/18; 435/25; 435/320.1; 435/325; 530/350; 536/23.2

(58) Field of Classification Search ................. 435/227, 435/232, 190, 18, 25, 320.1, 252.3, 325, 435/252.31, 254.11, 254.21; 536/23.2; 530/350
See application file for complete search history.

(56) References Cited

FOREIGN PATENT DOCUMENTS

| | | |
|---|---|---|
| EP | 153696 | 9/1985 |
| EP | 318926 | 6/1989 |
| JP | 61-9296 | 1/1986 |
| JP | 61-52296 | 3/1986 |
| JP | 1-221380 | 9/1989 |
| JP | 4-82888 | 3/1992 |
| JP | 5-33990 | 5/1993 |
| KP | 2002-0096181 | 12/2002 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Woo et al., Appl. Environ. Microbiol. 68(6):3138-3140, Jun. 2002.*
Laufs et al., Journal of Neurochemistry 71(1):33-40, 1998.*
Yamamoto et al., Metabolic Engineering 5:246-254, 2003.*
Kim et al., Molecules and Cells 10(4):405-410, Aug. 31, 2000.*
Weisberg et al., "Purification and Characterization of GTP Cyclohydrolase I from *Drosophila melanogaster*\*", *The Journal of Biological Chemistry*, vol. 261, No. 3, pp. 1453-1458 (1986).
Iino et al., "Discovery of a new tetrahydrobiopterin-synthesizing enzyme in the *lemon* mutant of the silkworm *Bombyx mori*" *Biochimica et Biophysica Acta*, vol. 1297, pp. 191-199 (1996).
Maier et al., "Biosynthesis of Pteridines in *Neurospora crassa, Phycomyces blakesleeanus* and *Euglena gracilis*:: Detection and Characterization of Biosynthetic Enzymes*", *Photochemistry and Photobiology*, vol. 61, No. 1, pp. 43-53.
Son et al., "Cyclic Guanosine -3',5'-Monophosphate and Biopteridine Biosynthesis in *Nocardia* sp.", *Journal of Bacteriology*, vol. 182, No. 13, pp. 3644-3648 (2000).
Wede et al., "Neopterin Derivatives Modulate Toxicity of Reactive Species on *Escherichia coli*", *Free Radic. Res.*, vol. 31, No. 5, pp. 381-388 (1999).
Ishi et al., "Improved Inosine Production and Derepression of Purine Nucleotide Biosynthetic Enzymes in 8-Azaguanine Resistant Mutants of *Bacillus subtilis*", *Agr. Biol. Chem.*, vol. 36, No. 9, pp. 1511-1522 (1972).
Matsui et al., "Production of Guanosine by Psicofuranine and Decoyinine Resistant Mutants of *Bacillus subtilis*" *Agr. Biol. Chem.*, vol. 43, No. 8, pp. 1739-1744 (1979).
Tiedeman et al., "Nucleotide Sequence of the *gua* A Gene Encoding GMP Synthetase of *Escherichia coil* K12*", *The Journal of Biological Chemistry*, vol. 260, No. 15, pp. 8676-8679 (1985).
Stragier et al., "Processing of a Sporulation Sigma Factor in *Bacillus subtilis*: How Morphological Structure Could Control Gene Expression", *Cell*, vol. 52, pp. 697-704 (1988).
Takikawa et al., "Biosynthesis of Tetrahydrobiopterin" *Eur. J. Biochem*, vol. 161, pp. 295-302 (1986).
Katzenmeier et al., "Biosynthesis of Tetrahydrofolate", *Biol. Chem. Hoppe-Seyler*, vol. 372, pp. 991-997 (1991).
Inoue et al., "Purification and cDNA Cloning of Rat 6-Pyruvoyl-tetrahydropterin Synthase*", *The Journal of Biological Chemistry*, vol. 266, No. 31, pp. 20791-20796 (1991).
Yanisch-Perron et al., "Improved M13 phage cloning vectors and host strains: nucleotide sequences of the M13mp18 and pUC19 vectors" *Gene*, vol. 33, pp. 103-119 (1985).
Citron et al., "Isolation and expression of rat liver sepiapterin reductase cDNA", *Proc. Natl. Acad. Sci. USA*, vol. 87, pp. 6436-6440 (1990).

(Continued)

*Primary Examiner*—Delia M Ramirez
(74) *Attorney, Agent, or Firm*—Wenderoth, Lind & Ponack, L.L.P.

(57) ABSTRACT

The present invention provides a transformed cell which is transformed by at least one gene of enzymes participating in biosynthesis of tetrahydrobiopterin and a process for the production of a biopterin compound using the same. In accordance with the present invention, the biopterin compound can be produced in large quantities in an industrial advantageous manner from less expensive materials.

16 Claims, 33 Drawing Sheets

OTHER PUBLICATIONS

Tettelin et al., "The nucleotide sequence of *Saccharomyces cerevisiae* chromosome VII",*Nature*, vol. 387, pp. 81-84 (1997).

Miller, "Nitrosoguanidine Mutagenesis", *Experiments in Molecular Genetics*, Experiment 14, Cold Spring Harbor Laboratory, Cold Spring Harbor, New York, pp. 125-129 (1972).

N. Schramek et al., "Functional expression of murine phenylalanine hydroxylase in *Escherichia coli*", *Corresponding Chemical Abstract: Proceedings of the International Symposium on Pteridines and Folates*, 11th Berchtesgaden, Germany, Jun. 15-20, pp. 527-530, (1997) CAN 128:304545 AN 1998:224650.

Broun et al., *Science*, vol. 282, pp. 1315-1317 (1998).

Van de Loo et al., *Proc. Natl. Acad. Sci.*, vol. 92, pp. 6743-6747 (1995).

Seffernick et al., *J. Bacteriol.*, vol. 183, No. 8, pp. 2405-2410 (2001).

Witkowski et al., *Biochemistry*, vol. 38, pp. 11643-11650 (1999).

Y. Miwa et al., "Possible function and some properties of the CcpA protein of *Bacillus subtilis*", *Microbiology*, vol. 140, pp. 2567-2575 (1994).

Laufs et al., *Journal of Neurochemistry*, vol. 71, No. 1, pp. 33-40 (1998).

Watanabe et al. *Seikagaku*, vol. 53, No. 8, p. 1008 (1981), with English translation.

Oettl et al., "Formation of Oxygen Radicals in solutions of 7,8-Dihydroneopterin", *Biochemical and Biophysical Research Communications*, vol. 264, pp. 262-267 (1999).

Tiedeman et al., "Nucleotide Sequence of the *gua* B locus Encoding IMP dehydrogenase of *Escherichia coli* K12*", *Nucleic Acid Research*, vol. 13, No. 4, pp. 1303-1316 (1985).

Gollinick et al., "The *mtr* locus is a two-gene operon required for transcription attenuation in the *trp* operon of *Bacillus subtilis*", *PNAS USA*, vol. 87, pp. 8726-8730 (1990).

B. Thöny et al., "Tetrahydrobiopterin biosynthesis, regeneration and functions", *Biochem. J.*, vol. 347, pp. 1-16, 2000.

* cited by examiner

A pathway for oxidation and decomposition of tetrahydrobiopterin(THBP)

Fig.8
Preparation of pYES2-PTPS and pYES2-SPR
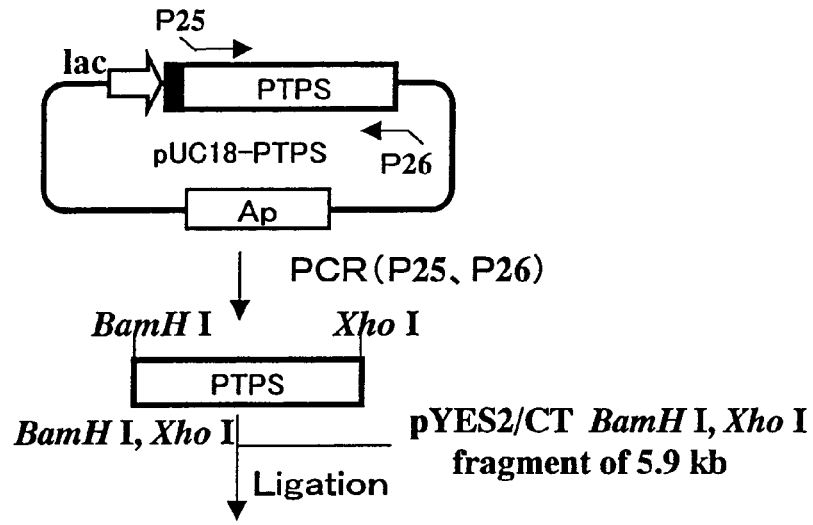
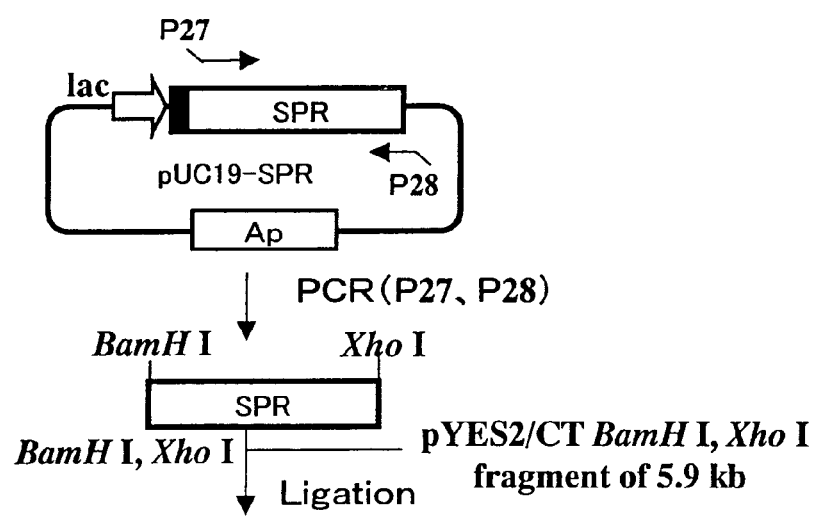
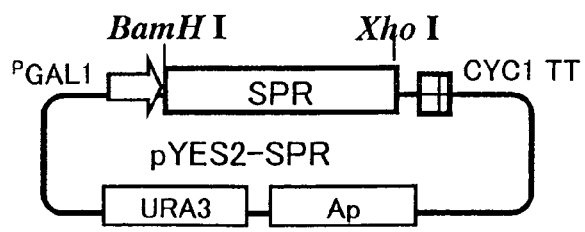

Fig. 10

<u>atgaccatgattacgaattcc</u>atgccaatgccatcactcagtaaagaagcggccctggtt 60
<u>M  T  M  I  T  N  S</u>  M  P  M  P  S  L  S  K  E  A  A  L  V
catgaagcgttagttgcgcgaggactggaaacaccgctgcgcccgcccgtgcatgaaatg 120
 H  E  A  L  V  A  R  G  L  E  T  P  L  R  P  P  V  H  E  M
gataacgaaacgcgcaaaagccttattgctggtcatatgaccgaaatcatgcagctgctg 180
 D  N  E  T  R  K  S  L  I  A  G  H  M  T  E  I  M  Q  L  L
aatctcgacctggctgatgacagtttgatggaaacgccgcatcgcatcgctaaaatgtat 240
 N  L  D  L  A  D  D  S  L  M  E  T  P  H  R  I  A  K  M  Y
gtcgatgaaattttctccggtctggattacgccaatttcccgaaaatcaccctcattgaa 300
 V  D  E  I  F  S  G  L  D  Y  A  N  F  P  K  I  T  L  I  E
aacaaaatgaaggtcgatgaaatggtcaccgtgcgcgatatcactctgaccagcacctgt 360
 N  K  M  K  V  D  E  M  V  T  V  R  D  I  T  L  T  S  T  C
gaacaccattttgttaccatcgatggcaaagcgacggtggcctatatcccgaaagattcg 420
 E  H  H  F  V  T  I  D  G  K  A  T  V  A  Y  I  P  K  D  S
gtgatcggtctgtcaaaaattaaccgcattgtgcagttctttgcccagcgtccgcaggtg 480
 V  I  G  L  S  K  I  N  R  I  V  Q  F  F  A  Q  R  P  Q  V
caggaacgtctgacgcagcaaattcttattgcgctacaaacgctgctgggcaccaataac 540
 Q  E  R  L  T  Q  Q  I  L  I  A  L  Q  T  L  L  G  T  N  N
gtggctgtctcgatcgacgcggtgcattactgcgtgaaggcgcgtggcatccgcgatgca 600
 V  A  V  S  I  D  A  V  H  Y  C  V  K  A  R  G  I  R  D  A
accagtgccacgacaacgacctctcttggtggattgttcaaatccagtcagaatacgcgc 660
 T  S  A  T  T  T  T  S  L  G  G  L  F  K  S  S  Q  N  T  R
cacgagtttctgcgcgctgtgcgtcatcacaactga
 H  E  F  L  R  A  V  R  H  H  N  -

Fig. 11

<u>atgaccatgattacgaattcc</u>atgaacatgaacgcggcggttggccttcggcgccgcgcg 60
<u>M  T  M  I  T  N  S</u>  M  N  M  N  A  A  V  G  L  R  R  R  A
cgattgtcgcgcctcgtgtccttcagcgcgagccaccggctgcacagcccatctctgagt 120
 R  L  S  R  L  V  S  F  S  A  S  H  R  L  H  S  P  S  L  S
gctgaggagaacttgaaagtgtttgggaaatgcaacaatccgaatggccatgggcacaac 180
 A  E  E  N  L  K  V  F  G  K  C  N  N  P  N  G  H  G  H  N
tataaagttgtggtgacaattcatggagagatcgatccggttacaggaatggttatgaat 240
 Y  K  V  V  V  T  I  H  G  E  I  D  P  V  T  G  M  V  M  N
ttgactgacctcaaagaatacatggaggaggccattatgaagccccttgatcacaagaac 300
 L  T  D  L  K  E  Y  M  E  E  A  I  M  K  P  L  D  H  K  N
ctggatctggatgtgccatactttgcagatgttgtaagcacgacagaaaatgtagctgtc 360
 L  D  L  D  V  P  Y  F  A  D  V  V  S  T  T  E  N  V  A  V
tatatctgggagaacctgcagagacttcttccagtgggagctctctataaagtaaaagtg 420
 Y  I  W  E  N  L  Q  R  L  L  P  V  G  A  L  Y  K  V  K  V
tatgaaactgacaacaacattgtggtctacaaaggagaatag
 Y  E  T  D  N  N  I  V  V  Y  K  G  E  -

Fig. 12

```
atgaccatgattacgccaagcttgggcaggggcaggctaggttgcgctgtctgcgtgctg  60
 M  T  M  I  T  P  S  L  G  R  G  R  L  G  C  A  V  C  V  L
accggggcttccggggcttcggccgcgccctggccccgcagctggccgggttgctgtcg  120
 T  G  A  S  R  G  F  G  R  A  L  A  P  Q  L  A  G  L  L  S
cccggttcggtgttgcttctaagcgcacgcagtgactcgatgctgcggcaactgaaggag  180
 P  G  S  V  L  L  S  A  R  S  D  S  M  L  R  Q  L  K  E
gagctctgtacgcagcagccgggcctgcaagtggtgctggcagccgccgatttgggcacc  240
 E  L  C  T  Q  Q  P  G  L  Q  V  V  L  A  A  A  D  L  G  T
gagtccggcgtgcaacagttgctgagcgcggtgcgcgagctccctaggcccgagaggctg  300
 E  S  G  V  Q  Q  L  L  S  A  V  R  E  L  P  R  P  E  R  L
cagcgcctcctgctcatcaacaatgcaggcactcttggggatgtttccaaaggcttcctg  360
 Q  R  L  L  L  I  N  N  A  G  T  L  G  D  V  S  K  G  F  L
aacatcaatgacctagctgaggtgaacaactactgggccctgaacctaacctccatgctc  420
 N  I  N  D  L  A  E  V  N  N  Y  W  A  L  N  L  T  S  M  L
tgcttgaccaccggcaccttgaatgccttctccaatagccctggcctgagcaagactgta  480
 C  L  T  T  G  T  L  N  A  F  S  N  S  P  G  L  S  K  T  V
gttaacatctcatctctgtgtgccctgcagcctttcaagggctggggactctactgtgca  540
 V  N  I  S  S  L  C  A  L  Q  P  F  K  G  W  G  L  Y  C  A
gggaaggctgcccgagacatgttataccaggtcctggctgttgaggaacccagtgtgagg  600
 G  K  A  A  R  D  M  L  Y  Q  V  L  A  V  E  E  P  S  V  R
gtgctgagctatgccccaggtcccctggacaccaacatgcagcagttggcccgggaaacc  660
 V  L  S  Y  A  P  G  P  L  D  T  N  M  Q  Q  L  A  R  E  T
tccatggacccagagttgaggagcagactgcagaagttgaattctgaggggagctggtg  720
 S  M  D  P  E  L  R  S  R  L  Q  K  L  N  S  E  G  E  L  V
gactgtgggacttcagcccagaaactgctgagcttgctgcaaagggacaccttccaatct  780
 D  C  G  T  S  A  Q  K  L  L  S  L  L  Q  R  D  T  F  Q  S
ggagcccacgtggacttctatgacatttaa
 G  A  H  V  D  F  Y  D  I  -
```

HPLC analysis of culture supernatant of culture of the biopterin compound producing *Escherichia coli* JM101/pSTV28-GPS by a C18 reversed column TLC analysis of culture supernatant
of the biopterin compound producing yeast(FPS strain)

HPLC analysis of culture supernatant of the biopterin compound producing *Escherichia coli* AG14/pSTV28-GPS by a C18 reversed column Time course of BP and P production
by *Escherichia coli* AG14/pSTV28-GPS

Preparation of pUC18⊿E

Defect of EcoRI site

Fig. 28
Preparation of pSL1180MPS
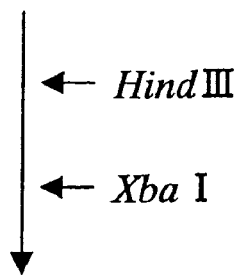
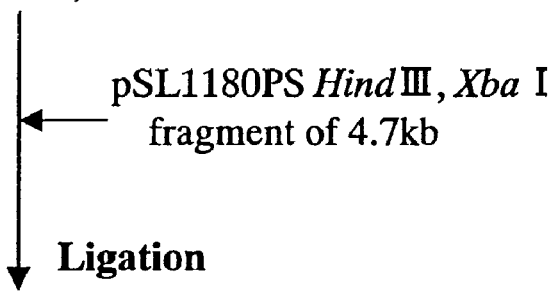
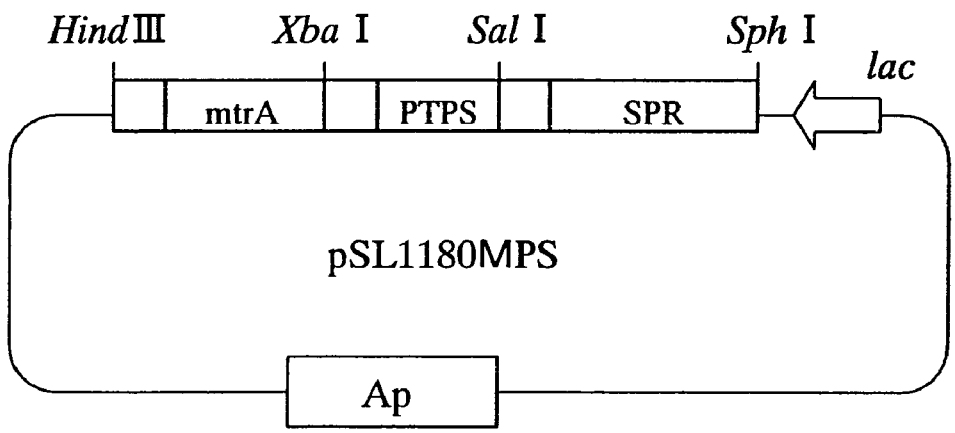

Fig. 29 Preparation of pDG148MPS

Fig. 31

ATGAGCAATATTACGAATTCCATGAAAGAAGTTAATAAAGAGCAAATCGAACAAGCTGTT 60
 M  S  N  I  T  N  S  M  K  E  V  N  K  E  Q  I  E  Q  A  V
CGTCAAATTTTAGAAGCGATCGGAGAAGACCCGAATAGAGAAGGGCTTCTTGATACTCCG 120
 R  Q  I  L  E  A  I  G  E  D  P  N  R  E  G  L  L  D  T  P
AAAAGAGTCGCAAAGATGTATGCCGAAGTATTCTCCGGCTTGAATGAAGATCCAAAAGAA 180
 K  R  V  A  K  M  Y  A  E  V  F  S  G  L  N  E  D  P  K  E
CATTTCCAGACTATCTTCGGTGAAAACCATGAGGAGCTTGTTCTTGTAAAAGATATAGCG 240
 H  F  Q  T  I  F  G  E  N  H  E  E  L  V  L  V  K  D  I  A
TTTCATTCTATGTGTGAGCATCACCTTGTTCCCTTTTATGGAAAAGCACATGTTGCATAT 300
 F  H  S  M  C  E  H  H  L  V  P  F  Y  G  K  A  H  V  A  Y
ATCCCGCGAGGCGGAAAGGTCACAGGACTCAGCAAACTGGCACGTGCCGTTGAAGCCGTT 360
 I  P  R  G  G  K  V  T  G  L  S  K  L  A  R  A  V  E  A  V
GCAAAGCGCCCGCAGCTTCAGGAACGCATCACTTCTACAATTGCAGAAAGCATCGTAGAA 420
 A  K  R  P  Q  L  Q  E  R  I  T  S  T  I  A  E  S  I  V  E
ACGCTTGATCCGCATGGCGTAATGGTAGTGGTTGAAGCGGAACACATGTGCATGACGATG 480
 T  L  D  P  H  G  V  M  V  V  V  E  A  E  H  M  C  M  T  M
CGCGGTGTAAGAAAACCGGGTGCGAAAACTGTGACTTCAGCAGTCAGAGGCGTTTTTAAA 540
 R  G  V  R  K  P  G  A  K  T  V  T  S  A  V  R  G  V  F  K
GATGATGCCGCTGCCCGTGCAGAAGTATTGGAACATATTAAACGCCAGGACTAA
 D  D  A  A  A  R  A  E  V  L  E  H  I  K  R  Q  D  -

Fig. 32

```
ATGAGCAATATTACGAATTCCATGAACGCGGCGGTTGGCCTTCGGCGCCGCGCGATTG   60
 M  S  N  I  T  N  S  M  N  A  A  V  G  L  R  R  R  A  R  L
TCGCGCCTCGTGTCCTTCAGCGCGAGCCACCGGCTGCACAGCCCATCTCTGAGTGCTGAG 120
 S  R  L  V  S  F  S  A  S  H  R  L  H  S  P  S  L  S  A  E
GAGAACTTGAAAGTGTTTGGGAAATGCAACAATCCGAATGGCCATGGGCACAACTATAAA 180
 E  N  L  K  V  F  G  K  C  N  N  P  N  G  H  G  H  N  Y  K
GTTGTGGTGACAATTCATGGAGAGATCGATCCGGTTACAGGAATGGTTATGAATTTGACT 240
 V  V  V  T  I  H  G  E  I  D  P  V  T  G  M  V  M  N  L  T
GACCTCAAAGAATACATGGAGGAGGCCATTATGAAGCCCCTTGATCACAAGAACCTGGAT 300
 D  L  K  E  Y  M  E  E  A  I  M  K  P  L  D  H  K  N  L  D
CTGGATGTGCCATACTTTGCAGATGTTGTAAGCACGACAGAAAATGTAGCTGTCTATATC 360
 L  D  V  P  Y  F  A  D  V  V  S  T  T  E  N  V  A  V  Y  I
TGGGAGAACCTGCAGAGACTTCTTCCAGTGGGAGCTCTCTATAAAGTAAAAGTGTATGAA 420
 W  E  N  L  Q  R  L  L  P  V  G  A  L  Y  K  V  K  V  Y  E
ACTGACAACAACATTGTGGTCTACAAAGGAGAATAG
 T  D  N  N  I  V  V  Y  K  G  E  -
```

Fig. 33

```
ATGAGCAATATTACGAATTCCGGCAGGCTAGGTTGCGCTGTCTGCGTGCTGACCGGGGCT  60
 M   S   N   I   T   N   S   G   R   L   G   C   A   V   C   V   L   T   G   A
TCCCGGGGCTTCGGCCGCGCCCTGGCCCCGCAGCTGGCCGGGTTGCTGTCGCCCGGTTCG 120
 S   R   G   F   G   R   A   L   A   P   Q   L   A   G   L   L   S   P   G   S
GTGTTGCTTCTAAGCGCACGCAGTGACTCGATGCTGCGGCAACTGAAGGAGGAGCTCTGT 180
 V   L   L   L   S   A   R   S   D   S   M   L   R   Q   L   K   E   E   L   C
ACGCAGCAGCCGGGCCTGCAAGTGGTGCTGGCAGCCGCCGATTTGGGCACCGAGTCCGGC 240
 T   Q   Q   P   G   L   Q   V   V   L   A   A   A   D   L   G   T   E   S   G
GTGCAACAGTTGCTGAGCGCGGTGCGCGAGCTCCCTAGGCCCGAGAGGCTGCAGCGCCTC 300
 V   Q   Q   L   L   S   A   V   R   E   L   P   R   P   E   R   L   Q   R   L
CTGCTCATCAACAATGCAGGCACTCTTGGGGATGTTTCCAAAGGCTTCCTGAACATCAAT 360
 L   L   I   N   N   A   G   T   L   G   D   V   S   K   G   F   L   N   I   N
GACCTAGCTGAGGTGAACAACTACTGGGCCCTGAACCTAACCTCCATGCTCTGCTTGACC 420
 D   L   A   E   V   N   N   Y   W   A   L   N   L   T   S   M   L   C   L   T
ACCGGCACCTTGAATGCCTTCTCCAATAGCCCTGGCCTGAGCAAGACTGTAGTTAACATC 480
 T   G   T   L   N   A   F   S   N   S   P   G   L   S   K   T   V   V   N   I
TCATCTCTGTGTGCCCTGCAGCCTTTCAAGGGCTGGGGACTCTACTGTGCAGGGAAGGCT 540
 S   S   L   C   A   L   Q   P   F   K   G   W   G   L   Y   C   A   G   K   A
GCCCGAGACATGTTATACCAGGTCCTGGCTGTTGAGGAACCCAGTGTGAGGGTGCTGAGC 600
 A   R   D   M   L   Y   Q   V   L   A   V   E   E   P   S   V   R   V   L   S
TATGCCCCAGGTCCCCTGGACACCAACATGCAGCAGTTGGCCCGGGAAACCTCCATGGAC 660
 Y   A   P   G   P   L   D   T   N   M   Q   Q   L   A   R   E   T   S   M   D
CCAGAGTTGAGGAGCAGACTGCAGAAGTTGAATTCTGAGGGGGAGCTGGTGGACTGTGGG 720
 P   E   L   R   S   R   L   Q   K   L   N   S   E   G   E   L   V   D   C   G
ACTTCAGCCCAGAAACTGCTGAGCTTGCTGCAAAGGGACACCTTCCAATCTGGAGCCCAC 780
 T   S   A   Q   K   L   L   S   L   L   Q   R   D   T   F   Q   S   G   A   H
GTGGACTTCTATGACATTTAA
 V   D   F   Y   D   I   -
```

P : Pterin, BP : Biopterin

PROCESS FOR PRODUCTION OF BIOPTERIN COMPOUND

This application is a continuation application of application Ser. No. 10/362,914, filed Apr. 26, 2003, now abandoned, which is a U.S. national stage of International Application No. PCT/JP01/07395 filed Aug. 28, 2001.

TECHNICAL FIELD

The present invention relates to transformed cell into which genes of one or more enzyme(s) participating in biosynthesis of tetrahydrobiopterin are introduced and also to a process for the production of a biopterin compound using the same.

BACKGROUND ART

In the present specification, tetrahydrobiopterin (L-erythro-5,6,7,8-tetrahydrobiopterin; hereinafter, referred to as THBP), 7,8-dihydrobiopterin (L-erythro-7,8-dihydrobiopterin; hereinafter, referred to as DHBP) or biopterin (hereinafter, referred to as BP) or a combination of any two or more of them is called a biopterin compound as a whole.

THBP is a biosubstance which is widely distributed in animals and was revealed to be a coenzyme of phenylalanine hydroxylase in liver of rat by Kaufman in 1963. After that, it was also revealed that THBP is a coenzyme which commonly acts on tyrosine hydroxylase and tryptophane hydroxylase and was revealed to play an important role participating in biosynthesis of neurotransmitters. In recent years, its function as a coenzyme for nitrogen monoxide (NO) synthase was also found and has been receiving public attention as a coenzyme for biosynthetic enzymes for various biosubstances. It has been known that, in human being, defect of THBP results in a reduction of activity of the above-mentioned amino acid hydroxylase causing an abnormally high phenylketonuria and abnormally high phenylalaninuria and THBP is used as a therapy for such inborn metabolism error diseases as sapropterin hydrochloride.

It has been known that, in animals, THBP is biosynthesized from guanosine triphosphate (hereinafter, abbreviated as GTP) by a three-step enzymatic reaction using GTP cyclohydrase I (hereinafter, abbreviated as GCH), 6-pyruvoyltetrahydropterin synthase (hereinafter, abbreviated as PTPS) and sepiapterin reductase (hereinafter, abbreviated as SPR) as shown in FIG. 1. In the meanwhile, other than the animals, THBP has been reported to be present in fruit fly (Weisberg, E. P. and O'Donnell, J. M. *J. Biol. Chem.* 261:1453-1458, 1996), silkworm (Iino, T., Sawada, H., Tsusue, M. and Takikawa, S.-I. *Biochim. Biophys. Acta* 1297:191-199, 1996), eukaryotic microbes such as *Euglena gracilis*, *Neurospora crassa* and *Pycomyces blakesleeanus* (Maier, J., Ninnemann, H. *Photochamistry and Photobiology* 61:43-53, 1995) and *Nocardia* species which are prokaryotic microbes (Son, J. K., Rosazza J. P. *J. Bacteriol.* 182:3644-3648, 2000). As such, although there are many living things in which the presence of THBP is reported, microbes are particularly greatly different from animals in view of evolution and, therefore, it is believed that THBP is not a biosubstance which is commonly available in microbes as a whole.

THBP is a compound having three asymmetric carbons in a molecular and, accordingly, it is a compound where its chemical synthesis is difficult and, with regard to its main synthetic methods, there has been known a method where L-erythro-biopterin (BP) is synthesized using rhamnose or deoxyarabinose as a starting material and then it is chemically subjected to an asymmetric reduction to synthesize the product. However, those chemically synthesizing methods have many reaction steps and, during the reaction steps, there are processes having low reaction yields. There are also difficulties that rhamnose and deoxyarabinose which are starting materials are expensive and they are hardly said to be advantageous manufacturing methods in terms of operation, yield, cost, and so on.

Under such circumstances, Kagamiyama, et al. tried the synthesis of THBP by an enzymatic reaction, purified each of the three enzymes participating in the THBP synthesis and by using the three enzymes succeeded in synthesizing the THBP in a reactor containing GTP and nicotinamide dinucleotide phosphate (reduced form) (hereinafter, abbreviated as NADPH) (Japanese Patent Laid-Open No. 82,888/1992). However, in obtaining 1 kg of THBP by this method, 3.12 kg of GTP and 92 kg of NADPH are necessary. When the facts that those materials are very expensive and that operations including purification of three kinds of enzymes are very troublesome are taken into consideration, industrial production of the biopterin compound using the said method is difficult in view of cost and operations.

On the other hand, Shiraishi, et al. found that enzymes of genus *Candida* (*Candida noveiius*, *Candida rugosa*, *Candida robsta*, etc.) and several filamentous fungi of genus *Mucor* (*Mucor javanicus*, *Mucor alternns*, *Mucor subtilissmus*, etc.) accumulate L-erythro-biopterin (BP) which is an oxidized product of THBP in a medium and reported a process for the production of BP from the culture medium utilizing the above property (Japanese Patent Laid-Open No. 9,296/1986 and No. 33,990/1993). Since BP is able to be converted to THBP by a chemical reduction, a method where BP is produced by microbes and then converted to THBP does not need expensive GTP and NADPH and, further, greatly reduces the synthesizing steps and, accordingly, it is an industrially advantageous manufacturing method in view of operations. However, in any of the strains, the amount of BP produced thereby is as low as that BP production per liter of the culture medium is not more than 1 mg and, therefore, it is not an industrially advantageous manufacturing method in view of yield and cost.

Accordingly, THBP which is useful as such has been hardly an object of study because there has been no industrially advantageous manufacturing method and, in addition, its usefulness has not been always sufficiently utilized because THBP has been hardly provided as pharmaceuticals, etc. in general. Further, although the biopterin compound such as DHBP and BP which are oxidized products of THBP which will be mentioned below have been expected to exhibit the same or even better pharmacological actions, the actions have not been fully investigated.

DISCLOSURE OF THE INVENTION

An object of the present invention is to provide a process for an industrially advantageous production of the biopterin compound in large quantities from less expensive starting material using a genetic engineering means.

Another object of the present invention is to provide a transformed cell being able to participate in biosynthesis of tetrahydrobiopterin into which gene of one or more enzyme(s) is introduced or to provide an expression vector having gene of one or more enzyme(s) being able to participate in biosynthesis of tetrahydrobiopterin used for the preparation of such a transformed cell.

Still another object of the present invention is to provide a mutant host cell such as a genetically recombined cell having a GTP synthetic ability of not less than the GTP synthetic ability of cells of a wild type or to provide a mutant host cell or a transformed cell having a GCH activity of not less than the GCH activity inherent to the cells of a wild type which is advantageous for production of tetrahydrobiopterin.

The present inventors have found that, when gene of enzyme participating in biosynthesis of THBP is introduced into host cell of microbe or the like which can be cultured in large quantities, the present substance can be biosynthesized at a low cost and in large quantities. Thus, since GTP which is a starting material for the THBP biosynthesis is a biosubstance commonly available in living things, it has been found that, when genes encoding enzymes for THBP biosynthesis in animals or other living things are introduced into a host cell by a genetic recombination technique, the host cell which is inherently unable to produce THBP is now able to produce THBP whereupon the present inventors have carried out an intensive investigation for preparation of such transformed cells.

On the other hand however, there is a possibility that synthesis of THBP in large quantities may be harmful to the host cell and it is forecasted that production of THBP by this method will be difficult as well. Thus, since THBP has a similar structure to folic acid because of the presence of a pteridine ring therein, it may be also regarded as a kind of folic acid analogs. Actually, there is a report where dihydrofolic acid reductase of *Escherichia coli* acts on 7,8-dihydrobiopterin (DHBP) which is an oxidized product of THBP whereby DHBP is converted to THBP (Watanabe, et al. *Seikagaku*, volume 53, no. 8, p. 1008 (1981)). Folic acid is a coenzyme participating in various carbon transition reactions in vivo and is a substance essential for the growth of cells and, therefore, when THBP is synthesized in significantly large amounts in cells, it is forecasted that the enzymatic reaction in which folic acid is participated is inhibited and that inhibition of growth of cells and succeeding death of the cells are resulted.

There are also reported that 7,8-dihydroneopterin produced from 7,8-dihydroneopterin triphosphate which is an intermediate for the THBP synthesis forms a radical (Oettl, K., et al. *Biochem. Biophys. Res. Commun.* 264:262-7, 1999) and that, when neopterin which is an oxidized product thereof is present together with hydrogen peroxide or nitrous acid, cytotoxicity of hydrogen peroxide and nitrous acid is further potentiated (Wede, I., et al. *Free Radic. Res.* 1999 November; 31(5):381-8). Accordingly, when THBP is produced in large quantities, 7,8-dihydroneopterin triphosphate as an intermediate is accumulated and that is converted to 7,8-dihydroneopterin by phosphatase in the cells whereby there might be a possibility of giving injury to the cells by radical formation or there might be a possibility of showing a cytotoxicity due to the coexistence of neopterin which is produced by oxidation with hydrogen peroxide and nitrous acid which are generated in the cells.

In addition, there is a risk of possibility that synthesis of THBP in large quantities reduces the pooling of GTP which is a substrate and NADPH which is a coenzyme in the cells whereby inhibition of the growth is resulted. Further, there is a risk of possibility that, when an enzyme which is necessary for biosynthesis of THBP is highly expressed in the cells, that might cause inhibition of cell growth. Furthermore, it is absolutely ambiguous whether the highly produced THBP in the cells surely transfers to a medium efficiently.

Taking the toxicity to the host cells as such into consideration, the present inventors introduced the gene of the enzyme participating in the THBP synthesis into *Escherichia coli* and *Saccharomyces* yeast which inherently have no the said synthesizing ability and investigated the productivity of biopterin compound. As a result, it was found that those transformed cells prepared as such did not cause inhibition of growth being worried about but produced biopterin compound in large quantities and was able to efficiently transfer the said biopterin compound to the culture medium. As a result of further invention, it was found that production of the biopterin compound by transformed cells into which gene of enzyme participating in the THBP synthesis was introduced was possible.

The present inventors have furthermore investigated to increase the production of the biopterin compound where *Escherichia coli* was used as an example. To begin with, since the starting substance for the THBP synthesis is GTP, preparation of host cells having a high GTP synthesizing ability than that of the cells of a wild type (hereinafter, abbreviated as highly GTP-synthetic host cells) was investigated.

It was found that, since GTP is a kind of purine compound, host cells carrying mutation for enhanced GTP synthesis were able to be obtained when mutant strain with deregulated purine biosynthesis pathway was screened. There is a report that, in the case of *Bacillus subtilis*, such a regulatory mutant strain for the purine synthesis can be obtained from mutants having a resistance to purine analogs such as 8-azaguanine and decoynine (refer, for example, to Ishii and Shiio, *Agric. Biol. Chem.* 36(9):1511-1522, 1972; Matsui, et al., *Agric. Biol. Chem.* 43(8):1739-1744, 1979) although, in the case of *Escherichia coli*, it has been ambiguous whether such purine analogs are effective for collection of highly GTP-synthetic host cells.

The present inventors succeeded in obtaining highly GTP-synthetic cells using purine analogs such as 8-azaguanine and decoynine even in the case of *Escherichia coli*. The present inventors further found a wonderful fact that, when such a regulatory mutant strain for the purine synthesis where the GTP synthetic ability is potentiated was used as a host cell, productivity for the biopterin compound was about ten-fold as compared with the case where a wild type was used as a host cell and, moreover, DHBP was produced in a significant amount as well.

It was further investigated as a method for preparing the highly GTP-synthesizing host cells that guaBA gene which codes for IMP dehydrogenase and GMP synthase converting inosinic acid to guanylic acid is introduced into cell to increase the activity of the said both enzymes. As a result, it was found that, when the guaBA gene was introduced into *Escherichia coli* which is the above-mentioned regulatory mutant strain for purine synthesis and such genetically recombinant cell is used as a host cell, production of the biopterin compound further increased as compared with the use of the already-mentioned regulatory mutant strain for the purine synthesis.

The present inventors furthermore carried out an intensive investigation for increasing the productivity of the biopterin compound and, as a result, they found that, when gene for the enzyme participating in the THBP synthesis is introduced into host cell for plural times to increase the expressed amount, there was an improvement in the productivity of the biopterin compound. It was unexpectedly found that, especially when GCH gene which is an enzyme for catalyzing the first step reaction for the THBP synthesis is introduced into the host cell for plural times to increase the expressed amount of GCH, productivity of the biopterin compound significantly increased.

On the basis of the above-finding that productivity for the biopterin compound significantly increases when GCH gene is introduced into host cells for plural times, the use of GCH gene of *Bacillus subtilis* (may also be called mtrA gene) was investigated whereupon it was unexpectedly found that the produced amount of the biopterin compound further increased.

As such, the present invention is able to provide an industrially advantageous process for producing the biopterin compound such as THBP and also to provide transformed cells and host cells which are useful for such a production.

As a result of further investigation, the present inventors have achieved the present invention.

Thus, the present invention relates to:

(1) In a process for production of the biopterin compound by a transformed cell, a process for production of the biopterin compound which is characterized in that (a) a host cell is transformed by at least one gene of enzyme participating in biosynthesis of tetrahydrobiopterin, (b) the resulting transformed cell is cultured to produce tetrahydrobiopterin, (c) the resulting tetrahydrobiopterin is oxidized if necessary and (d) one or more biopterin compound(s) selected from the resulting tetrahydrobiopterin and dihydrobiopterin and biopterin where the said tetrahydrobiopterin is oxidized is/are collected;

(2) the process for production of the biopterin compound mentioned in the above (1), wherein the biopterin compound in the culture broth or in a processed product thereof is oxidized and biopterin is collected therefrom;

(3) the process for production of the biopterin compound mentioned in the above (1) or (2), wherein the collected dihydrobiopterin and/or biopterin are/is reduced to produce tetrahydrobiopterin;

(4) the process for production of the biopterin compound mentioned in the above (1) to (3), wherein the enzyme(s) participating in the biosynthesis of tetrahydrobiopterin is/are one to three kind(s) of enzyme(s) selected from a group consisting of GTP cyclohydrase I 6-pyruvoyltetrahydropterin synthase and sepiapterin reductase;

(5) the process for production of the biopterin compound mentioned in the above (1) to (3), wherein the transformation is carried out by an expression vector having gene of 6-pyruvoyltetrahydropterin synthase and gene of sepiapterin reductase;

(6) the process for production of the biopterin compound mentioned in the above (5), wherein the host cell is a mutant cell having a GTP cyclohydrase I activity which is not less than the GTP cyclohydrase I activity inherent to the cell of a wild type;

(7) the process for production of the biopterin compound mentioned in the above (4), wherein the GTP cyclohydrase I gene to be introduced into the host cell is mtrA gene derived from *Bacillus subtilis*;

(8) the process for production of the biopterin compound mentioned in the above (1) to (7), wherein the host cell is a prokaryotic cell;

(9) the process for production of the biopterin compound mentioned in the above (8), wherein the prokaryote is *Escherichia coli, Bacillus subtilis* or *Actinomyces*;

(10) the process for production of the biopterin compound mentioned in the above (1) to (7), wherein the host cell is an eukaryotic cell;

(11) the process for production of the biopterin compound mentioned in the above (10), wherein the eukaryote is yeast or filamentous fungi;

(12) the process for production of the biopterin compound mentioned in the above (11), wherein the yeast is methanol assimilating yeast or fission yeast;

(13) the process for production of the biopterin compound mentioned in the above (11), wherein the yeast is *Saccharomyces* yeast;

(14) the process for production of the biopterin compound mentioned in the above (1) to (13), wherein the host cell is a mutant cell having a GTP synthesizing ability of not less than the GTP synthesizing ability of the cell of a wild type;

(15) the process for production of the biopterin compound mentioned in the above (14), wherein the host cell is a mutant cell having a 8-azaguanine resistance of not less than the 8-azaguanine resistance of the cell of a wild type;

(16) the process for production of the biopterin compound mentioned in the above (14) or (15), wherein the host cell is a genetically recombinant cell where guaBA gene coding for IMP dehydrogenase and GMP synthase is introduced thereinto;

(17) a transformed cell used for the production of the biopterin compound mentioned in the above (1) to (16) in which gene of an enzyme participating in biosynthesis of tetrahydrobiopterin is introduced into a host cell;

(18) the transformed cell according to the above (17), wherein the host cell is a mutant cell having a GTP synthesizing ability of not less than the GTP synthesizing ability of the cell of a wild type;

(19) the transformed cell according to the above (18), wherein the host cell is a mutant cell having a 8-azaguanine resistance of not less than the 8-azaguanine resistance of the cell of a wild type;

(20) the transformed cell according to the above (18) or (19), wherein the host cell is a genetically recombinant cell where guaBA gene coding for IMP dehydrogenase and GMP synthase is introduced thereinto;

(21) the transformed cell according to the above (18), wherein the host cell is a mutant cell having a GTP cyclohydrase I activity which is not less than the GTP cyclohydrase I activity inherent to the cell of a wild type and gene of 6-pyruvoyltetrahydropterin synthase and gene of sepiapterin reductase are introduced into the said host cell;

(22) the transformed cell according to the above (17)~(21), wherein the GTP cyclohydrase I gene to be introduced into the host cell is mtrA gene derived from *Bacillus subtilis;*

(23) the process for production of the biopterin compound mentioned in the above (14) or (15), wherein a transformed cell where guaBA gene coding for IMP dehydrogenase and GMP synthase is introduced into the host cell is used; and

(24) a transformed cell mentioned in the above (18) or (19) where guaBA gene coding for IMP dehydrogenase and GMP synthase is introduced into a host cell.

BRIEF DESCRIPTION OF THE DRAWINGS

FIG. 8 shows the steps for preparations of pYES2-PTPS and pYES2-SPR. PCR(P25, P26) means a PCR using sense primer P25 and antisense primer P26. PCR(P27, P28) has the similar meaning as well. Ap means ampicillin-resistant gene and URA3 means URA3 gene used as a selective marker in yeast. lac means lac promoter, $^P$GAL1 means GALL promoter and CYC1 TT means transcription termination signal of CYC1 gene.

FIG. 10 shows an amino acid sequence (SEQ ID No. 54) corresponding to a DNA base sequence of GCH cloned on pSTV28-GCH. The underlined part shows a sequence derived from pSTV28 to be added to an amino terminus of GCH.

FIG. 11 shows an amino acid sequence (SEQ ID No. 55) corresponding to a DNA base sequence of PTPS cloned on pUC18-PTPS. The underlined part shows a sequence derived from pUC18 to be added to an amino terminus of PTPS.

FIG. 12 shows an amino acid sequence (SEQ ID No. 56) corresponding to a DNA base sequence of SPR cloned on pUC19-SPR. The underlined part shows a sequence derived from pUC19 to be added to an amino terminus of SPR.

FIG. 28 shows the steps for preparation of pSL1180 MPS. Ap means ampicillin-resistant gene, PTPS means PTPS gene, SPR means SPR gene, mtrA means mtrA gene and SD means gene containing SD sequence and DNA sequence coding for translation initiation region. lac means lac promoter.

FIG. 31 shows amino acid sequence (SEQ ID No. 57) corresponding to DNA base sequence of mtrA cloned on pUC18AESDmtrA. The underlined part shows amino acid sequence derived from CcpA protein to be added to amino terminus of mtrA (Fujita, et al., *Microbiology*, 140:6571-6580, 1998) and base sequence corresponding thereto.

FIG. 32 shows amino acid sequence (SEQ ID No. 58) corresponding to DNA base sequence of PTPS cloned on pUC18SDPTPS. The underlined part shows amino acid sequence derived from CcpA protein to be added to amino terminus of PTPS (Fujita, et al., *Microbiology*, 140:6571-6580, 1998) and base sequence corresponding thereto.

FIG. 33 shows amino acid sequence (SEQ ID No. 59) corresponding to DNA base sequence of SPR cloned on pUC18AESDSPR. The underlined part shows amino acid sequence derived from CcpA protein to be added to amino terminus of SPR (Fujita, et al., *Microbiology*, 140:6571-6580, 1998) and base sequence corresponding thereto.

BEST MODE FOR CARRYING OUT THE INVENTION

Figure 1:
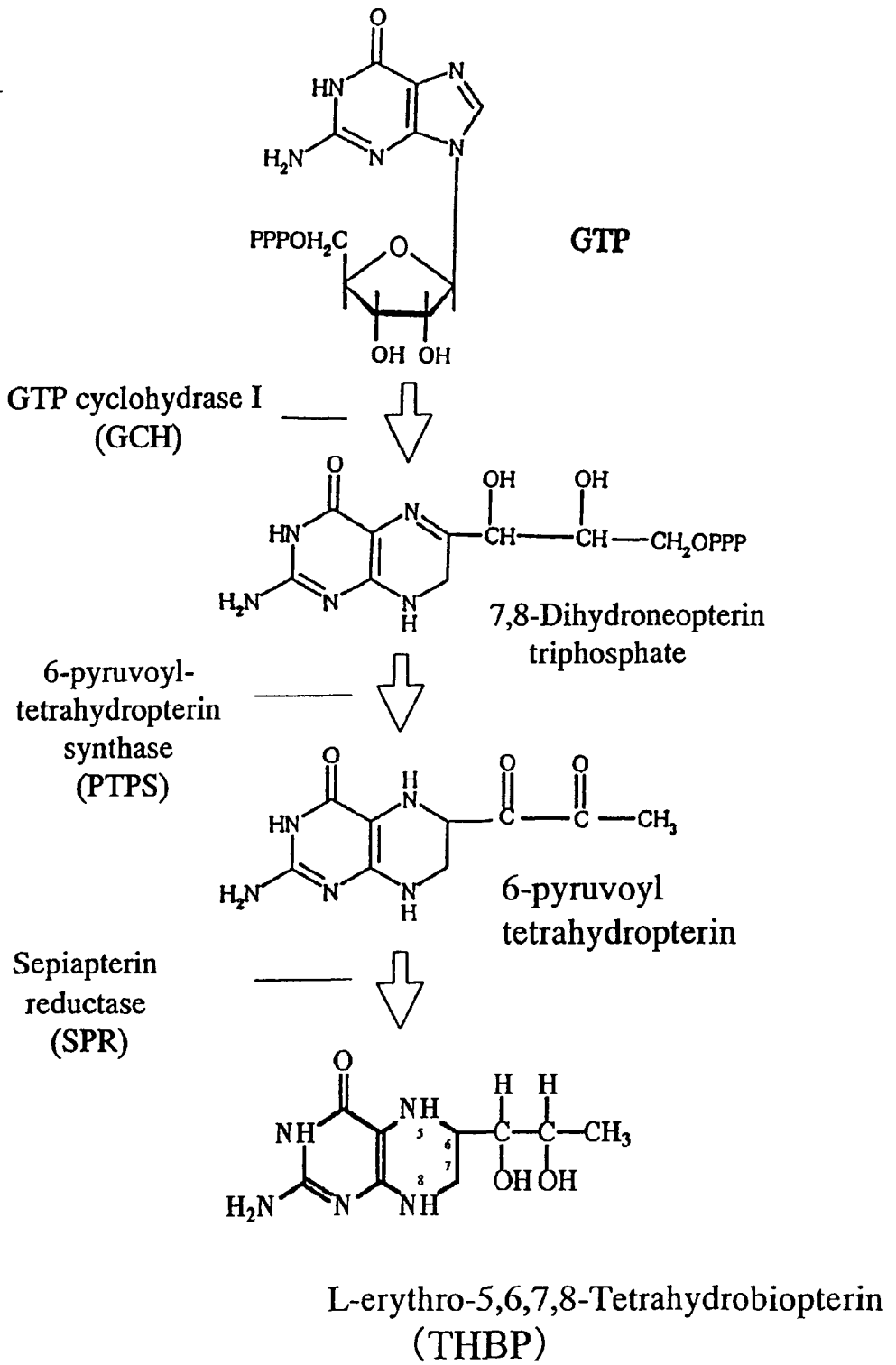
FIG. 1 shows a pathway for biosynthesis of tetrahydrobiopterin.

With regard to the enzyme which is able to participate in biosynthesis of tetrahydrobiopterin, there are exemplified enzymes such as guanosine triphosphate cyclohydrase I (GCH), 6-pyruvoyltetrahydropterin synthase (PTPS) and sepiapterin reductase (SPR) shown in FIG. 1.

With regard to the gene to be introduced into a host cell, anything may be used so far as it contains gene which codes for the above-mentioned enzyme. To be more specific, not only DNA containing GCH gene derived from *Escherichia coli* as shown in FIG. 10 or GCH gene derived from *Bacillus subtilis* as shown in FIG. 31, PTPS gene derived from rat as shown in FIG. 11 and FIG. 32 and SPR gene derived from rat as shown in FIG. 12 and FIG. 33 but also DNA which hybridizes with the said DNA may be used. Examples of the DNA which is able to hybridize with the said DNA are DNA containing a base sequence having a homology of not less than about 80%, preferably not less than about 85%, more preferably not less than about 90% and, most preferably, not less than about 95% to the base sequence shown in FIGS. 10-12 and FIGS. 31-33.

Hybridization may be carried out by a known method per se or a method similar to that such as a method mentioned in "Molecular Cloning" 2nd edition (J. Sambrook et al., Cold Spring Harbor Lab. Press, 1989). When commercially available cDNA library or kit is used, a method mentioned in the instructions attached thereto may be used. More preferably, hybridization may be carried out under a highly stringent condition. An example of a highly stringent condition is a condition where sodium concentration is about 19 to 40 mM or, preferably, about 19 to 20 mM and temperature is about 50 to 70° C. or, preferably, about 60 to 65° C. Especially, the case where sodium concentration is about 19 mM and temperature is about 65° C. is most preferred.

DNA upon introduction into a host cell may be any of genomic DNA, cDNA derived from cells or tissues and synthetic DNA. Vector which is used for introduction of gene may be any of bacteriophage, plasmid and cosmid. Further, cDNA may be directly amplified by a reverse transcriptase polymerase chain reaction (hereinafter, abbreviated as RT-PCR) using total RNA or mRNA fraction prepared from the above-mentioned cells or tissues. Furthermore, that which is manufactured by a synthetic method for oligonucleotide which is known per se may be used. To be more specific, an example is a method where chemical synthesis is carried out by a DNA synthesizer such as model 392 (manufactured by Perkin Elmer) utilizing a phosphoramidite method.

More specifically, DNA containing an aimed gene to be introduced into a host cell may, for example, be prepared as follows.

With regard to GCH which is an enzyme catalyzing the reaction of the first step in the tetrahydrobiopterin biosynthesis, it is present in many host cells such as *Escherichia coli*, yeast cells, etc. in addition to animals as an enzyme participating in the folic acid synthesis and, therefore, DNA coding for GCH may be easily prepared, for example, by (1) a method where PCR is carried out using a synthetic DNA primer having a partial base sequence of the said DNA whereby DNA containing the aimed gene is amplified from a gene library etc. or (2) a method where selection is carried out by hybridization of an appropriate gene library with a thing where labeled with DNA fragment or synthetic DNA coding for a part of or whole region of GCH (probe). Such methods may be appropriately used in the present invention and, between the two, the former is preferred.

A method for hybridization may, for example, be carried out by a method mentioned in "Molecular Cloning" 2nd edition (J. Sambrook, et al., Cold Spring Harbor Lab. Press, 1989), etc. When commercially available library or kit is used, a method mentioned in the instruction attached thereto may be used. DNA having a partial base sequence used as a probe for hybridization may also be manufactured according to a synthetic method for oligonucleotide which is known per se.

In the present invention, it is preferred to use GCH gene of *Escherichia coli* (may also be called folE gene), GCH gene of yeast (may also be called FOL2 gene) or GCH gene of *Bacillus subtilis* (may also be called mtrA gene) as a GCH gene and it is more preferred to use GCH gene of *Bacillus subtilis*.

In order to obtain the DNA coding for PTPS and SPR which carry out the reactions of the second step and the third step for the tetrahydrobiopterin biosynthesis, a method where mRNA is extracted from liver of rat and then subjected to an RT-PCR is preferred. In extracting the said mRNA, a method which is known per se may be used. Cells are partially or completely destroyed using a surface-active agent such as NP-40, SDS, Triton X 100 or deoxycholic acid or using a physical means such as homogenizer or freeze-melting and then mRNA is separated. In order to prevent the degradation of RNA by RNase during the extraction, it is preferred to add an RNase inhibitor such as heparin, polyvinyl sulfate, bentonite, macaloid, diethyl pyrocarbonate or vanadium complex to the extract. With regard to the purification of mRNA containing polyA, that may be carried out by a purifying method by affinity column chromatography using poly U-Sepharose or the like where oligo dT-cellulose or Sepharose 2B is a carrier or by a batch method using the poly U-Sepharose or the like, fractionation by an SDG centrifugal method or by an agarose electrophoretic method.

cDNA is synthesized from mRNA fraction containing mRNA corresponding to PTPS and SPR obtained as such. With regard to a method for the synthesis of cDNA, methods which are known per se may be used and there is exemplified a method where, firstly, a single stranded DNA complementary to mRNA is synthesized by a reverse transcriptase in the presence of dATP, dGTP, dCTP and dTTP using mRNA as a template and oligo dT as a primer, then the template mRNA is digested and removed by treating with an alkali and, after that, double stranded cDNA is synthesized by a reverse transcriptase or DNA polymerase using the said single stranded cDNA as a template.

In order to select the cDNA containing the gene of the enzyme participating in synthesis of THBP such as GCH, PTPS or SPR from the cDNA library prepared as such, a hybridization method where DNA fragment containing the said enzyme gene is a probe is used. With regard to the hybridization method, there may be used the methods known per se such as that mentioned hereinabove. In order to check whether the selected cDNA codes for the enzyme participating in synthesis of THBP such as GCH, PTPS or SPR, it may be carried out in such a manner that cDNA is integrated, for example, into vector which is reproducible in *Escherichia coli* or COS cells and the vector is introduced into *Escherichia coli* or COS cells whereupon the enzyme is expressed.

The transformed cell in accordance with the present invention is usually such a thing that where the biopterin compound can be produced or productivity of the biopterin compound is improved by introduction of gene of at least one enzyme participating in the above THBP synthesis into host cell.

Accordingly, the host cell may be that which inherently has no producing ability of the biopterin compound or has some ability for producing the biopterin compound. Thus, among host cells, some of them inherently have any of 1 to 3 kind(s) of gene(s) among the enzymes participating in the above THBP synthesis and well express the said 1 to 3 kind(s) of enzyme(s). In that case, gene(s) of such enzyme(s) may not be introduced into the host cell so far as such enzyme(s) is/are concerned. Of course, it is still possible to introduce it/them for enhancing the productivity of the biopterin compound. However, if that is not the case or, in other words, gene(s) of the above-mentioned enzyme(s) is/are not present, it is usually necessary to introduce the gene of the said enzyme and, in case the said gene is present but the enzyme is not sufficiently expressed, it is preferred to introduce the gene of the said enzyme.

For example, the host cell may be prokaryotes such as bacteria of genus *Escherichia*, bacteria of genus *Bacillus* and bacteria of order *Actinomycetales* or may be eukaryotes such as yeast, filamentous fungi, insect cell, insect, animal cell and plant cell.

A specific example of the bacteria of genus *Escherichia* is the so-called colon bacillus and its examples are *Escherichia coli* K12.DH1 [*Proc. Natl. Acad. Sci. USA*, volume 60, 160 (1968)], JM101, JM103 [*Nucleic Acids Research*, volume 9, 309 (1981)], JA221 [*J. Mol. Biol.*, volume 120, 517 (1978)], HB101 [*J. Mol. Biol.*, volume 41, 459 (1969)] and C600 [*Genetics*, volume 39, 440 (1954)]. Among them, it is preferred to use *Escherichia coli* JM101 in the present invention.

An example of the bacteria of genus *Bacillus* is the so-called hay bacillus and its examples are *Bacillus subtilis* 1A1 strain (trpC2) (Fujita, et al., *Microbiology*, 140:6571-6580, 1998) or MI114 [*Gene*, volume 24, 255 (1983)] and 207-21 [*Journal of Biochemistry*, volume 95, 87 (1984)]. In the present invention, it is particularly preferred to use the former.

An example of bacteria of order *Actinomycetales* is the so-called *actinomyces* and specific examples thereof are genus *Streptomyces*, etc. Examples of the microbe belonging to genus *Streptomyces* are *Streptomyces lividans* 3131, etc.

With regard to the yeast, it is preferred to use yeast of genus *Saccharomyces*, methanol assimilating yeast or fission yeast. An example of the methanol assimilating yeast is *Pichia pastoris* and an example of the fission yeast is *Schizosaccharomyces pombe*. Examples of the yeast of genus *Saccharomyces* are *Saccharomyces cerevisiae* KA31, *Saccharomyces cerevisiae* AH22, AH22R-, NA87-11A, DKD-5D and 20B-12, *Schizosaccharomyces pombe* NCYC1913 and NCYC2036 and *Pichia pastoris* KM71. Among them, it is preferred to use yeast of genus *Saccharomyces* and particularly preferred to use *Saccharomyces cerevisiae* KA31 in the present invention.

Examples of the filamentous fungi are species belonging to *Acremonium, Aspergillus, Fusarium, Humicola, Mucor, Myceliophthora, Neurospora, Penicillium, Thielavia, Tolypocladium* and *Trichoderma*.

Examples of the insect cell are established cell derived from larva of *Spodoptera frugiperda* (Sf cell), MG1 cell derived from midgut of *Trichoplusia ni*, High Five TM cell derived from egg of *Trichooplusia ni*, cell derived from *Mamestrabrassicae* and cell derived from *Estigmena acrea*. Established cell derived from silkworm (*Bombyx mori* N; BmN cell), etc. may also be used. With regard to the above-mentioned Sf cell, there may be exemplified Sf9 cell (ATCC CRL 1711), Sf21 cell (for those, cf. Vaughn, J. L., et al., *in Vivo*, volume 13, 213-217 (1977)), etc.

With regard to the insect, there may be exemplified larva of silkworm, etc. (Maeda, et al., *Nature*, volume 315, 592 (1985)).

With regard to the animal cell, there may be exemplified monkey cell COS-7, Vero cell, Chinese hamster cell CHO, dhfr gene-deficient Chinese hamster cell CHO, mouse L cell, mouse AtT-20 cell, mouse myeloma cell, rat GH3 cell, human FL cell, 293 cell, C127 cell, BALB/3T3 cell and Sp-2 cell.

With regard to the plant cell, there may be exemplified tobacco cell and carrot cell.

With regard to the host cell in accordance with the present invention, there may be used a mutant cell having a GTP synthesizing ability which is not less than the GTP synthetic ability of the wild type cell of the above-mentioned host cell. The reason is that, since GTP which is a starting substance for the THBP synthesis is a kind of purine compound, supplying amount of GTP which is a starting substance increases when a regulatory mutant of purine synthesis pathway where the GTP synthesizing ability increases is used and, as a result, production of the biopterin compound increases as well. In order to obtain a regulatory mutant of purine synthesis pathway, a known method may be used. For example, a method where incubation is carried out using a medium to which a purine analog is added and a mutant having a resistance to the purine analog is selected may be listed. With regard to the purine analog, a substance which is known per se may be used where 8-azaguanine and decoynine may be exemplified and advantageously used. To be more specific, it is reported that, in the case of *B. subtilis*, said mutant cell can be achieved by preparing a mutant having a resistance to purine analogs such as 8-azaguanine and decoynine and other antagonists such as methionine sulfoxide (e.g., Ishii and Shiio, *Agric. Biol. Chem.* 36:1511-1522, 1972; Matsui, et al., *Agric. Biol. Chem.* 43:1739-1744, 1979).

As hereunder, there will be mentioned a preferred embodiment for obtaining a mutant cell having a resistance to 8-azaguanine which is not less than the resistance to 8-azaguanine of the wild type cell in the case of *Escherichia coli*. Thus, since *Escherichia coli* JM101 strain which is a host cell has a sensitivity to not less than about 100 μg/ml of 8-azaguanine and to about 500 μg/ml of decoynine, *Escherichia coli* JM101 strain which is subjected to a mutation treatment with N-methyl-N-nitro-nitrosoguanidine using a minimum agar medium containing about 100 μg/ml of 8-azaguanine or about 500 μg/ml of decoynine is plated whereupon resistant strain for each of them can be obtained.

It is possible by a genetic engineering manner to prepare a host cell having a GTP synthesizing ability which is not less than the GTP synthesizing ability of a wild type cell of the above-mentioned host cell. Thus, a recombinant cell where the gene for increasing the GTP synthesizing ability such as the gene of enzyme of the GTP biosynthesis system is introduced into a wild type cell or a mutant cell such as that having a highly GTP-synthesizing ability may be used as a host cell. With regard to the gene which improves the GTP synthesizing ability, that which is known per se may be used. With regard to the said gene, one type may be introduced into a wild type or mutant cell or two or more genes may be introduced into a wild type or mutant cell. To be more specific, with regard to a method for the preparation of recombinant cell where the GTP synthesizing ability is improved, there may be exemplified a method where guaBA gene encoding IMP dehydrogenase and GMP synthase carrying out a conversion of inosinic acid to guanylic acid (Tiedeman, A. A., et al. *J. Biol. Chem.* 260:8676-8679, 1985 and *Nucleic Acids Res.* 13:1303-1316, 1985 [GenBank M10101]) are introduced into a wild type or mutant cell. A method for the introduction of gene such as guaBA into a wild type or mutant cell may be easily carried out by a method which is known per se such as the following method.

In the present invention, gene of at least one kind of enzyme participating in the THBP synthesis may be introduced into the above-mentioned host cell. Thus, all genes of the enzymes participating in the THBP synthesis may be introduced or only gene of a part of the said enzymes may be introduced. To be specific, the cases where (a) genes of GCH, PTPS and SPR, (b) two genes from GCH, PTPS and SPR and (c) gene of any of GCH, PTPS and SPR are/is introduced may be exemplified.

It is also preferred to increase the expressed amount by introducing the gene of the same enzyme for plural times. It is particularly preferred that GCH gene is introduced for plural times and origins of the GCH gene may be same or different.

A preferred example of the present invention is to introduce the genes of PTPS and SPR because GCH is present in many host cells such as *Escherichia coli* and yeast as an enzyme participating in the synthesis of folic acid.

Another preferred embodiment is that, since the presence of PTPS in addition to GCH is reported, for example, in *Synechocystis* which is a photosynthetic Gram-negative bacterium (Lee, S. W. et al., *FEMS Microbiology Letter* 176:169-176, 1999), gene of SPR only is introduced into such a host cell.

It is also possible that the gene of enzyme participating in the THBP synthesis is introduced into a cell which inherently has a producing ability of the biopterin compound. That is because, as a result, enzymatic activity is enhanced and producing ability of the biopterin compound is enhanced.

In the case of production of the biopterin compound where gene of two kinds of enzymes—PTPS and SPR—are introduced and expressed while, with regard to GCH, that which is owned by the host cell is used, it is preferred, as a host cell, to use a mutant cell having an enzymatic activity of not less than the intrinsic GTP cyclohydrase I of the wild type cell has.

With regard to a method for obtaining such mutant cell, there are exemplified a method where mutant of promoter of GCH gene existing in chromosome is obtained, a method where new promoter is introduced into an upper stream of GCH gene in chromosome and a method where specific activity is enhanced as compared with that of the wild type cell as a result of mutation of structural gene of GCH.

With regard to a method for the introduction of gene of enzyme being participated in the tetrahydrobiopterin biosynthesis into the above-mentioned host cell, methods which are known per se may be used. Specific examples of such methods are (a) a method where the said gene is integrated into chromosome of the host cell and (b) a method where gene is made present as a plasmid using vector. Among them, the method of using vector is preferred from a viewpoint that DNA can be efficiently introduced.

With regard to the above-mentioned method (a) according to the present invention where the gene of the above-mentioned enzyme is integrated into chromosome of the host cell, there is exemplified a method where one end of a glass tube is made narrow by pulling, DNA is placed thereinto, penetrated into cell and is introduced either by electrophoretic means or by the pressure caused by sending air or nitrogen gas. Another example is a particle gun method where very fine particles of gold or silver are sprinkled with DNA and the particles adhered with DNA are shot to the host cell by means of gun powder or high-pressure gas so that DNA is introduced thereinto. Still another example is an electroporation where host cell and DNA are placed in a container and voltage is applied whereby a transient pore is resulted in the host cell and DNA is incorporated therein [Neumann, E., et al. *EMBO J.* 1, 841-845 (1982)].

With regard to a method for the introduction of gene concerning the present invention into a host cell using vector, a method which is known per se may be used. With regard to a vector, it is preferred to use expression vector which gives stable mRNA in large quantities and is made so as to efficiently translate the resulting mRNA in the host cell. When plural genes are introduced, it is desired to use vectors having different origin for replication both in the case of same genes or different genes. With regard to the vector used, there are exemplified plasmid derived from *Escherichia coli* (such as pBR322, pBR325, pUC12, pUC13, pUC18, pUC19 and pSTV28), plasmid derived from *Bacillus subtilis* (such as pUB110, pTP5 and pC194), plasmid derived from yeast (such as pSH19, pSH15 and pYES2), bacteriophage such as λ phage, animal viruses such as retrovirus, vaccinia virus and baculovirus, pA1-11, pXT1, pRc/CMV, pRc/RSV and pcDNAI/Neo.

Expression vector usually contains regulatory sequence so that the enzyme of the present invention is expressed or expression advantageously takes place. Each regulatory sequence may be native or foreign to the base sequence coding for the amino acid sequence of the enzyme protein. Such a regulatory sequence includes promoter, leader, polyadenylated sequence, propeptide sequence, enhancer, signal sequence, splicing signal, poly A added signal, SV40 duplicated origin (hereinafter, may be referred to as SV40ori) and transcription terminator although not limited thereto. Among the above, the preferred regulatory sequence contains at least promoter and transcription- and translation termination signals.

With regard to promoter, anything may be used so far as it is an appropriate promoter sequence which is a base sequence being recognizable by the host cell. When the host cell is bacterium of genus *Escherichia*, there may be exemplified trp promoter, trc promoter, lac promoter, recA promoter, λ PL promoter, lpp promoter and T7 promoter. Among those, preferred ones are trc promoter and lac promoter. When the host cell is a bacterium of genus *Bacillus*, there may be exemplified SPO1 promoter, SPO2 promoter and penP promoter. When the host cell is a bacterium of order *Actinomycetales*, there may be exemplified tipA which is a promoter inducing an antibiotic thiostrepton (Murakami, T., et al. (1989) *J. Bacteriol.*, 171, 1459), etc.

When the host cell is yeast, there may be exemplified PHO5 promoter, PGK promoter, GAL promoter, GAP promoter, ADH promoter and AOX1 promoter. Among them, GAL promoter is preferred.

When the host cell is filamentous fungus, there may be exemplified promoter obtained from gene coding for TAKA amylase of *Aspergillus oryzae*, aspartic acid proteinase of *Rhizomucor miehei*, neutral α-amylase of *Aspergillus niger*, acid-stable α-amylase of *Aspergillus niger*, glucoamylase (glaA) of *Aspergillus niger* or *Aspergillus awamori*, lipase of *Rhizomucor miehei*, alkaline protease of *Aspergillus oryzae*, triphosphoric acid isomerase of *Aspergillus oryzae*, acetamidase of *Aspergillus nidulans* and trypsin-like protease of *Fusarium oxysporum* (U.S. Pat. No. 4,288,627 and Japanese Patent Laid-Open No. 507102/2000).

When the host cell is animal cell, there may be exemplified SRa prompter, SV40 promoter, LTR promoter, CMV (cytomegalovirus) promoter and HSV-TK promoter.

When the host cell is insect cell, there may be exemplified polyhedrin promoter and P10 promoter.

When the host cell is plant cell, there may be exemplified 35S promoter of cauliflower mosaic virus.

With regard to transcription terminator, any sequence may be used so far as it is recognized by a host cell for terminating the transcription.

For example, when the animal cell is a host, there may be used transcription terminator sequence of each of genes derived from virus, various mammals and birds and, to be more specific, there may be used SV40 terminator of simian virus.

When the host cell is yeast, there may be exemplified, PHO5 terminator, PGK terminator, GAL terminator, GAP terminator, ADH terminator and AOX1 terminator.

When the host cell is filamentous fungus, there may be exemplified terminators obtained from the gene coding for TAKA amylase of *Aspergillus oryzae*, glucoamylase of *Aspergillus niger*, anthranilate synthase of *Aspergillus nidulans*, α-glucosidase of *Aspergillus niger* and trypsin-like protease of *Fusarium oxysporum*.

Expression vector may include signal sequence concerning secretion of protein.

With regard to signal sequence, a signal sequence of the gene to be introduced may be used or a signal sequence of the different gene may be used.

With regard to the signal sequence of the different gene, there may be exemplified alkaline phosphatase when the host cell is a bacterium of genus *Escherichia* and, when the host cell is a bacterium of genus *Bacillus*, there may be exemplified α-amylase signal sequence and subtilisin signal sequence.

When the host cell is yeast, there may be exemplified MFα signal sequence and SUC2 signal sequence.

When the host cell is filamentous fungus, there may be exemplified base sequences coding for signal peptide from *Aspergillus oryzae* TAKA amylase gene, *Aspergillus niger* neutral amylase gene, *Rhizomucor miehei* aspartic acid proteinase gene, *Humicola lanuginosa* cellulose gene and *Rhizomucor miehei* lipase gene.

When the host cell is animal cell, there may be exemplified insulin signal sequence, α-interferon signal sequence and antibody molecule signal sequence.

Expression vector may include a selective marker. For example, in the case of prokaryote such as *Escherichia coli* and *Bacillus subtilis*, there may be used various drug-resistant genes while, in the case of eukaryotic microbe such as yeast, there may be used gene complementary to auxotrophy of the host as a selective marker. To be more specific, there may be exemplified dihydrofolic acid reductase gene, methotrexate (MTX)-resistant gene, ampicillin-resistant gene, neomycin-resistant gene (G418-resistant), chloramphenicol-resistant gene, kanamycin-resistant gene and URA3 gene.

Expression vector may include one or more nucleic acid sequence(s) coding for one or more factor(s) (such as activator (for example, trans-acting factor), chaperone, SD sequence and processing protease) which is/are advantageous for expression of enzyme gene concerning the present invention.

Any factor which is functional in the selected host cell may be used as an expression vector concerning the present invention.

In the present invention, known expression vector may be used as well. For example, there may be listed PIN-III-ompA$_2$, etc. for *Escherichia coli* host cell. Further examples are pIJ702 for *Actinomyces* host cell and pNJ1053 for yeast host cell. When plant cell is host cell, there may be exemplified pBI121 (*Nucleic Acids Res.*, 12, 8771-8721 (1984)), etc. In addition, shuttle vector pDG148 (Karmazyn-Campelli, et al., *Cell*, 52, 697-704, 1988) may be used for *Escherichia coli* and *Bacillus subtilis* and are advantageously used in the present invention.

With regard to a method for integrating cDNA, etc. containing the gene of enzyme participating in the above THBP biosynthesis concerning the present invention, there may be used a method which is known per se such as cleaving by a restriction enzyme followed by bonding by a DNA ligase. With regard to the above-mentioned cDNA, etc., various treatments may be previously carried out such as treatment with exonuclease, addition of chemically synthesized DNA fragment and addition of cleavage sites for restriction enzymes by bonding of linker or by PCR so as to be easily integrated with the above vector or G,C-chain is elongated so as to add a connectable terminus at the terminus of vector DNA or double stranded cDNA.

When the vector containing the gene of enzyme which is able to participate in the THBP biosynthesis constructed as such is introduced into a host cell, it is possible to manufacture a transformed cell in accordance with the present invention.

With regard to a method for the transformation by introduction of the said expression vector into the host cell, known methods may be used. When the host cell is prokaryote such as bacterium of genus *Escherichia*, the introduction may be carried out by recovering the cells in a logarithmic growth phase followed by subjecting to a well-known CaCl$_2$ method (Graham, F. L. and van der Eb, A. *J. Virology*, 52, 456-467 (1973)). When MgCl$_2$ or RbCl is made coexistent in the transformation reaction solution, the transforming efficiency can be improved and, therefore, that may be coexisted in the present invention. It is also possible to carry out a transformation after preparation of protoplast of the host cell.

When the host cell used is eukaryote, it is possible to carry out the introduction by common methods such as a method where DNA is infected as a calcium phosphate precipitate, a microinjection method, a method where introduction is carried out by including plasmid with erythrocyte cell or liposome, a method of treating the cell with a reagent such as lysophosphatidylcholine and a method where virus vector is used. When the host cell is yeast, it is possible to use a lithium acetate method.

To be more specific, in the transformation of bacterium of genus *Escherichia*, that may be carried out by the methods described in *Proc. Natl. Acad. Sci. USA*, volume 69, 2110 (1972), *Gene*, volume 17, 107 (1982), etc.

In the transformation of bacterium of genus *Bacillus*, that may be carried out by the methods described in *Molecular & General Genetics*, volume 168, 11 (1979), etc.

In the transformation of yeast, that may be carried out by the methods described in *Methods in Enzymology*, volume 194, 182-187 (1991), *Proc. Natl. Acad. Sci. USA*, volume 75, 1929 (1978), etc.

In the transformation of insect cell or insect, that may be carried out by the methods described in *Bio/Technology*, 6, 47-55 (1988), etc.

In the transformation of animal cell, that may be carried out by the methods described in Saibo Kogaku, Supplementary Issue No. 8, *Shin Saibo Kogaku Jikken Protocol*, 263-267 (1995) (published by Shujunsha), *Virology*, volume 52, 456 (1973), etc.

In the transformation of plant cell, that may be carried out by introducing the gene in accordance with the present invention according to an *Agrobacterium tumefaciens* method (*Methods in Enzymol.*, 118, 627-640 (1986)), a high-speed fine particle method (*Plant Molecular Biology*, 11, 433-439 (1989)), a protoplast method (*Nature*, 319, 791-793 (1986)), etc.

With regard to a method for a stable expression of the enzyme of the present invention using animal cell, there is a method where the cell in which the expression vector introduced into the above animal cell is integrated with chromosome is selected by means of a clone selection. To be more specific, transformed cell is selected using the above-mentioned selecting marker as an index and the transformed cell which is obtained by the selective marker as such is repeatedly subjected to a clone selection whereupon a stable transformed cell having a high enzyme expressing ability according to the present invention is able to be obtained.

In the present invention, the above-mentioned transformed cell is cultured usually under such a condition that gene of enzymes participating in the THBP synthesis such as GCH, PTPS and SPR introduced therein is able to be expressed. In the cultivation, it is preferred that incubating temperature, pH of medium and dissolved oxygen level are constantly controlled. That is because, in order to suppress a reduction of growth of cell by, for example, lowering of pH of the medium as much as possible, to promote the growth and also to produce the biopterin compound more efficiently, it is preferred to make the culture conditions constant as mentioned above.

In the culture of transformed cell where the host cell is a bacterium of genus *Escherichia*, a bacterium of genus *Bacillus* or a bacterium of order *Actinomycetales*, a liquid medium is preferred as a medium used for the culture and the medium in which carbon source, nitrogen source, inorganic material and others necessary for the growth of the said transformed cell are contained is preferred. Examples of the carbon source are glucose, dextrin, soluble starch and sucrose; examples of the nitrogen source are ammonium salt, nitrate, corn steep liquor, peptone, casein, meat extract, soybean cake and potato extract and other inorganic or organic substances; and examples of the inorganic material are calcium chloride, sodium dihydrogen phosphate and magnesium chloride. Yeast extract, vitamins, growth-promoting factor, etc. may also be added to the above medium. PH of the medium is preferably to be about 5 to 8.

With regard to the medium for the culture of a bacterium of genus *Escherichia*, its specific examples are M9 medium containing glucose and Casamino acid (Miller, *Journal of Experiments in Molecular Genetics*, 431-433, Cold Spring Harbor Laboratory, New York, 1972), etc. and it is preferred that, after a pre-culture using an LB medium (refer to Example 4), a main culture is carried out using an NUCA medium (refer to Example 4). Here, in order to have a promoter act efficiently, a reagent such as 3β-indolylacrylic acid or chloramphenicol may be added thereto if necessary. When an inductive promoter is used, it is preferred to add a substance which causes the induction to the medium. For example, in the case of lac promoter, it is preferred to add isopropyl β-thiogalactopyranoside (IPTG) and, in the case of GAL promoter, it is preferred to add galactose. The culture is carried out preferably at about 10 to 50° C. for about 3 to 72 hours and, if desired, aeration or stirring may be conducted.

Culture of a bacterium of genus *Bacillus* is usually carried out at about 30 to 40° C. for about 6 to 40 hours and, if desired, aeration and stirring may be conducted. With regard to the medium, known ones may be used. To be more specific, it is preferred that, for example, a pre-culture is carried out using an LB medium (refer to Example 4) and then a main culture is carried out using an NU medium (refer to Example 14).

When the host cell is a bacterium of order *Actinomycetales*, it is usually carried out at about 20 to 40° C. for about 2 to 7 days and, if desired, aeration or stirring may be conducted. With regard to the medium, it is possible to use known media such as a GP medium (containing 0.4 wt % of glycerol, 0.1 wt % of peptone, 0.4 wt % of yeast extract, 0.05 wt % of magnesium sulfate, 0.2 wt % of monopotassium phosphate, 0.5 wt % of disodium phosphate and 0.1 wt % of glycine per one liter).

With regard to the medium for the culture of yeast, there may be exemplified a Burkholder minimum medium [Bostian, K. L., et al. *Proc. Natl. Acad. Sci. USA*, volume 77, 4505 (1980)] and an SD medium containing 0.5% of Casamino acid [Bitter, G. A., et al., *Proc. Natl. Acad. Sci. USA*, volume 81, 5330 (1984)]. Among those, an SD-Ura$^-$ medium (refer to Example 5) is preferred. It is preferred that pH of the medium is adjusted to about 5-8. Culture is preferably carried out at about 20~40° C. for about 24~84 hours and, if desired, aeration or stirring may be conducted.

When the host cell is a filamentous fungus, it is also possible to culture by a method known per se.

When a transformed cell where the host cell is insect cell or insect is cultured, examples of the medium are that where an additive such as inactivated 10% bovine serum is appropriately added to Grace's insect medium (Grace, T. C. C., *Nature*, 195, 788 (1962)), etc. It is preferred that pH of the medium is adjusted to about 6.2 to 6.4. Culture is preferably carried out at about 27° C. for about 3 to 5 days and, if desired, aeration or stirring may be conducted.

With regard to a medium for the culture of animal cell, there may be used an MEM medium containing about 5 to 20% of fetal bovine serum (*Science*, volume 122, 501 (1952)), a DMEM medium (*Virology*, volume 8, 396 (1959)), an RPMI 1640 medium (*J. Amer. Med. Assc.*, volume 199, 519 (1967)), a 199 medium (*Proc. Soc. Biol. Med.*, volume 73, 1 (1950)), etc. It is preferred that pH of the medium is about 6 to 8. Culture is preferably carried out at about 30 to 40° C. for about 15 to. 72 hours.

Examples of the medium for the culture of plant cell are a Murashige and Skoog (MS) medium, a White medium, etc.

As hereunder, preferred embodiments of the manufacturing method for biopterin compound according to the present invention will be mentioned.

The pSTV28 is used as a vector of an *Escherichia coli* type and there is prepared pSTV28-GPS which is a plasmid where cDNA of each of GCH, PTPS and SPR is aligned at the downstream of a lactose promoter. The said plasmid is an expression vector where an induction by IPTG is possible. The expression vector is introduced into an *Escherichia coli*

JM 101 strain and cultured in a medium containing 0.5 mM IPTG for about 48 hours whereby the biopterin compound can be manufactured.

Alternatively, yeast pYES2 is used as a vector and there is prepared pYES2-FPS which is a plasmid where cDNA of each of GCH, PTPS and SPR is aligned at the downstream of a GAL1 promoter. Such a plasmid is an expression vector where an expression induction by galactose is possible. The expression vector is introduced into *Saccharomyces* yeast and expression of each enzyme gene is carried out by induction with galactose whereby the biopterin compound can be manufactured.

There is also the following embodiment as a method for the manufacture of the biopterin compound according to the present invention. Thus, a shuttle vector pDG148 (Karmazyn-Campelli, et al., *Cell*, 52, 697-704, 1988) is used and there is prepared pDG148 MPS which is a plasmid where cDNA of each of GCH, PTPS and SPR is aligned at the downstream of spac promoter. The said plasmid is an expression plasmid for *Bacillus subtilis* which is able to be induced by IPTG. The expression vector is introduced into *Bacillus subtilis* 1A1 strain (trpC2) to prepare a transformed cell. Such a transformed cell is pre-culture in an LB medium containing about 5 μg/ml of kanamycin for about 3 hours and then subjected to a shaking culture in an NU medium containing about 1 mM of IPTG and about 5 μg/ml of kanamycin at about 37° C. for about 20 hours whereby the biopterin compound can be manufactured.

It is also possible that, when lacI gene is deleted from the above-mentioned shuttle vector pDG148, an expression vector pDG148MPSΔI which is able to always express GCH, PTPS and SPR regardless of presence or absence of IPTG is prepared. Such an expression vector may be used by the same manner as above except that IPTG is not necessary during the main culture.

Figure 2:
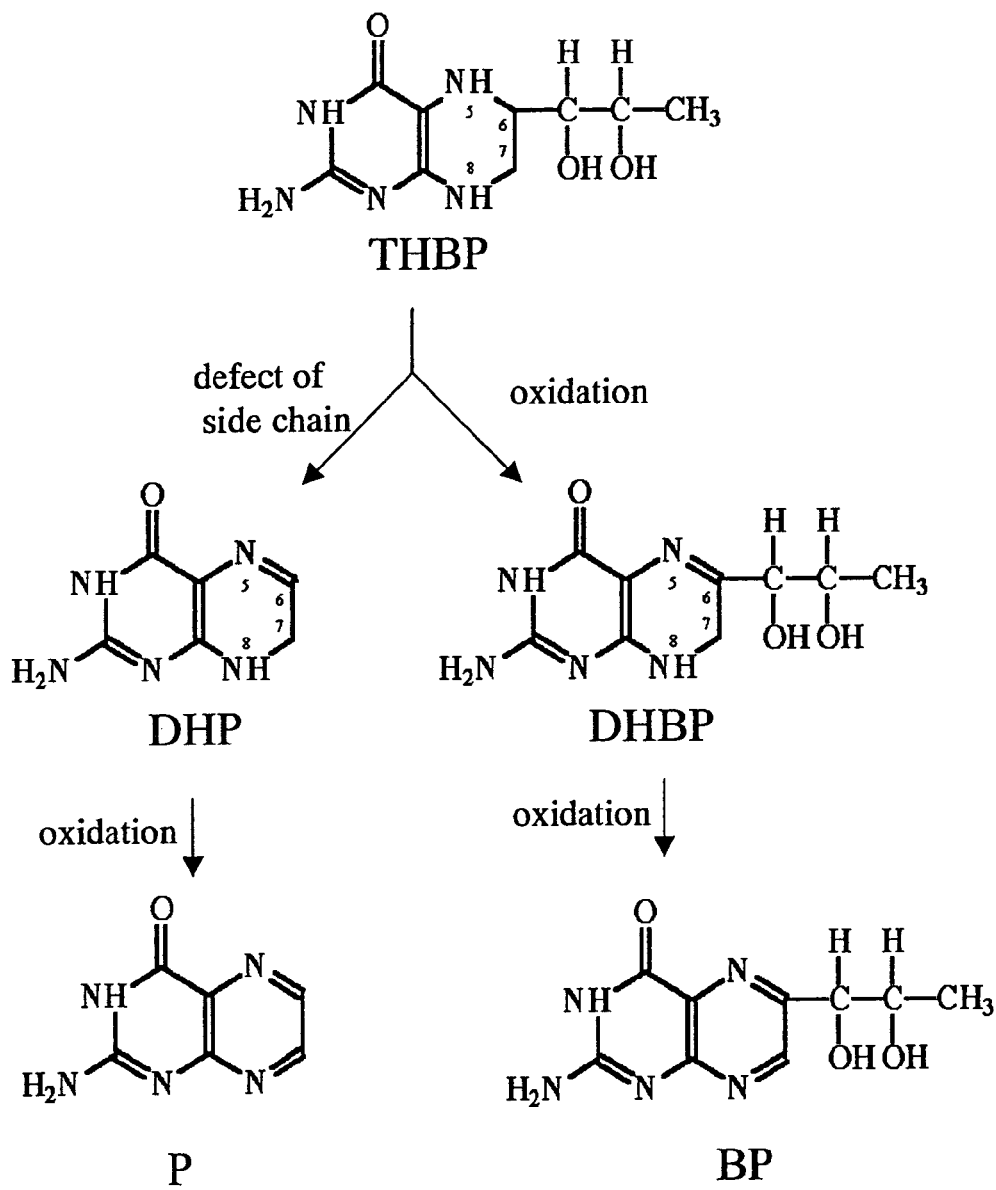
FIG. 2 shows a pathway for oxidation and decomposition of tetrahydrobiopterin.

THBP is produced from GTP which is inherently present in host cell by the enzyme which is able to participate in the THBP synthesis such as GCH, PTPS or SPR expressed in the transformed cell. The produced THBP is oxidized to DHBP as shown in FIG. 2 and then further oxidized to BP in the cell or after discharged outside the cell by passing through cell membrane in a medium such as a culture broth (Takikawa, et al., *Eur. J. Biochem.* 161:295-302, 1986). Thus, although an indiscriminate conclusion cannot be derived because of the difference due to type of the transformed cell and extracellular environment such as culture condition, only THBP is produced in the transformed cell in some cases while, in other cases, a part of or all of it is oxidized and DHBP or BP or a mixture thereof is available. There is also another case where the THBP produced in the transformed cell passes through a cell membrane and is discharged outside the cell. In that case, although an indiscriminate conclusion cannot be derived because of the difference due to composition of the culture media, the discharged THBP is sometimes oxidized to DHBP or BP in the culture media.

In the present invention, the biopterin compound in the culture broth or in the treated substance thereof such as a supernatant may be purified and separated by the following method. If desired, the culture broth or the treated substance thereof such as a supernatant is oxidized by, for example, adding an oxidizing agent thereto and, after that, the biopterin compound is purified and separated. Since THBP is an easily oxidized substance among the biopterin compounds, it is preferred that the culture broth or the treated substance thereof such as a supernatant is oxidized so that THBP or DHBP is oxidized to BP and, after that, chemically more stable BP is purified and separated.

With regard to a method for the oxidation of the biopterin compound in the culture broth or in the treated substance thereof such as a supernatant, known method per se may be used and a known oxidizing agent may be added to the culture broth or to the treated substance thereof such as a supernatant. Examples of the oxidizing agent are periodate such as potassium iodide, potassium or sodium dichromate, potassium permanganate, potassium nitrosodisulfonate and nitric acid and, among them, it is preferred to use potassium iodide.

In order to separate and purify the biopterin compound of the present invention from the above culture product, methods which are known per se may be used.

To be more specific, there may be appropriately used, for example, a method where fungus body or cell is collected by a known method after culture in extraction of the biopterin compound of the present invention from cultured fungus body or cell which is transformed cell and is suspended in an appropriate buffer followed by subjecting to a treatment with ultrasonic wave or lysozyme or to a freeze-melting and a method where fungus body or cell is destroyed by a combination of such a means, then transformed cell and supernatant of culture broth are separated by a means which is known per se such as centrifugation or filtration and the supernatant is collected wherefrom a solution in which the biopterin compound of the present invention is dissolved is obtained.

When THBP produced in the transformed cell is discharged outside the cell by passing through a cell membrane, there may be appropriately used, for example, a method where transformed cell and supernatant are separated by a known means per se such as centrifugation or filtration without destroying the transformed cell and the supernatant is collected wherefrom the solution in which the biopterin compound of the present invention is dissolved is obtained.

Purification of the biopterin compound of the present invention which is contained in the culture broth or the treated product thereof such as supernatant prepared as such may be carried out by an appropriate combination of separating and purifying methods which are known per se.

With regard to such known methods for separation and purification, there may be used a method where solubility is utilized such as salting out and solvent precipitation; a method where difference in molecular weights is mainly utilized such as dialysis, ultrafiltration, gel filtration and SDS-polyacrylamide gel electrophoresis; a method where difference in charges is utilized such as ion-exchange chromatography; a method where specific affinity is utilized such as affinity chromatography; a method where difference in hydrophobicity is utilized such as a reversed phase high performance liquid chromatography; a method where difference in isoelectric point is utilized such as isoelectric focusing; and the like.

When the biopterin compound of the present invention obtained as such is obtained in a free form, it may be converted to a salt by a known method per se or by a method similar to that and, conversely, when it is obtained in a form of salt, it may be converted to a free substance or to other salt by a known method per se or by a method similar to that.

Preferred embodiment of purification of the biopterin compound of the present invention is a method where the culture broth is oxidized with a potassium iodide solution under an acidic condition to convert to BP and then pure BP is obtained by way of precipitating operation, Dowex 1×8 chromatography and Florisil chromatography.

The biopterin compound which is obtained as such is able to be converted to THBP, if desired, using a known means. For example, BP or DHBP can be converted to THBP by a chemical hydrogenation reaction. In the chemical hydrogenation reaction, a known method per se may be used and there may be exemplified a method where the reaction is carried out with lithium aluminum hydride, lithium boron triethyl hydride, sodium boron hydride, diborane, alkyl diborane, etc. and a method where reduction is carried out using Raney nickel catalyst. Reaction condition therefor may be in accordance with the known methods. Under some reduction conditions, it is also possible to obtain DHBP from BP.

As mentioned above, THBP has been known as a coenzyme for various kinds of enzymes and is a substance expected to be a substance having such a pharmacological action. In addition, DHBP or BP is not only useful as a provider for such a THBP but also is a useful substance having a possibility of exhibiting a pharmacological action.

EXAMPLES

Examples of the present invention will be shown as follows. Incidentally, the following basic operations of genetic engineering or biological engineering were carried out according to the methods mentioned in "Molecular Cloning" (Cold Spring Harbor Laboratory, 1982); "Molecular Cloning" 2nd edition (Cold Spring Harbor Laboratory, 1989); *Methods in Enzymol.*, volume 194 (1991); *Jikken Igaku* (Supplementary Issue), *Kobo ni yoru Idenshi Jikkenho* (Methods for Genetic Experiments Using Enzymes), Yodosha (1994); etc. When a commercially available kit was used, the instructions attached thereto were followed.

Example 1

Preparation of GCH Gene, PTPS Gene and SPR Gene

1. Cloning of GCH (GTP Cyclohydrase I) Gene Derived from *Escherichia coli*

Genomic DNA was extracted from *Escherichia coli* (W3110 strain) by a reported method (*Seibutsu Kogaku Jikkensho* [published by Baifukan, pages 97-98]). This was used as a template and a PCR was carried out by a conventional manner using sense primer P1 (SEQ ID NO: 1) and antisense primer P2 (SEQ ID NO: 2) to prepare GCH gene (folE) [Katzenmeier, G., et al., *Bio Chem Hoppe Seyler* 372: 991-997, 1991, [GenBankx63910]]. After that, DNA containing the resulting GCH gene was used as a template and a PCR was carried out using sense primer P3 (SEQ ID NO: 3) and antisense primer P4 (SEQ ID NO: 4) to add cleavage sites for restriction enzymes EcoRI and SpeI to the untranslated regions of 5'end and 3'end of GCH gene, respectively. This PCR product was digested by EcoRI and SpeI and introduced into the EcoRI and SpeI sites of vector of pProEX HTa (GIBCO BRL) to prepare pProEX-GCH. Incidentally, PCR condition, treatment with restriction enzyme and ligation reaction were carried out according to conventional methods.

Figure 3:
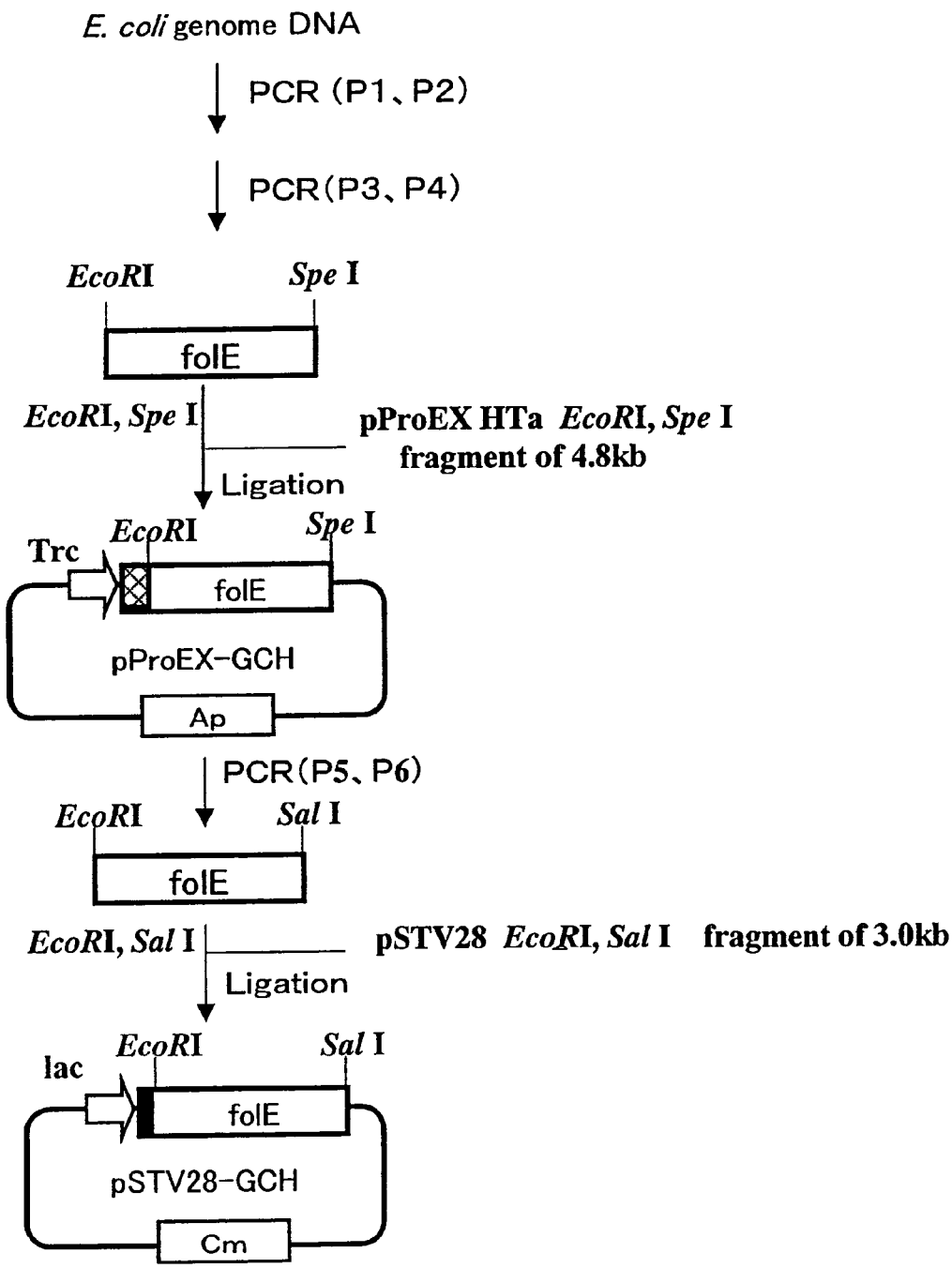
FIG. 3 shows the steps for preparation of pSTV28-GCH. PCR (P1, P2) means a PCR using sense primer P1 and antisense primer P2. PCR(P3, P4) and PCR(P5, P6) have the similar meanings as well. Ap means ampicillin-resistant gene and Cm means chloramphenicol-resistant gene. trc means trc promoter and lac means lac promoter.

After that, a PCR was carried out using pProEX-GCH as a template and using sense primer P5 (SEQ ID NO: 5) and antisense primer P6 (SEQ ID NO: 6) for cloning the *Escherichia coli* GCH gene which was cloned to pProEX-GCH to a plasmid pSTV28 (Takara Shuzo) to prepare GCH gene having cleavage sites for the restriction enzymes EcoRI and SalI at the termini of 5'end and 3'end, respectively. The resulting PCR product was cleaved by restriction enzymes EcoRI and SalI and connected to EcoRI and SalI fragments (3.0 kb) of pSTV28 (hereinafter, may be sometimes referred to as EcoRI-SalI fragment or EcoRI, SalI fragment; that will be applied to others as well) to give *Escherichia coli* GCH expression plasmid pSTV28-GCH (FIG. 3). The GCH gene (folE) contained in pSTV28-GCH was transcribed by *Escherichia coli* lactose (lac) promoter and the GCH expressed hereby had an amino acid sequence where 7 amino acids (underlined part in FIG. 10) derived from pSTV28 were added to the amino terminus (FIG. 10).

2. Cloning of PTPS (6-pyruvoyltetrahydropterin Synthase) Gene Derived from Rat

Figure 4:
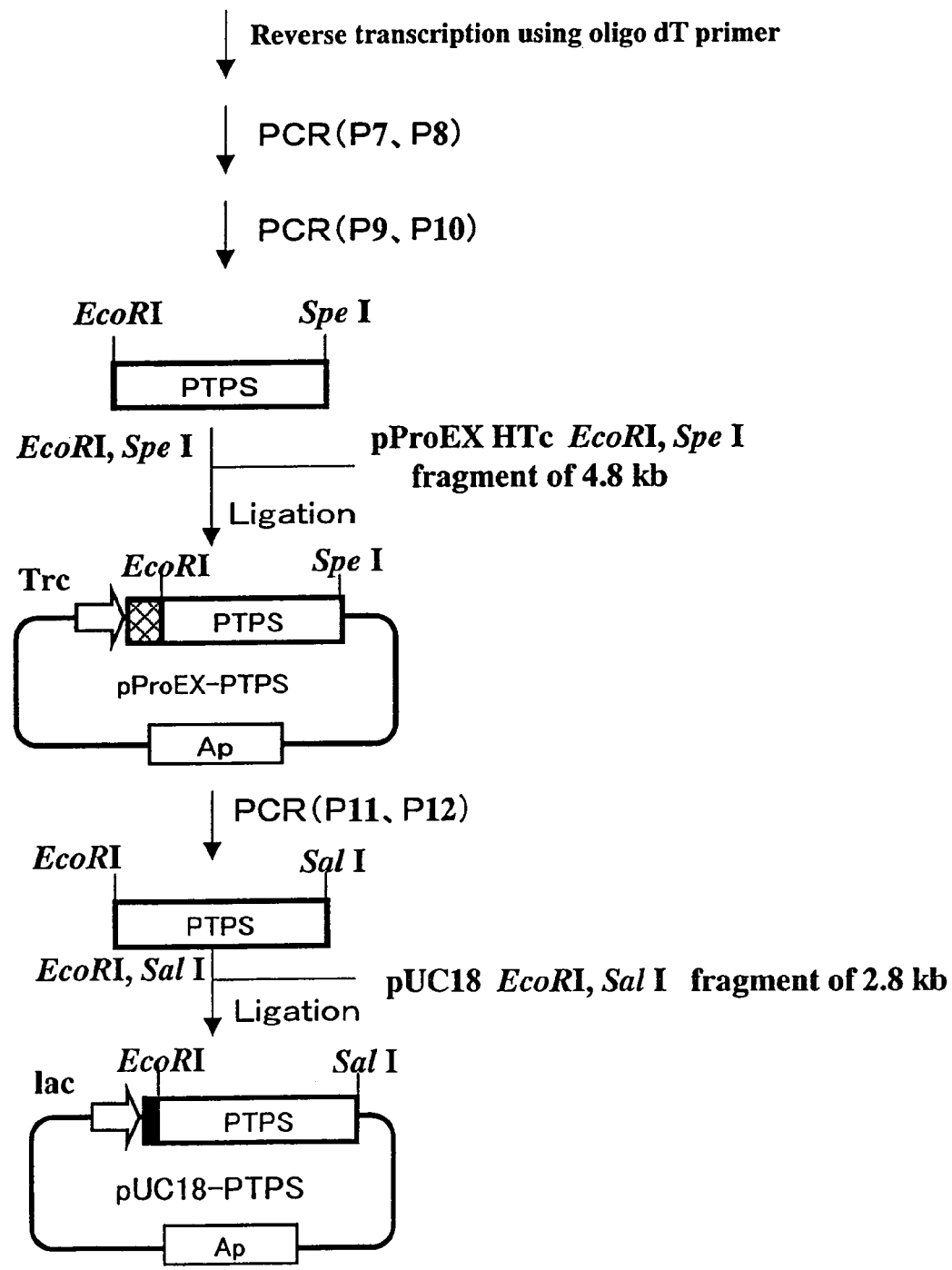
FIG. 4 shows the steps for preparation of pUC18-PTPS. PCR (P7, P8) means a PCR using sense primer P7 and antisense primer P8. PCR(P9, P10) and PCR(P11, P12) have the similar meanings as well. Ap means ampicillin-resistant gene. trc means trc promoter and lac means lac promoter.

Liver excised from rat was treated with collagenase and the resulting hepatic cell was treated with a TRIzol reagent (GIBCO BRL) to extract total RNA. The total RNA from rat hepatocyte treated with DNase was subjected to an RT-PCR using Super Script Preamplification System (GIBCO BRL) to prepare cDNA containing PTPS gene (Inoue, Y., et al., *J. Biol. Chem.* 266:20791-20796, 1991: [GenBank NM_017220]). Here, oligo dT primer was used for reverse transcription while, for amplification of a single stranded DNA containing PTPS gene by PCR, there were used sense primer P7 (SEQ ID NO: 7) and antisense primer P8 (SEQ ID NO: 8). A PCR was carried out using the resulting cDNA containing PTPS as a template and using sense primer P9 (SEQ ID NO: 9) and antisense primer P10 (SEQ ID No: 10) to add the cleavage sites for restriction enzymes EcoRI and SpeI to the untranslated regions at 5'end and 3'end, respectively, of cDNA containing PTPS gene. The PCR product was digested by EcoRI and SpeI to insert into the EcoRI and SpeI sites of pProEX HTc vector (GIBCO BRL) whereupon pProEX-PTPS was prepared (FIG. 4).

After that, a PCR was carried out using pProEX-PTPS as a template and using sense primer P11 (SEQ ID NO: 11) and antisense primer P12 (SEQ ID NO: 12) to give PTPS gene having the cleavage sites for the restriction enzymes EcoRI and SalI. The resulting PCR product was cleaved by the restriction enzymes EcoRI and SalI and connected to EcoRI and SalI fragment (2.7 kb) of pUC18 (Yanisch-Perron, C., Vieira, J. and Messing, J. *Gene*, 33:103-119, 1985) to give rat PTPS expression plasmid pUC18-PTPS (FIG. 4). The PTPS gene contained in pUC18-PTPS was transcribed by *Escherichia coli* lac promoter and the expressed PTPS had an amino acid sequence where 7 amino acids (underlined ones in FIG. 11) derived from pUC18 were added to amino terminus (FIG. 11).

3. Cloning of SPR (Sepiapterin Reductase) Gene Derived from Rat

According to the same method as in the case of cDNA containing PTPS gene, there was prepared cDNA containing SPR gene (Citron, B. A., et al. *Proc. Natl. Acad. Sci. USA* 87:6436-6440, 1990, [GenBank M36410] with an exception that sense primer P13 (SEQ ID NO: 13) and antisense primer P14 (SEQ ID NO: 14) were used for amplification of single stranded DNA containing SPR gene by means of a PCR. The cDNA containing SPR gene was used as a template and a PCR was carried out using sense primer P15 (SEQ ID NO: 15) and antisense primer P16 (SEQ ID NO: 16) to add the cleavage sites for the restriction enzymes BamHI and SpeI to the untranslated regions of 5'end and 3'end, respectively, of cDNA containing SPR gene. The PCR product was digested by BamHI and SpeI and inserted into the BamHI and SpeI sites of pProEX HTb vector (GIBCO BRL) to prepare pProEX-SPR (FIG. 5).

After that, a PCR was carried out for rat SPR gene using pProEX-SPR as a template and using sense primer P17 (SEQ ID NO: 17) and antisense primer P18 (SEQ ID NO: 18) to prepare SPR gene having the cleavage sites for a restriction enzyme HindIII at termini of 5'end and 3'end, respectively and the resulting PCR product was cleaved by a restriction enzyme HindIII and connected to HindIII fragment (2.7 kb) of pUC19 (Yanisch-Perron, C., Vieira, J. and Messing, J.

Figure 5:
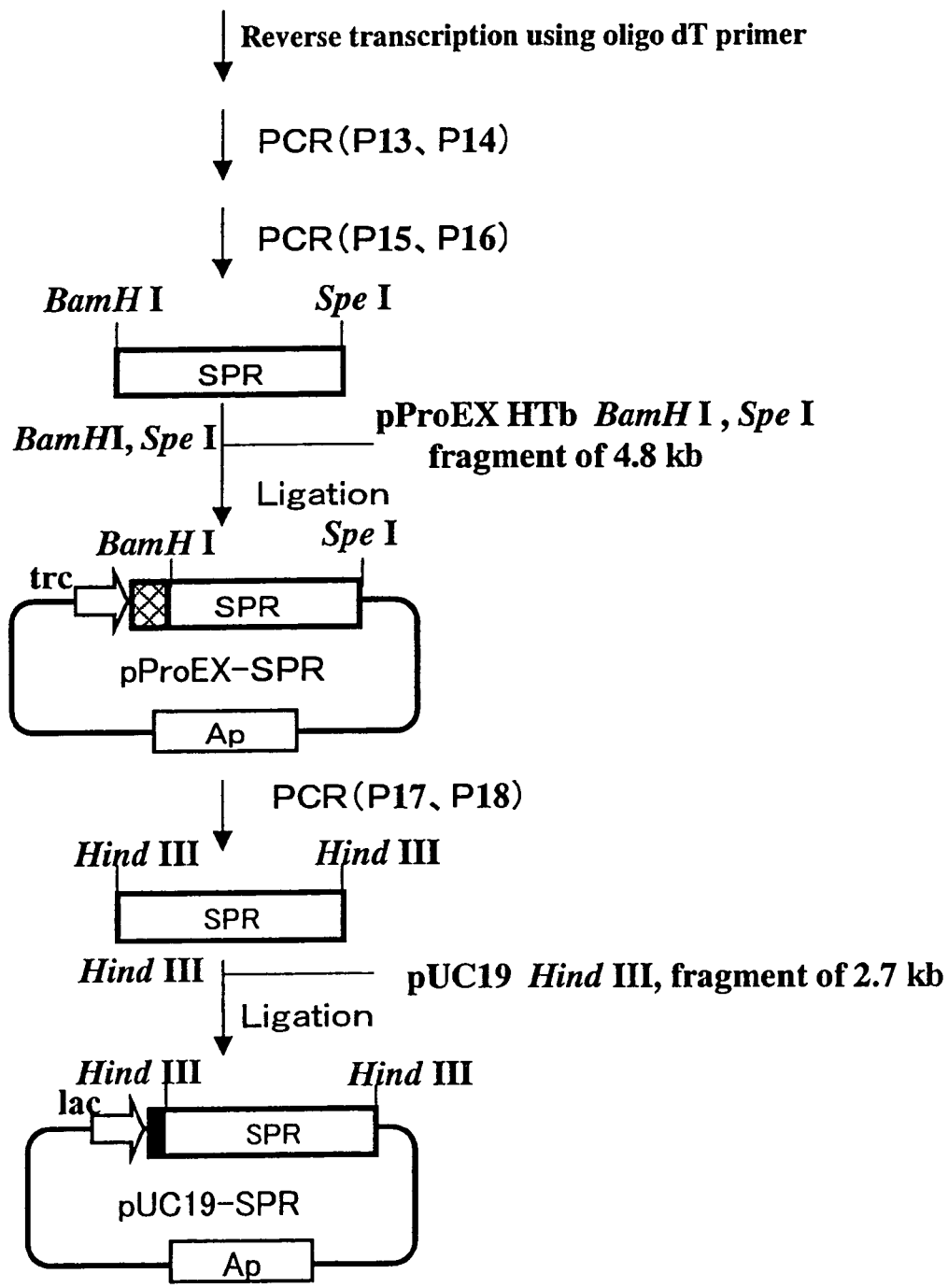
FIG. 5 shows the steps for preparation of pUC19-SPR. PCR (P13, P14) means a PCR using sense primer P13 and antisense primer P14. PCR(P15, P16) and PCR(P17, P18) have the similar meanings as well. Ap means ampicillin-resistant gene. trc means trc promoter and lac means lac promoter.

Gene, 33:103-119, 1985) to prepare a rat SPR expression plasmid pUC19-SPR (FIG. 5). With regard to SPR gene coded to pUC19-SPR, it was also transcribed by *Escherichia coli* lac promoter and the expressed SPR had an amino acid sequence where 8 amino acids (the underlined one in FIG. 12) derived from pUC19 were added to amino terminus (FIG. 12).

4. Cloning of GCH Gene (FOL 2) Derived from Yeast

Figure 6:
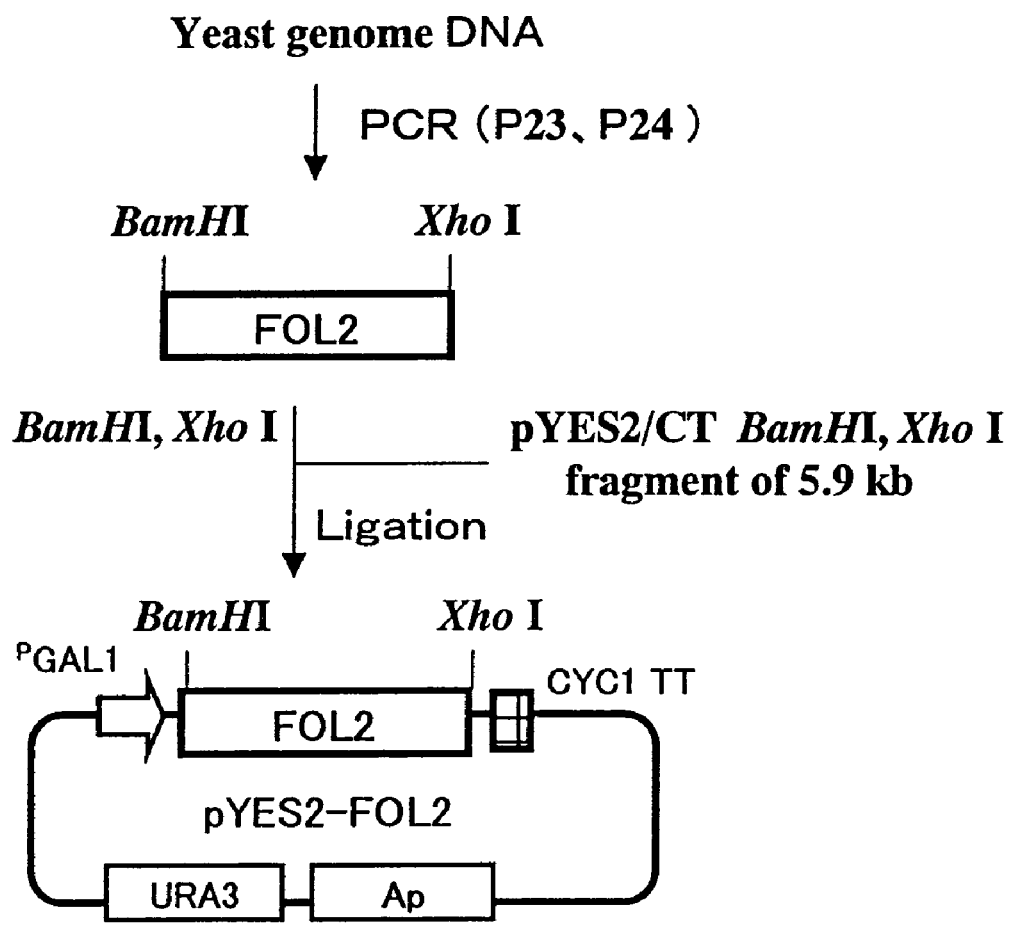
FIG. 6 shows the steps for preparation of pYES2-FOL2. PCR (P23, P24) means a PCR using sense primer P23 and antisense primer P24. Ap means ampicillin-resistant gene and URA3 means a selective marker in yeast. $^P$GAL1 means GAL1 promoter and CYC1 TT means transcription termination signal of CYC1 gene.

FOL2 is a homolog of GCH. A PCR was carried out using genomic DNA of yeast (*Saccharomyces cerevisiae*, KA31 strain) as a template and using sense primer P23 (SEQ ID NO: 23) and antisense primer P24 (SEQ ID NO: 24) to give DNA containing FOL2 gene (Tettelin, H., et al. *Nature* 387:81-84, 1997, [GenBank NC_001139]) having the cleavage sites for restriction enzymes BamHI and XhoI of the untranslated region at the 5'end and 3'end, respectively. The PCR product was digested by BamHI and XhoI and inserted into the BamHI and XhoI sites of pYES2/CT vector (Invitrogen) to prepare pYES2-FOL2 (FIG. 6).

Example 2

Preparation of Plasmid pSTV28-GPS Producing the Biopterin Compound for *Escherichia coli* pSTV28-GPS which is a THBP synthase expression plasmid for *Escherichia coli* was prepared by the following method. Firstly, a PCR was carried out using pUC18-PTPS mentioned in Example 1 as a template to amplify DNA containing from lac promoter to termination codon of PTPS gene. In designing the primer for the PCR, SalI site was provided to sense primer while BamHI site was provided to antisense primer so as to make the cloning thereafter easy. Those primers had sequences of sense primer P19 (SEQ ID NO: 19) and antisense primer P20 (SEQ ID NO: 20), respectively. The resulting PCR product was subjected to a precipitating treatment with ethanol, dissolved in a TE buffer (10 mM Tris-HCl (pH 8.0), 1 mM EDTA) and cleaved by restriction enzymes SalI and BamHI.

After that, a PCR was carried out using pUC19-SPR mentioned in Example 1 as a template to amplify the DNA containing from lac promoter to termination codon of SPR gene. In the primers for the PCR, BamHI site was provided to sense primer while SphI site was provided to antisense primer. Those primers had a sequence of sense primer P21 (SEQ ID NO: 21) and that of antisense primer P22 (SEQ ID NO: 22), respectively. The resulting PCR product was subjected to a precipitation treatment with ethanol, dissolved in a TE buffer (10 mM Tris-HCl (pH 8.0) and 1 mM EDTA) and cleaved by restriction enzymes BamHI and SphI.

Figure 7:
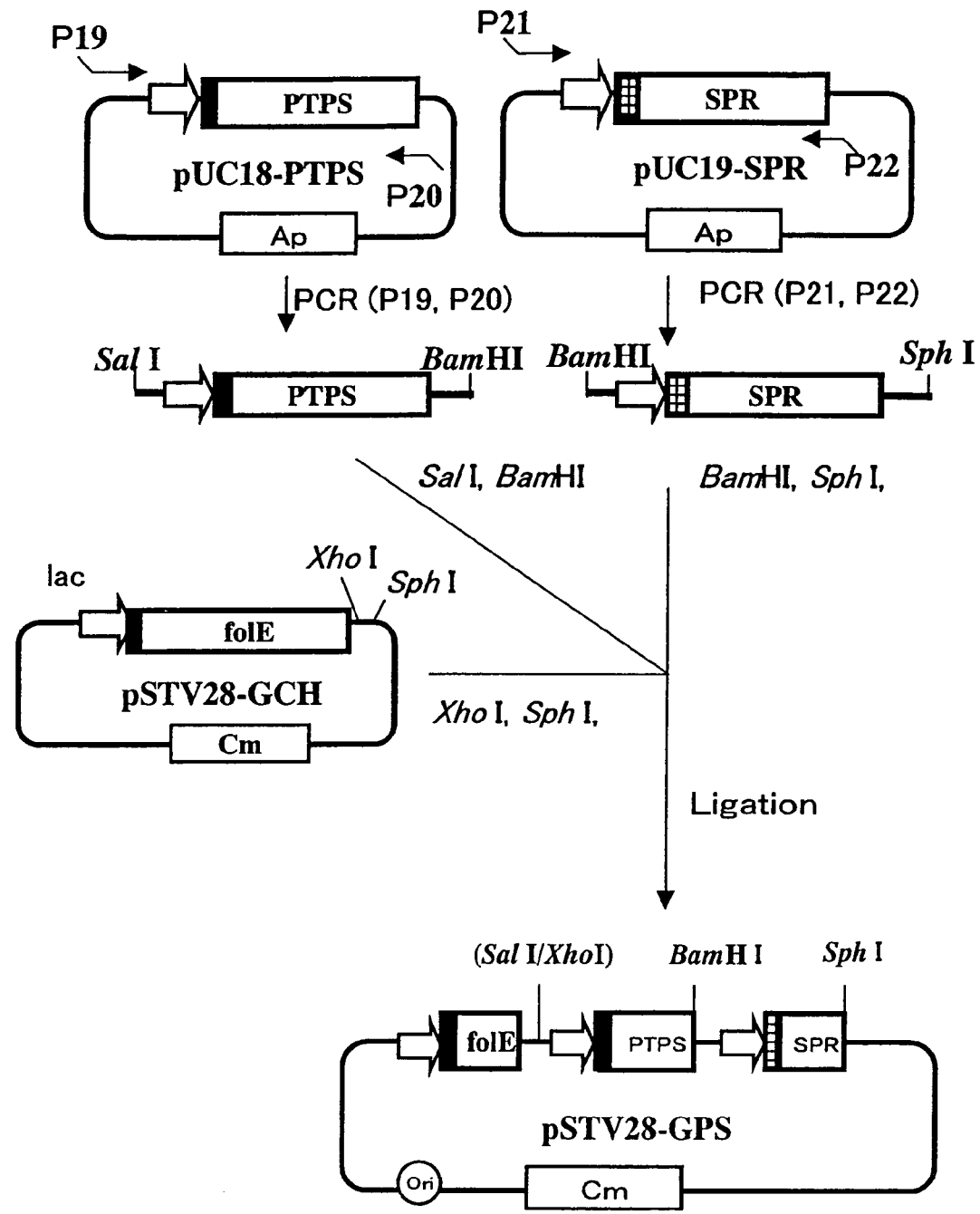
FIG. 7 shows the steps for preparation of pSTV28-GPS. PCR (P19, P20) means a PCR using sense primer P19 and antisense primer P20. PCR(P21, P22) has the similar meaning as well. Ap means ampicillin-resistant gene and Cm means chloramphenicol-resistant gene. lac means lac promoter. Ori means origin of replication.

The SalI-BamHI fragment containing PTPS gene and BamHI-SphI fragment containing SPR gene prepared as such were connected to digested product (3.9 kb) of pSTV28-GCH by XhoI and SphI to prepare pSTV28GPS (FIG. 7). The pSTV28-GPS has a structure where each of GCH, PTPS and SPR genes (described in FIG. 10 to FIG. 12) is transcribed by lac promoter.

Example 3

Preparation of pYES2-FPS, a Plasmid Producing the Biopterin Compound for Yeast

A PCR was carried out using sense primer P25 (SEQ ID NO: 25) and antisense primer P26 (SEQ ID NO: 26) where pUC18-PTPS was used as a template to add the cleavage sites for restriction enzymes BamHI and XhoI to the untranslated region at 5'end and 3'end, respectively, of PTPS gene. The PCR product was digested by BamHI and XhoI and inserted into BamHI and XhoI sites of pYES2/CT vector to prepare pYES2-PTPS (FIG. 8).

After that, a PCR was carried out using sense primer P27 (SEQ ID NO: 27) and antisense primer P28 (SEQ ID NO: 28) where pUC19-SPR was used as a template to prepare cDNA containing SPR gene having the cleavage sites for restriction enzymes BamHI and XhoI at the untranslated region at 5'end and 3'end, respectively, of SPR gene. The PCR product was digested by BamHI and XhoI and inserted into the BamHI and XhoI sites of pYES2/CT vector (Invitrogen) to prepare pYES2-SPR (FIG. 8).

Figure 9:
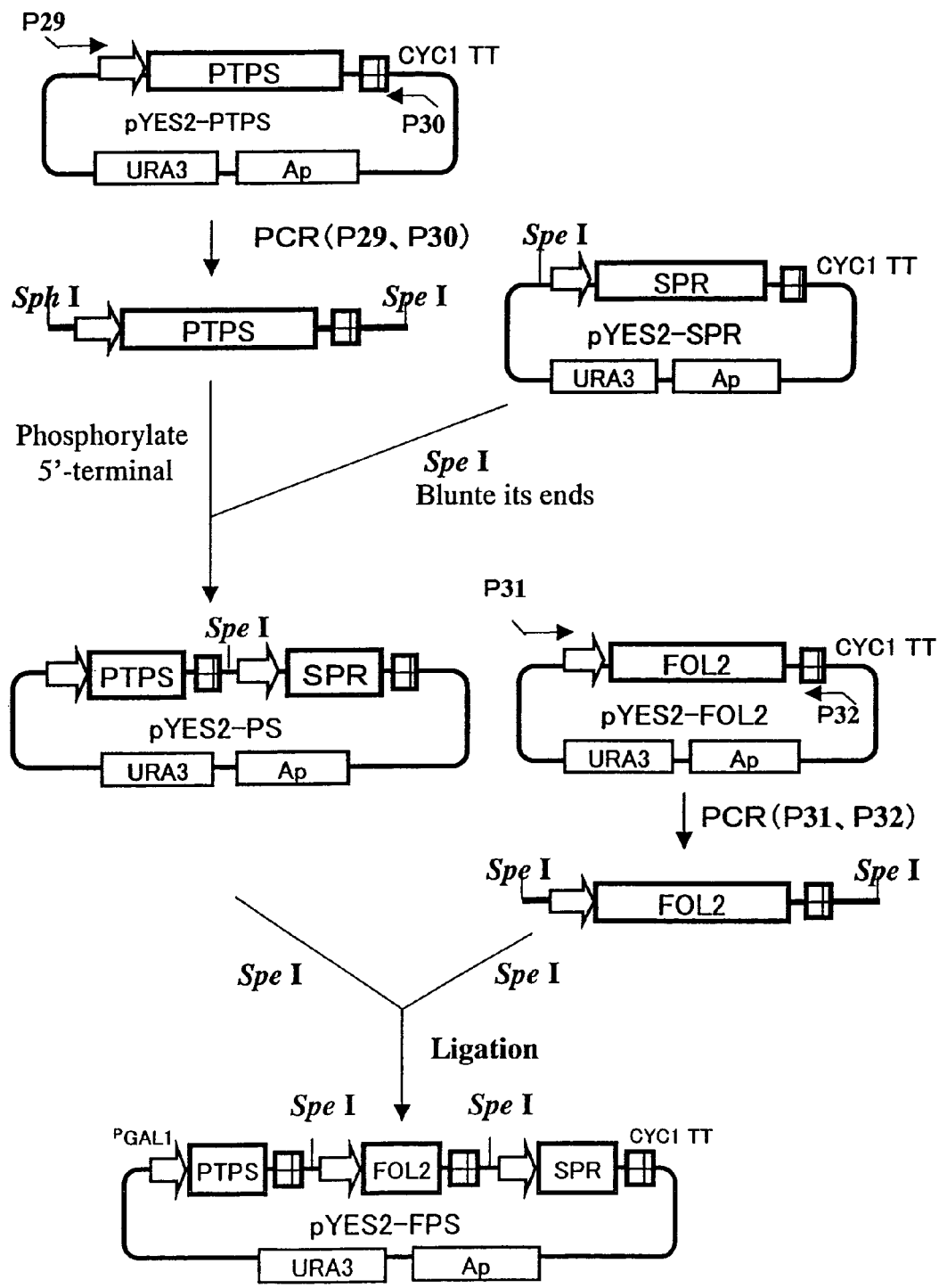
FIG. 9 shows the steps for preparations of pYES2-FPS. PCR (P29, P30) means a PCR using sense primer P29 and antisense primer P30. PCR(P31, P32) has the similar meaning as well. Ap means ampicillin-resistant gene and URA3 means a selective marker in yeast. $^P$GAL1 means GAL1 promoter and CYC1 TT means transcription termination signal of CYC1 gene.

Then a PCR was carried out using sense primer P29 (SEQ ID NO: 29) and antisense primer P30 (SEQ ID NO: 30) where pYES2-PTPS was used as a template to prepare DNA fragment having GAL1 promoter to which the cleavage site for SphI was added at upper stream of PTPS gene and CYC1 transcription termination signal to which the cleavage site for SpeI was added at downstream. Incidentally, this DNA fragment has blunt ends because of the property of DNA polymerase (pyrobest DNA Polymerase [Takara Shuzo]) used therefor. The said DNA fragment where the 5'terminus was phosphorylated was inserted into pYES2-SPR where its ends were blunted after being digested by SpeI to prepare pYES2-PS. After that, a PCR was carried out using sense primer P31 (SEQ ID NO: 31) and antisense primer P32 (SEQ ID NO: 32) where pYES2-FOL2 was used as a template to prepare DNA fragment having GAL1 promoter to which the cleavage site for SpeI was added at upper stream of FOL2 gene and CYC1 transcription termination signal to which the cleavage site for SpeI was added at downstream. The fragment was digested by SpeI and inserted into the cleavage site for SpeI of pYES2-PS to prepare pYES2-FPS. In the pYES2-FPS, it had a structure where each of GCH gene derived from *S. cerevisiae*, PTPS gene derived from rat and SPR gene derived from rat is transcribed by GALL promoter and enzyme having the same amino acid sequence as the enzyme of a natural type is expressed (FIG. 9).

Example 4

Production of the Biopterin Compound by *Escherichia coli*

*Escherichia coli* JM101 strain was transformed using pSTV28-GPS by a calcium chloride method (Mandel and Higa, *J. Mol. Biol.*, 53, 159-162, 1970) and the resulting JM101/pSTV28-GPS was cultured to investigate its ability of production of the biopterin compound. Firstly, JM101/pSTV28-GPS cultured for one night in an LB medium was used as a pre-culture broth, 50 µl thereof were inoculated in 3 mL of an NUCA medium containing 0.5 mM IPTG (isopropyl thiogalactopyranoside) and cultured at 37° C. for 48 hours. Incidentally, the LB medium and NUCA medium comprised the following compositions. Thus, [composition in 1 L of the LB medium: 10 g of tryptone, 5 g of yeast extract and 5 g of NaCl] and [composition in 1 L of NUCA medium: 20 g of glycerol, 4 g of yeast extract, 10 g of Casamino acid, 4 g of $K_2HPO_4$, 4 g of $KH_2PO_4$, 2.7 g of $Na_2HPO_4$, 1.2 g of $(NH_4)_2SO_4$, 0.2 g of $NH_4Cl$, 2 g of $MgSO_4.7H_2O$, 40 mg of $FeSO_4.7H_2O$, 40 mg of $CaCl_2.2H_2O$, 10 mg of $MnSO_4.nH_2O$, 10 mg of $AlCl_3.6H_2O$, 4 mg of $CoCl_2.6H_2O$, 2 mg of $ZnSO_4.7H_2O$, 2 mg of $Na_2MoO_4.2H_2O$, 1 mg of $CuCl_2.7H_2O$, 0.5 mg of $H_3BO_4$ and 30 mg of chloramphenicol].

Figure 13:
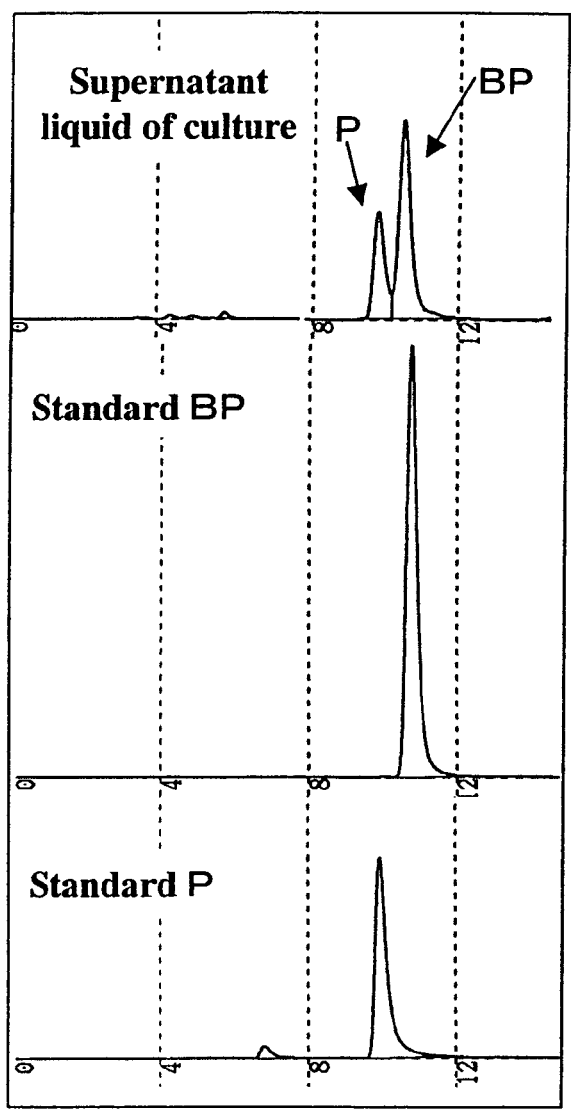
FIG. 13 shows the result of HPLC analysis of culture supernatant of biopterin compound producing *Escherichia coli* JM101/pSTV28-GPS by a C18 reversed column.

The resulting THBP is easily oxidized in its aqueous solution to give DHBP and BP and, in order to check whether JM101/pSTV28-GPS produced the THBP, the culture broth was subjected to an iodine oxidization to convert to BP and the produced amount thereby was measured. The culture broth was centrifuged to remove the cells, one-tenth by volume of potassium iodide solution (1N hydrochloric acid solution containing 0.9% of I2 and 1.8% of KI) was added to the culture broth and the mixture was allowed to stand for 1 hour shielding the light. Then this culture broth was diluted to 20-fold with deionized water, injected to a C18 reversed phase column (COSMOSIL 5C18-AR, Nakarai Tesk) of 4.6 mm×250 mm equilibrated with 10 mM sodium phosphate buffer at a flow rate of 0.8 mL/minute and BP was quantified by exciting at 350 nm using a 440 nm fluorescent detector. As a result, peaks corresponding to standard BP specimen and standard P (pteridine) specimen were detected in the supernatant (FIG. 13) whereby it was apparent that JM101/pSTV28-GPS produced the biopterin compound. When the amount of the biopterin compound was calculated from the peak areas, the production amount per liter of the culture broth was about 20 mg.

Example 5

Production of Biopterin Compound by Yeast

*S. cerevisiae* KA31 strain (MATaura3 leu2 his3 trp1) was transformed by a lithium acetate method using pYES2-FPS. The transformed cell was selected by an SD-Ura⁻ medium to give an FPS strain. [Composition in 1 liter of the SD-Ura⁻ medium: 20 g of glucose, 1.7 g of yeast nitrogen base (containing neither amino acid nor ammonium sulfate), 5 g of ammonium sulfate, 20 mg of adenine sulfate, 20 mg of Arg, 100 mg of Asp, 100 mg of Glu, 30 mg of Ile, 30 mg of Lys, 20 mg of Met, 50 mg of Phe, 400 mg of Ser, 200 mg of Thr, 30 mg of Tyr, 150 mg of Val, 20 mg of His, 100 mg of Leu and 20 mg of Trp].

Similarly was prepared a transformed cell by vector (pYES2/CT) as a control (Mock).

The resulting transformed cell was cultured in 5 ml of SCD-Ura⁻ medium until $OD_{600\,nm}$ became 0.4 and, after that, it was substituted to the same amount of an SCGal-Ura⁻ medium to conduct expression induction. Incidentally, the incubating temperature was made 30° C.

Composition in 1 liter of the SCD-Ura medium: 1.7 g of yeast nitrogen base (containing neither amino acid nor ammonium sulfate), 5 g of ammonium sulfate, 5 g of Casamino acid, 20 g of glucose, 20 mg of adenine sulfate and 20 mg of Trp.

Composition in 1 liter of the SCGal-Ura⁻ medium: 1.7 g of yeast nitrogen base (containing neither amino acid nor ammonium sulfate), 5 g of ammonium sulfate, 5 g of Casamino acid, 20 g of galactose, 20 mg of adenine sulfate and 20 mg of Trp.

After 24 hours from the expression induction, yellow coloration which was specific to the pteridine compound was noted in the culture broth of the FPS strain whereby it was noted from the appearance that the expressed three kinds of enzymes functioned in the cells.

Figure 14:
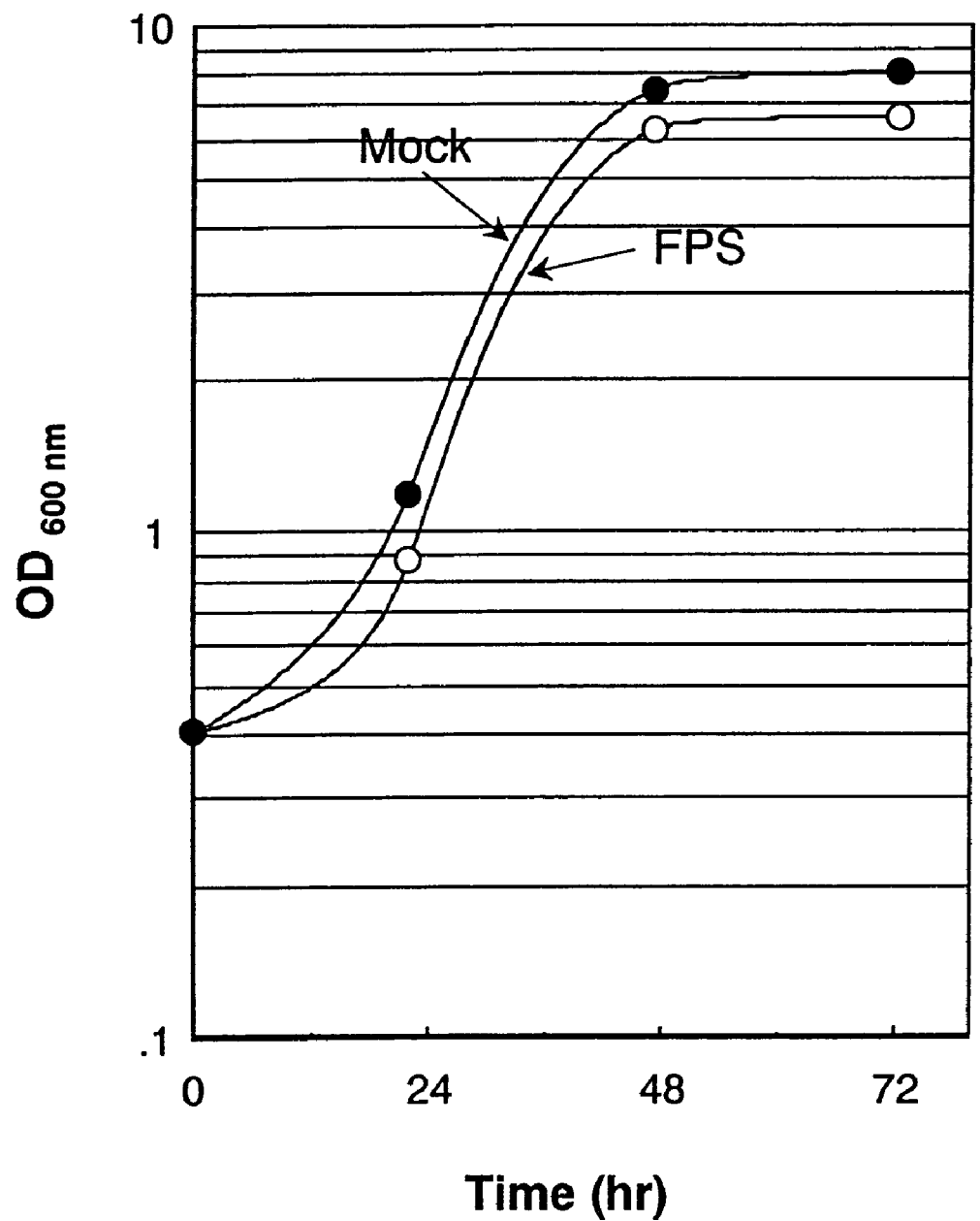
FIG. 14 shows growth curves of biopterin compound-productive yeast (FPS strain).

Growth of the cells after the induction was good in both FPS strain and Mock strain (FIG. 14). In order to confirm the production of THBP or its oxidized product, the culture supernatant after 72 hours from the induction was oxidized as same as in Example 4 and subjected to HPLC analysis and TLC analysis.

Incidentally, the HPLC analysis was carried out by the same method as in Example 4. In the TLC analysis, a thin layer plate of silica gel for thin layer chromatography (silica gel 60 $F_{254}$; layer thickness: 0.25 mm; 10 cm×20 cm) was used and, as to a developing solvent, a mixture of chloroform, methanol, acetic acid and water (45:10:5:2) was used. The sample (20 μl) and each 100 ng of standard BP and P specimens were spotted onto the thin layer plate, dried with air and developed by an inclined ascending method. When the developed distance became about 12 cm, development was finished, the thin layer plate was dried with air and irradiated with ultraviolet ray (main wavelength: 254 nm) and the absorption spot was detected.

Figure 15:
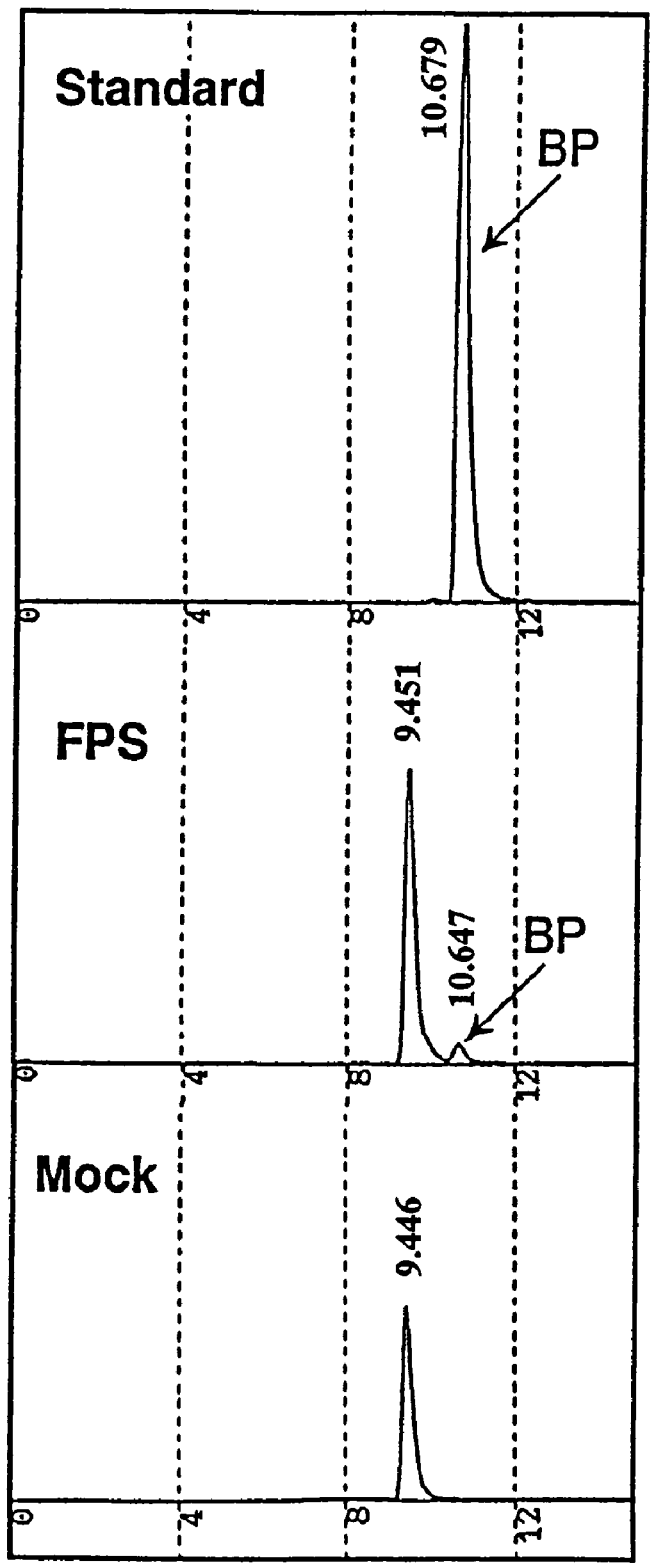
FIG. 15 shows the result of HPLC analysis of culture supernatant of biopterin compound producing yeast (FPS strain) by a C18 reversed column.

Result of the HPLC analysis is shown in FIG. 15. Only in the FPS strain, the peak corresponding to BP was noted and, from the area ratio of peak areas, it was found that the FPS strain produced the biopterin compound corresponding to 0.76 μg/ml of BP by induction for 72 hours in the culture supernatant.

Figure 16:
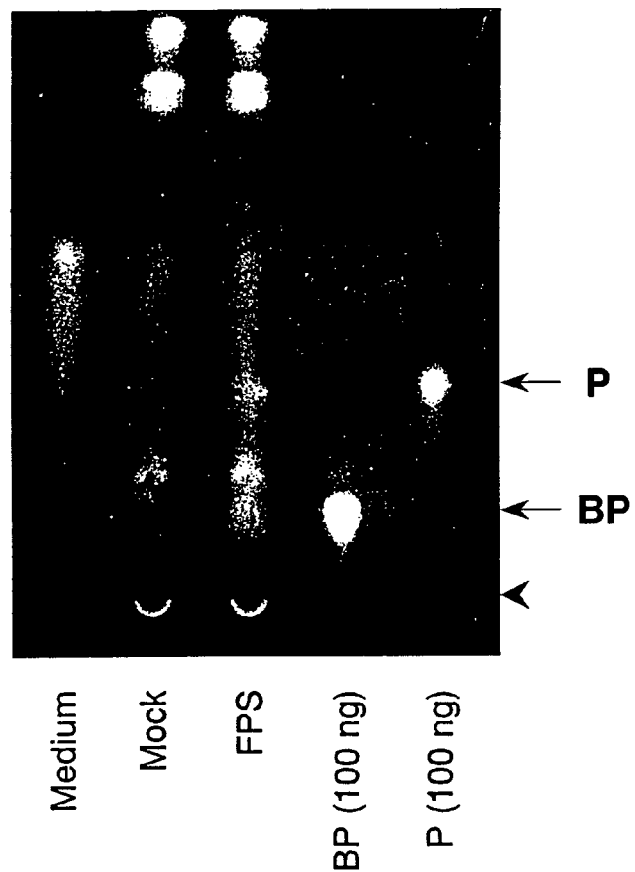
FIG. 16 shows the result of TLC analysis of culture supernatant of biopterin compound producing yeast (FPS strain).

FIG. 16 shows the result of the TLC analysis of the culture supernatant. In the culture supernatant of the FPS strain, a spot showing the same mobility as the standard BP specimen was confirmed. In the TLC analysis, it was found that, when 20 μl of the culture supernatant oxidized with potassium iodide as mentioned in Example 5 were analyzed, 1.37 μg of BP were produced per 20 μl of the culture supernatant upon calculation from the ultraviolet absorption intensity of the spot of BP and that value is identical with the value calculated from the result of the HPLC analysis which was 0.76 μg per ml of the culture supernatant.

Example 6

Preparation of *Escherichia coli* Producing the Biopterin Compound

In order to prepare a host bacterium being able to produce GTP which is a precursor of THBP in more quantities than the wild type, a regulatory mutant for synthesis of purine was prepared as follows.

Firstly, in an M9 minimum agar medium containing 20, 50, 100 and 500 μg/ml of 8-azaguanine and decoynine, sensitivity of those substances to *Escherichia coli* JM101 was tested and it became clear that the sensitivity was available to 100 μg/ml or more 8-azaguanine and to 500 μg/ml or more decoynine.

Composition of the M9 minimum agar medium: 2 g/L of glucose, 6 g/L of $Na_2HPO_4$, 3 g/L of $KH_2PO_4$, 0.5 g/L of NaCl, 1 g/L of $NH_4Cl$, 2 mM of $MgSO_4$, 0.1 mM of $CaCl_2$ and 15 g/L of agar; pH 7.4.

Then, *Escherichia coli* JM101 which was mutated by N-methyl-N-nitro-nitrosoguanidine (Miller, 1972, Experiments in Molecular Genetics, Cold Spring Harbor Laboratory, Cold Spring Harbor, N.Y.) was sowed on a plate of the M9 minimum agar medium containing 100 μg/ml of 8-azaguanine or 500 μg/ml of decoynine and incubated at 37° C. to give a resistant mutant. From each of the resistant mutant strains, 50 strains each were selected and expression plasmid pSTV28-GPS was introduced thereinto by a calcium chloride method. The strain prepared as such was cultured for 48 hours in the above-mentioned NUCA medium and the amount of the biopterin compound produced by each strain was compared.

Figure 17:
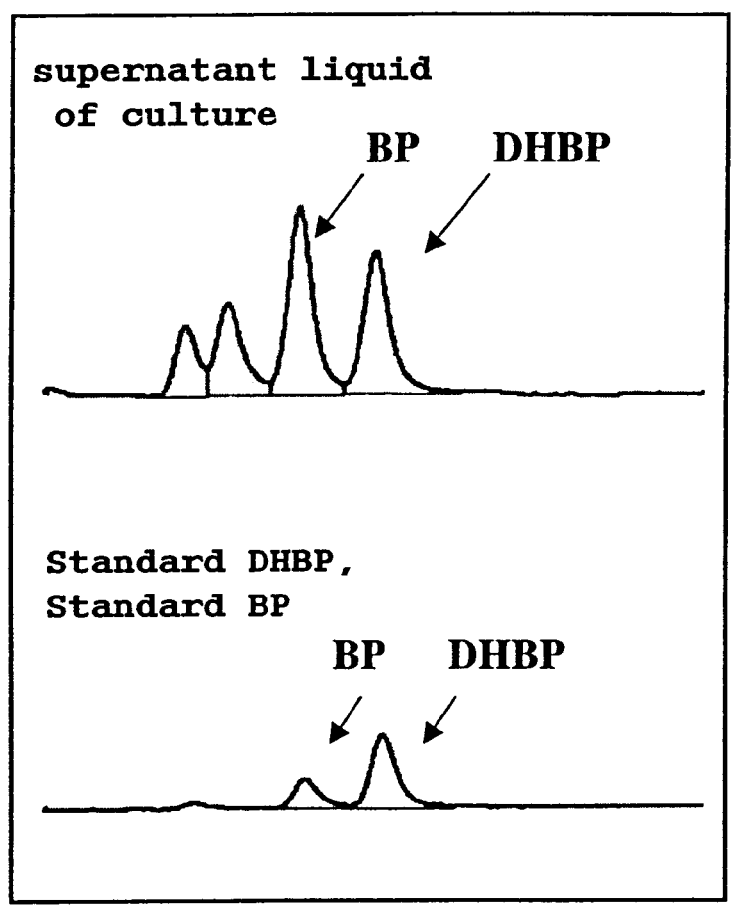
FIG. 17 shows the result of HPLC analysis of culture supernatant of biopterin compound producing *Escherichia coli* AG14/pSTV28-GPS by a C18 reversed column.

As a result, among the 8-azaguanine-resistant strains, there was obtained an AG14/pSTV28-GPS strain having a productivity of the biopterin compound of about 10-fold as compared with the parent strain (JM101/pSTV28-GPS). Thus, it became clear that, when 8-azaguanine resistance is given to *Escherichia coli*, a strain where the productivity of the biopterin compound increased was able to be prepared (Table 1). Incidentally, it became clear that, with regard to this strain, DHBP was detected in the culture broth in addition to BP and that a part of the produced THBP was naturally oxidized being present as DHBP or BP (FIG. 17).

Example 7

Culture of *Escherichia coli* Producing the Biopterin Compound Using a Jar Fermenter and Purification of BP A bacterium AG14/pSTV28-GPS strain being able to produce the biopterin compound was cultured using a 3-liter jar fermenter. As a medium for the jar fermenter, the above-mentioned NUCA medium containing 0.5 mM of IPTG was used. Firstly, the AG14/pSTV28-GPS strain was cultured in an LB medium for one night, 10 ml thereof were inoculated on 2 L of the NUCA medium containing 0.5 mM of IPTG and cultured at 37° C. while the level of dissolved oxygen was kept at 30%. After 2% of glycerol added in the initial stage of the culture was consumed, 80% glycerol was added successively and the cultivation was carried out for 48 hours.

An HPLC analysis was carried out for a part of the culture broth. Thus, the produced THBP was converted by oxidizing with potassium iodide solution as same as in Example 4 and analysis was conducted by means of fluorescent analysis using an HPLC. The HPLC was carried out as same as in Example 5. The result was that, when determined from the produced amount of BP calculated from the peak area, it was found that 350 mg/L of THBP was produced by the culture for 48 hours.

In order to obtain the BP from the resulting culture broth, 200 ml of the above culture broth were centrifuged to remove the cells and one-tenth of potassium iodide solution (1N hydrochloric acid solution containing 0.9% of $I_2$ and 1.8% of KI) was added to the supernatant so as to oxidize to BP. After that, the mixture was allowed to stand for 1 hour shielding the light and adjusted to pH 7.0 by adding 5M aqueous solution of sodium hydroxide thereto. Then the solution was cooled with ice so that BP was separated out and precipitated, the resulting precipitate was recovered by centrifugation, pure water was added thereto and the mixture was adjusted to pH 2 with hydrochloric acid whereby the precipitate was dissolved. This solution was charged to a column of Dowex 1×8 (10 mm×100 mm), washed with 20 ml of pure water and eluted with 0.5 M NaCl at a flow rate of 1 ml/minute. Every 2 ml of the resulting eluate were collected and the 8th to the 16th fractions were pooled. One half of the pooled fractions was charged to a column (10 mm×100 mm) of Florisil equilibrated with 0.5 M formic acid, washed with 20 ml of 0.5 M formic acid and eluted with 2N HCl. Every 1.8 ml of the resulting eluate were collected and the 4th to the 16th fractions were pooled whereby 2 mg of BP of 98% purity were obtained.

Example 8

Optimization of Culture Condition and Increase in the Producing Amount of the Biopterin Compound In the culture using the three-liter jar fermenter mentioned in Example 17, culture was carried out where incubating temperature, pH of medium and level of dissolved oxygen were controlled to predetermined ones. Those conditions were as follows.

Figure 18:
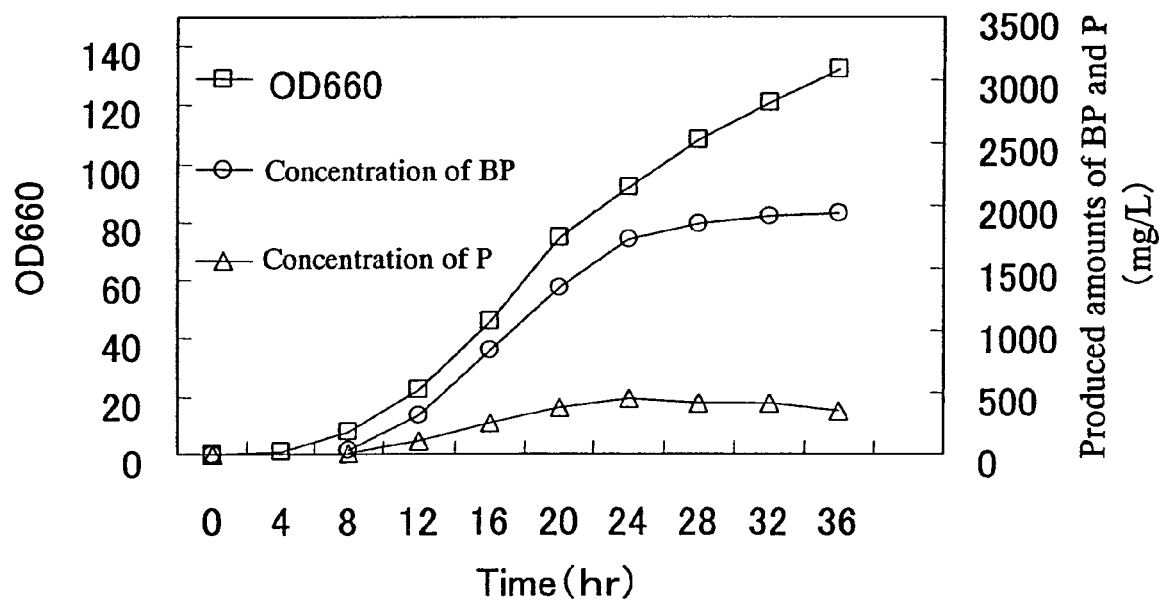
FIG. 18 shows the time course of BP and P production by *E. coli* AG14/pSTV28-GPS and the time course of OD660 of culture broth.

(1) Cultivation temperature is 37° C.
(2) ph value is 6.5.
(3) Dissolved oxygen level is 30%.

pH of the medium was controlled by addition of 28% aqueous ammonia, while dissolved oxygen level was controlled by an increase of revolution upon stirring. With regard to glycerol which is a carbon source, 2% were added at the start of the culture and, after consumption, 80% glycerol were continuously added at the flow rate of 10 ml/hour. As a result, it was found that 2 g/L of THBP were produced upon culture for 48 hours when determined from the produced amount of BP calculated from the peak area of the HPLC analysis (FIG. 18).

Example 9

Figure 19:
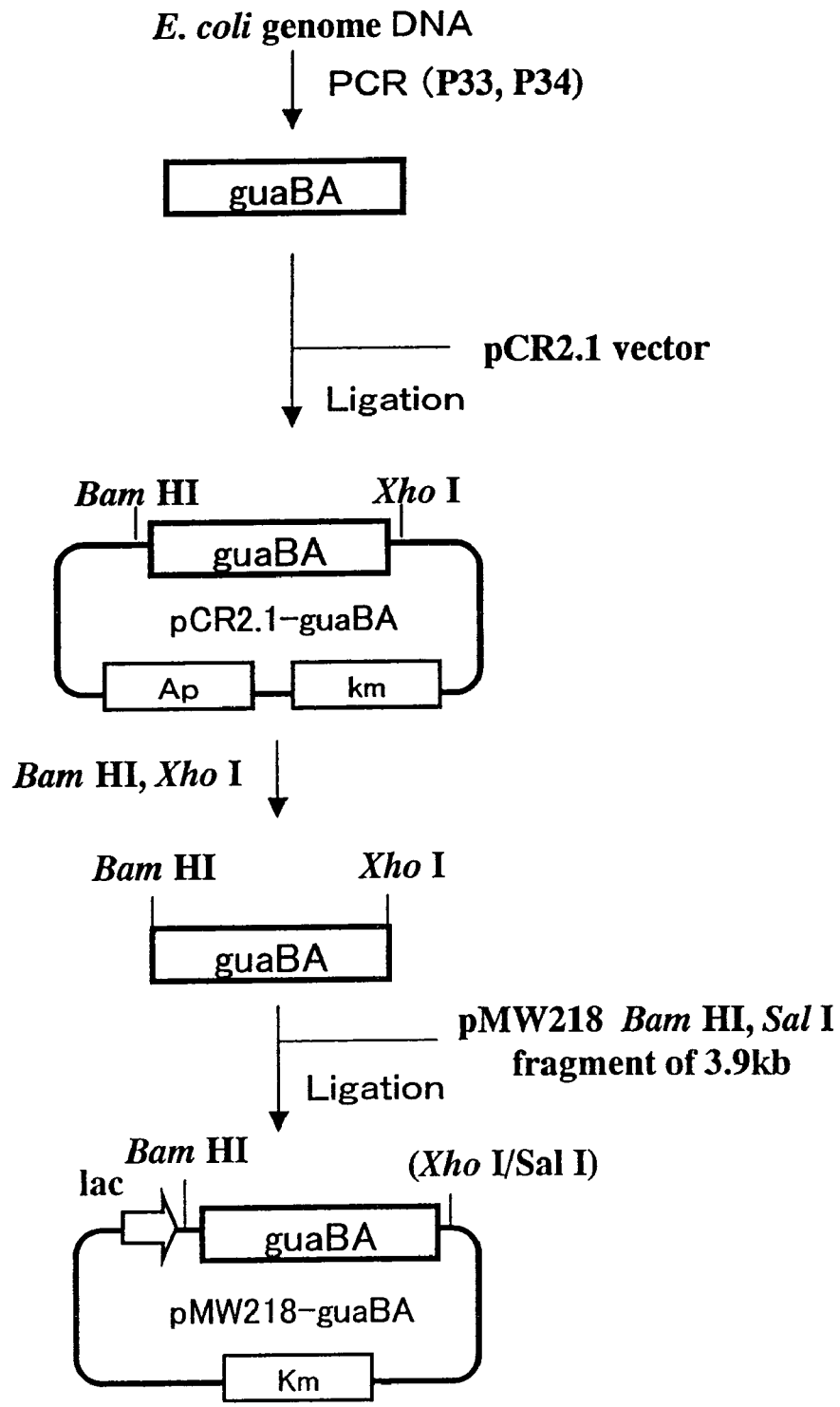
FIG. 19 shows the steps for preparation of pMW218-guaBA. PCR(P33, P34) means a PCR using sense primer P33 and antisense primer P34. Ap means ampicillin-resistant gene and km means kanamycin-resistant gene. lac means lac promoter.

Increase in the Produced Amount of the Biopterin Compound by Increased Expression of guaBA Gene Cloning of guaBA gene (Tiedeman, A. A., et al., *J. Biol. Chem.* 260:8676-8679, 1985 and *Nucleic Acids Res.* 13:1303-1316, 1985 [GenBank M10101]) was carried out from *Escherichia coli* (W 3110 strain) genomic DNA by a PCR. *Escherichia coli* (W 3110 strain) genomic DNA was prepared by a reported method (*Seibutsu Kogaku Jikkensho* [published by Baifukan, p. 97-98]). A PCR was carried by a conventional manner using sense primer P 33 (SEQ ID NO: 33) and antisense primer P 34 (SEQ ID NO: 34) to prepare DNA containing *Escherichia coli* guaBA gene. Then the resulting guaBA gene was subcloned to vector pCR2.1 (Invitrogen) to prepare pCR2.1-guaBA. After that, pCR2.1-guaBA was cleaved by BamHI and XhoI and a fragment of 3 kb containing guaBA gene was inserted into BamHI and XhoI fragments (3.9 kb) of pMW218 (Nippon Gene) to prepare pMW218-guaBA (FIG. 19). This plasmid was introduced into AG14/pSTV28-GPS strain by a calcium chloride method to prepare AG14/(pSTV28-GPS, pMW218-guaBA). Selection and culture of the transformed strain were carried out in a medium containing kanamycin (25 µg/ml) and chloramphenicol (25 µl/ml). The prepared strain was cultured by a method mentioned in Example 4 and the produced amount was measured from the peak area by an HPLC analysis whereupon 580 mg/L of BP were found to be produced (Table 1).

Example 10

Increase in Produced Amount of the Biopterin Compound due to Increase in Expressed Amount of GCH pSTV28-GCH and pUC18-PTPS were treated with EcoRI and SalI to isolate folE gene and rat PTPS gene and each of them was inserted into EcoRI and SalI sites existing in a multi-cloning sites of pTWV228 (Takara Shuzo) to prepare pTWV228-GCH and pTWV228-PTPS. Similarly, pUC19-SPR was treated with HindIII to isolate rat SPR gene and inserted into HindIII existing in a multi-cloning site of pTWV229 (Takara Shuzo) to prepare pTWV229-SPR. Each of the three plasmids prepared as such was introduced into AG14/(pSTV28-GPS, pMW218-guaBA) strain and produced amount of the biopterin compound was measured by the method mentioned in Example 4. Selection and culture of the transformed strain were carried out in a medium containing ampicillin (25 µg/ml), kanamycin (25 µg/ml) and chloramphenicol (25 µg/ml).

Produced amounts of the prepared bacteria were 524 mg/L for AG14/(pSTV28-GPS, pMW218-guaBA, pTWV228-

GCH), 337 mg/L for AG14/(pSTV28-GPS, pMW218-guaBA, pTWV228-PTPS) and 465 mg/L for AG14/(pSTV28-GPS, pMW218-guaBA, pTWV229-SPR). As a result that the plasmid was newly introduced, an increase in the expressed amount of each enzyme was confirmed upon analysis by SDS-PAGE.

From the above result, it was found that, with regard to the three kinds of enzymatic genes participating in the THBP production, produced amount of the biopterin compound was able to be improved when its expressed amount was increased and that, particularly when the expressed amount of GCH gene was increased, produced amount of biopterin compound was able to be further improved.

Example 11

Increase in Production of the Biopterin Compound by Utilization of *Bacillus subtilis* GCH Gene (mtrA)

Cloning of mtrA (Gollnick, P., et al. *Proc. Natl. Acad. Sci. U.S.A.* 87:8726-8730, 1990, [GenBank M37320]) which was a *Bacillus subtilis* GCH gene was carried out from *Bacillus subtilis* 1A1 strain by a PCR. The *Bacillus subtilis* genomic DNA was prepared by a reported method (*Idenshi Hatsugen Jikken Manual* [Kodansha Scientific, p. 31-33]). A PCR was carried out by a conventional method using sense primer P35 (SEQ ID NO: 35) and antisense primer P 36 (SEQ ID NO: 36) to prepare the DNA containing *Bacillus subtilis* mtrA gene. After that, the resulting PCR product was used as a template and a PCR was carried out once again using sense primer P37 (SEQ ID NO: 37) and antisense primer P 38 (SEQ ID NO: 38) and the product was cleaved by EcoRI and XbaI and connected to a digested product of pUC18 by EcoRI-XbaI to prepare pUC18-mtrA.

Figure 20:
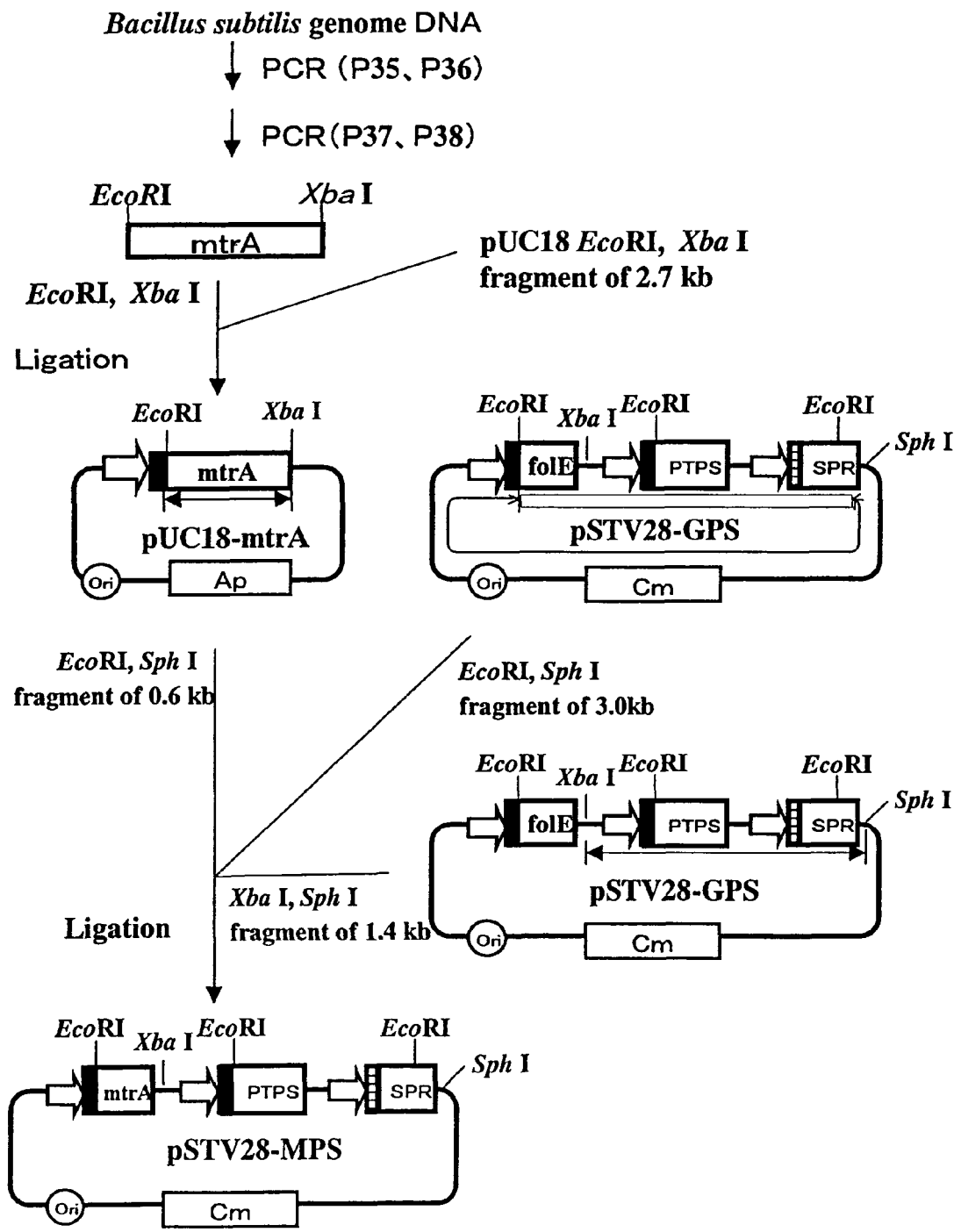
FIG. 20 shows the steps for preparation of pSTV28-MPS. PCR(P35, P36) means a PCR using sense primer P35 and antisense primer P36. PCR(P37, P38) has the similar meaning as well. Ap means ampicillin-resistant gene and km means kanamycin-resistant gene. Ori means origin of replication.

After that, mtrA gene was excised from pUC18-mtrA by EcoRI and XbaI and they were connected to a fragment made by digestion of pSTV28-GPS with EcoRI and SphI (3.0 kb) and a fragment made by digestion of pSTV28-GPS with XbaI and SphI (1.4 kb) to prepare pSTV28-MPS (FIG. 20). Then AG14/pMW218-guaBA strain was transformed by the resulting pSTV28-MPS to prepare AG14/(pSTV28-MPS, pMW218-guaBA) and the produced amount of THBP was measured by the method mentioned in Example 4. Cultivation was carried out in a medium containing kanamycin (25 µg/ml) and chloramphenicol (25 µg/ml). As a result, the strain [AG14/(pSTV28-MPS, pMW218-guaBA)] having the GCH gene of *Bacillus subtilis* showed high produced amount of THBP (770 mg/L) and it was found that, when the GCH gene (mtrA) of *Bacillus subtilis* was used, produced amount of the biopterin compound further increased (Table 1).

TABLE 1

| Strain | THBP Production [Detected as BP] |
|---|---|
| JM101/pSTV28-GPS | 23 mg/L |
| AG14/pSTV28-GPS | 250 mg/L |
| AG14/(pSTV28-GPS, pMW218-guaBA) | 580 mg/L |
| AG14/(pSTV28-MPS, pMW218-guaBa) | 770 mg/L |

Example 12

Figure 21:
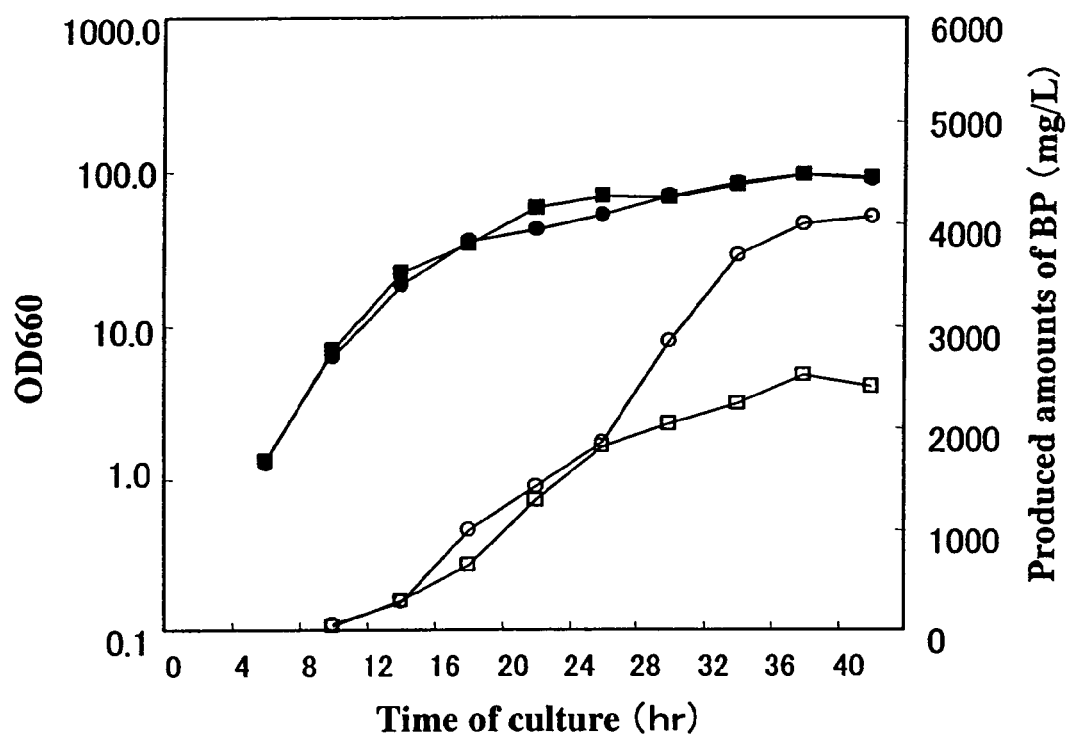
FIG. 21 shows the time course of BP production by *E. coli* AG14/(pSTV28-GPS, pMW218-guaBA) and AG14/(pSTV28-MPS, pMW218-guaBA) and the time course of OD660 of culture broth. In the drawing, ■ shows changes with a lapse of time of OD660 for AG14/(pSTV28-GPS, pMW218-guaBA); ● shows changes with a lapse of time of OD660 for AG14/(pSTV28-MPS, pMW218-guaBA); □ shows changes with a lapse of time of produced amount of BP for AG14/(pSTV28-GPS, pMW218-guaBA); and ○ shows changes with a lapse of time of produced amount of BP for AG14/(pSTV28-MPS, pMW218-guaBA).

Culture of Strain with Increased guaBA Expression and Strain Carrying GCH Homologue Gene Derived from *Bacillus subtilis* by Jar Fermenter AG14/(pSTV28-GPS,pMW218-guaBA) which was a strain with increased guaBA expression and AG14/(pSTV28-MPS,pMW218-guaBA), in which GCH gene from *Bacillus subtilis* was introduced, were subjected to a two-liter scale cultivation according to a method mentioned in Examples 7 and 8. As a result, BP calculated from the peak area in the HPLC analysis was produced in an amount of 2.4 g/L in the case of AG14/(pSTV28-GPS,pMW218-guaBA) and in an amount of 4 g/L in the case of AG14/(pSTV28-MPS, pMW218-guaBA) by a culture for 42 hours (FIG. 21).

Example 13

Preparation of Expression Vectors pDG148MPS and pDG148MPSΔI for *Bacillus subtilis*

Expression vectors pDG148MPS and pDG148MPSΔI for *Bacillus subtilis* were prepared as follows.

Figure 22:
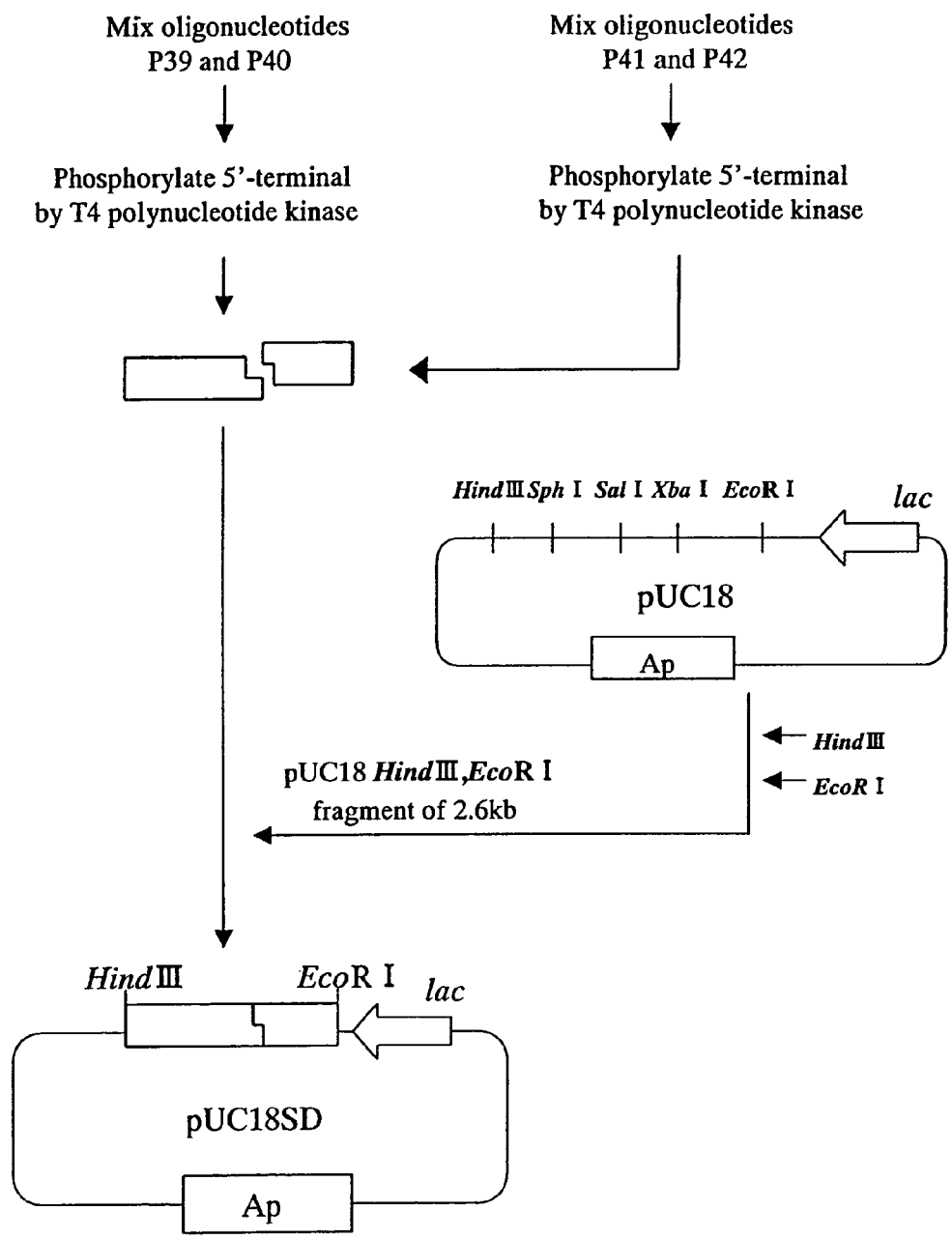
FIG. 22 shows the steps for preparation of pUC18SD. Ap means ampicillin-resistant gene. lac means lac promoter.

(1) Preparation of pUC18SD (refer to FIG. 22)

Oligonucleotides P39 (SEQ ID NO: 39) and P40 (SEQ ID NO: 40) having complementary sequences were mixed and, on the other hand, P41 (SEQ ID NO: 41) and P42 (SEQ ID NO: 42) having the complementary sequences were mixed to prepare two double stranded DNA fragments. Each fragment was subjected to a reaction of adding a phosphate group to each 5'terminus by T4 polynucleotide kinase and cloned to the site of HindIII-EcoRI of pUC18.

The sequence of about 45 bp between HindIII and EcoRI of the resulting plasmid pUC18SD contained a DNA sequence coding for the translation initiation region starting from SD sequence (Shine-Dalgarno sequence) suitable for gene expression of *Bacillus subtilis* and amino acid sequence of MSNITNS (methionine-serine-asparagine-isoleucine-threonine-asparagine-serine) (Fujita, et al. *Microbiology*, 140: 6571-6580, 1998).

Figure 23:
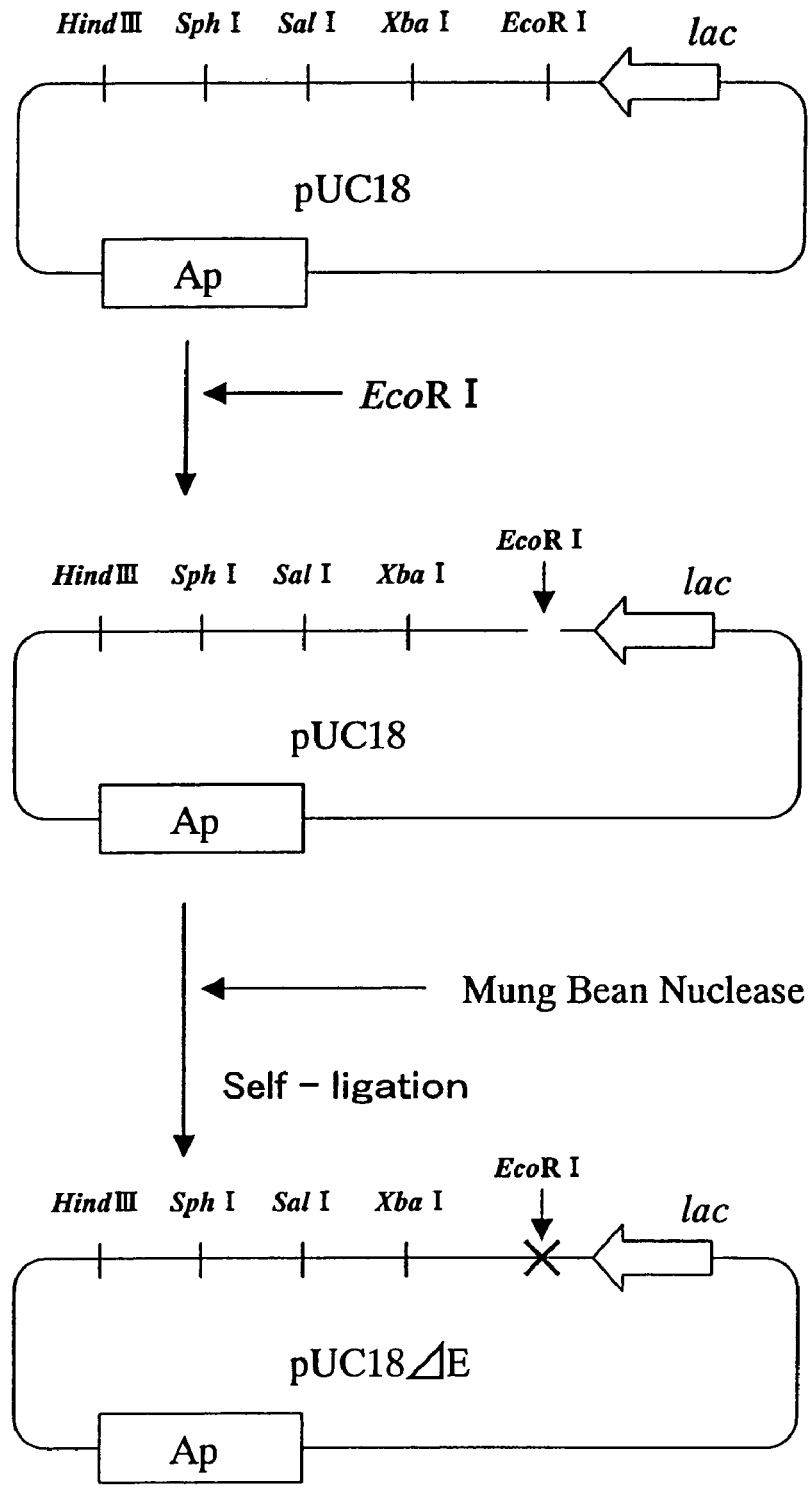
FIG. 23 shows the steps for preparation of pUC18ΔE. Ap means ampicillin-resistant gene. lac means lac promoter.

(2) Preparation of pUC18ΔE (refer to FIG. 23)

pUC18 was completely digested by EcoRI, Mung Bean Nuclease was further added thereto, the mixture was incubated at 37° C. for 15 minutes, purification with ethanol was conducted and a ligation reaction was carried out to prepare pUC18ΔE. The resulting plasmid was confirmed not to be cleaved by EcoRI. By a DNA sequencing, it was confirmed that the recognition sequence 5'-GAATTC-3' of EcoRI was changed to 5'-GATT-3'.

Figure 24:
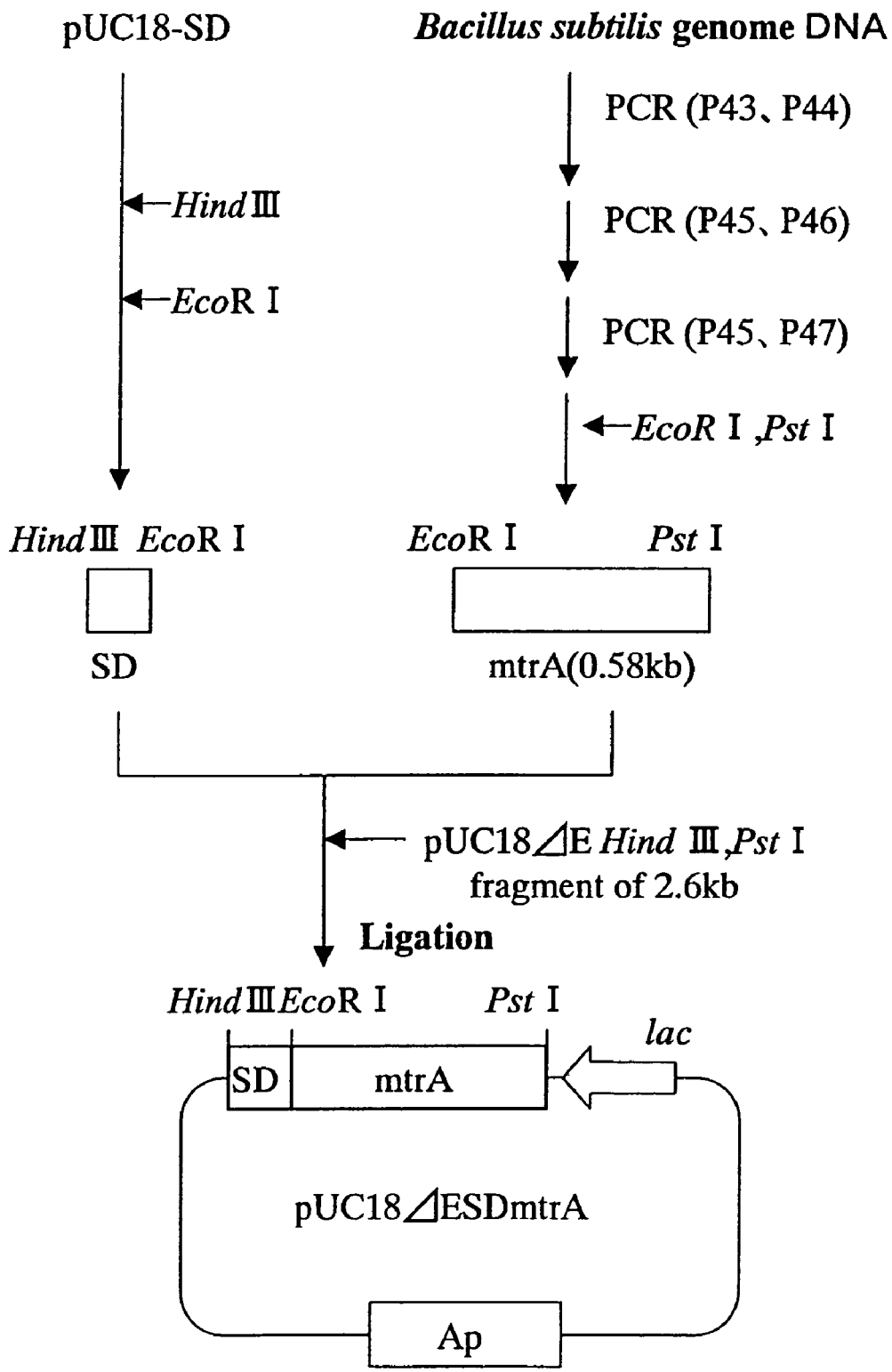
FIG. 24 shows the steps for preparation of pUC18ΔESDmtrA. PCR(P43, P44) means a PCR using sense primer P43 and antisense primer P44. PCR(P45, P46) and PCR(P45, P47) have the similar meanings as well. Ap means ampicillin-resistant gene, mtrA means mtrA gene and SD means gene containing SD sequence and DNA sequence coding for translation initiation region. lac means lac promoter.

(3) Preparation of pUC18ΔESDmtrA (refer to FIG. 24)

For cloning of the mtrA gene, a PCR was carried out using *Bacillus subtilis* genomic DNA as a template and using P43 (SEQ ID NO: 43) and P44 (SEQ ID NO:44), then a PCR was carried out using the amplified DNA as a template and using P45 (SEQ ID NO: 45) and P46 (SEQ ID NO: 46), P45 (SEQ ID NO: 45) and P47 (SEQ ID NO: 47) to introduce cleavage sites for restriction enzymes. Termini of the resulting DNA fragments were digested by EcoRI and PstI and connected to HindIII-EcoRI DNA fragment (SD sequence) prepared from pUC18SD and 2.6 kb HindIII-PstI DNA fragment derived from pUC18ΔE to prepare pUC18ΔESDmtrA. FIG. 31 shows an amino acid sequence corresponding to a DNA base sequence of mtrA cloned on pUC18ΔESDmtrA. Incidentally, the underlined part shows an amino acid sequence derived from CcpA protein to be added to amino terminus of mtrA (Fujita, et al., *Microbiology*, 140:6571-6580, 1998).

Figure 25:
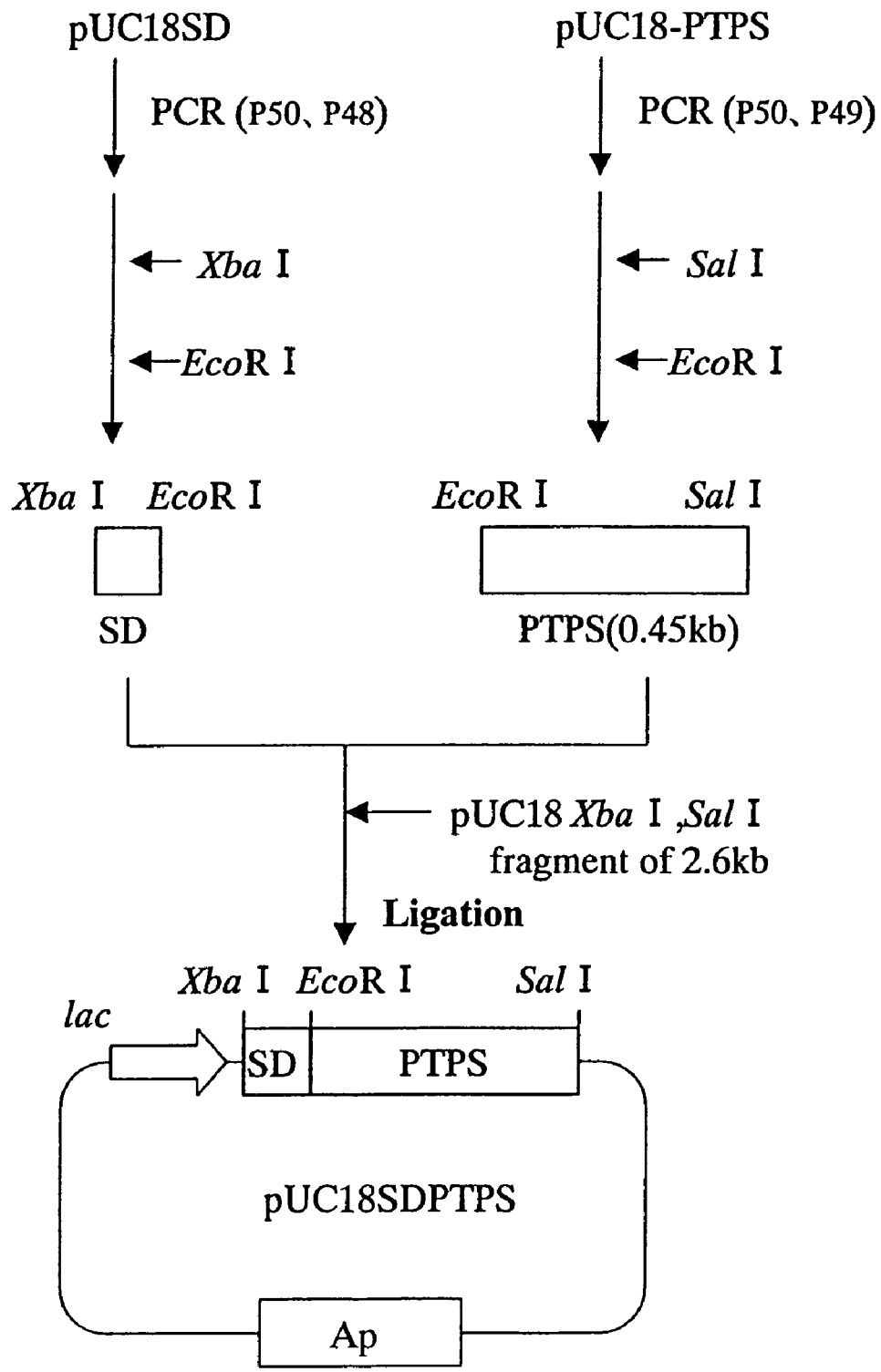
FIG. 25 shows the steps for preparation of pUC18SDPTPS. PCR(P50, P48) means a PCR using sense primer P50 and antisense primer P48. PCR(P50, P49) has the similar meaning as well. Ap means ampicillin-resistant gene, PTPS means PTPS gene and SD means gene containing SD sequence and DNA sequence coding for translation initiation region. lac means lac promoter.

(4) Preparation of pUC18SDPTPS (refer to FIG. 25)

A PCR was carried out using pUC18SD as a template and using primers P50 (SEQ ID NO: 50) and P48 (SEQ ID NO: 48) and termini of the resulting DNA fragment were digested by XbaI and EcoRI to prepare a DNA fragment containing SD sequence. Similarly, pUC18-PTPS prepared in the step of Example 1 as shown by FIG. 4 was used as a template and primers P50 (SEQ ID NO: 50) and P49 (SEQ ID NO: 49) were used to prepare a 0.45 kb EcoRI-SalI fragment containing PTPS gene. They were connected to a 2.6 kb XbaI-SalI DNA fragment derived from pUC18 to prepare pUC18SDPTPS. FIG. 32 shows an amino acid sequence corresponding to a DNA base sequence of PTPS cloned on pUC18SDPTPS. Incidentally, the underlined part shows an amino acid sequence derived from CcpA protein to be added to amino terminus of PTPS (Fujita, et al., *Microbiology*, 140: 6571-6580, 1998).

Figure 26:
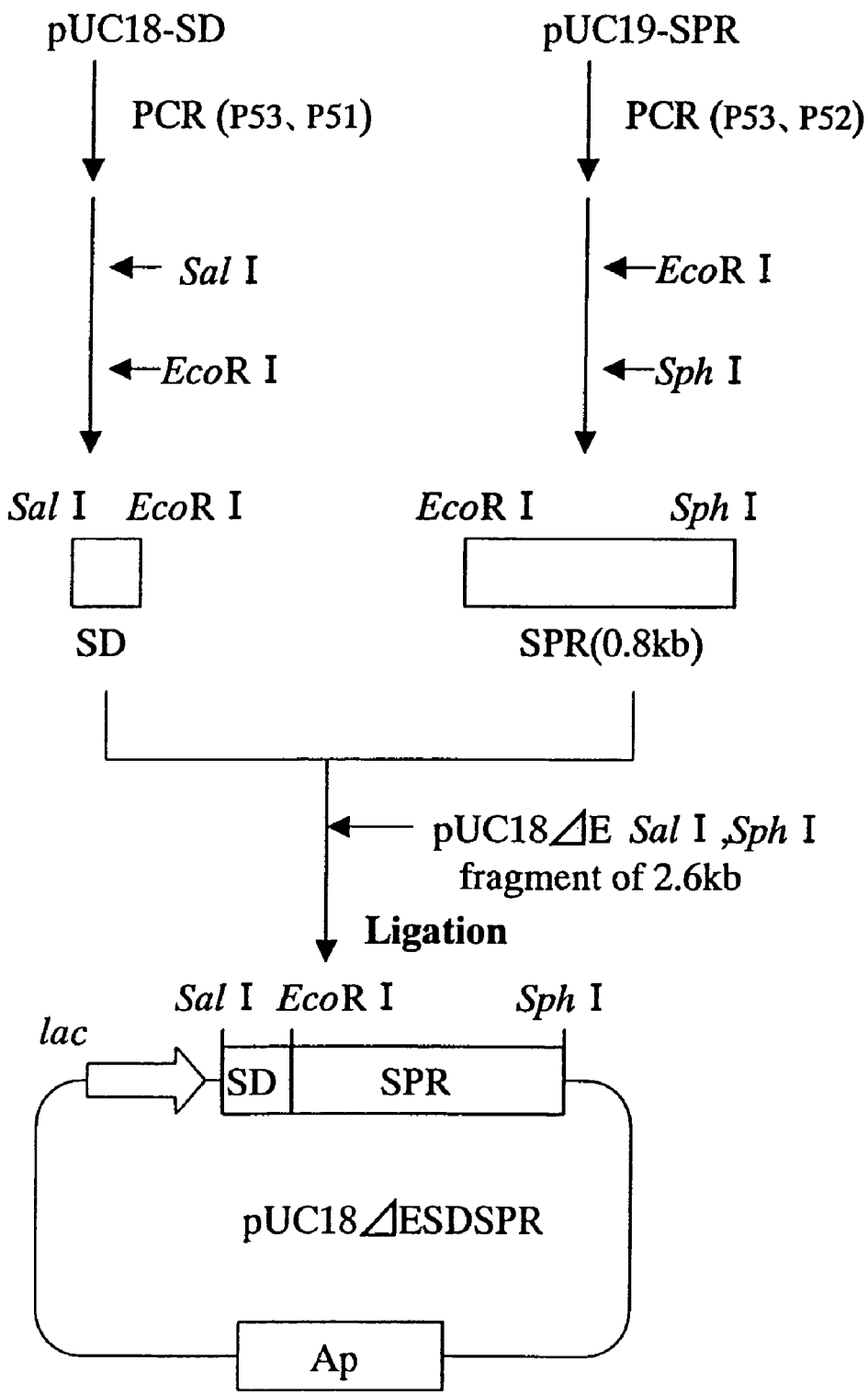
FIG. 26 shows the steps for preparation of pUC18ΔESDSPR. PCR(P53, P51) means a PCR using sense primer P53 and antisense primer P51. PCR(P53, P52) has the similar meaning as well. Ap means ampicillin-resistant gene, SPR means SPR gene and SD means gene containing SD sequence and DNA sequence coding for translation initiation region. lac means lac promoter.

(5) Preparation of pUC18ΔESDSPR (refer to FIG. 26)

A PCR was carried out using pUC18SD as a template and using primers P51 (SEQ ID NO: 51) and P53 (SEQ ID NO: 53) and termini of the resulting DNA fragment were digested by SalI and EcoRI to prepare a DNA fragment containing SD sequence. Similarly, pUC19-SPR prepared in the step of Example 1 as shown by FIG. 5 was used as a template and primers P52 (SEQ ID NO: 52) and P53 (SEQ ID NO: 53) were used to prepare a 0.8 kb EcoRI-SphI fragment containing SPR gene. They were connected to a 2.6 kb SalI-SphI DNA fragment derived from pUC18ΔE to prepare pUC18ΔESDSPR. FIG. 33 shows an amino acid sequence corresponding to a DNA base sequence of SPR cloned on pUC18ΔESDSPR. Incidentally, the underlined part shows an amino acid sequence derived from CcpA protein to be added to amino terminus of SPR (Fujita, et al., *Microbiology*, 140: 6571-6580, 1998).

Figure 27:
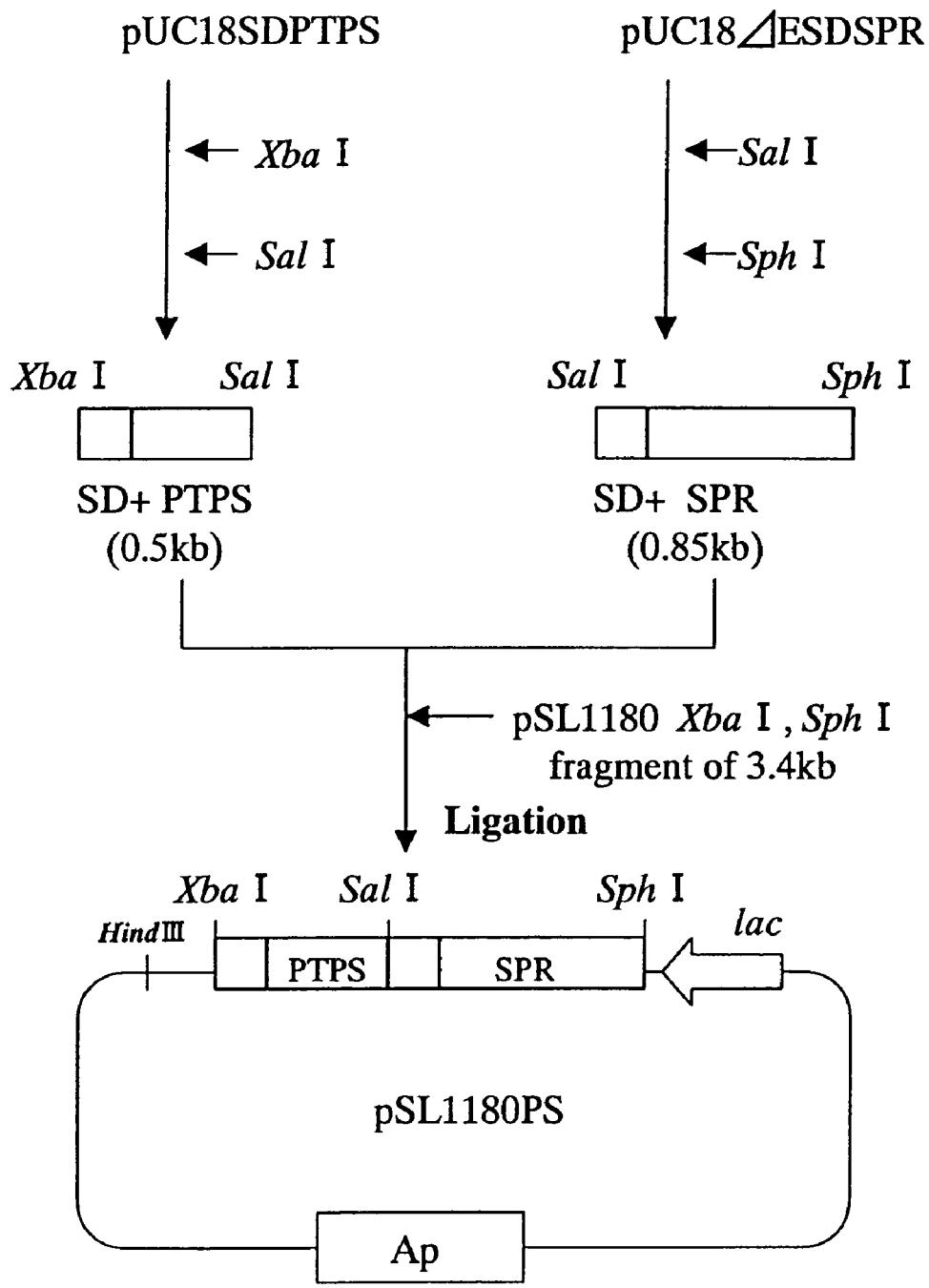
FIG. 27 shows the steps for preparation of pSL1180PS. Ap means ampicillin-resistant gene, PTPS means PTPS gene, SPR means SPR gene and SD means gene containing SD sequence and DNA sequence coding for translation initiation region. lac means lac promoter.

(6) Preparation of pSL1180PS (refer to FIG. 27)

pUC18SDPTPS prepared by the step shown in FIG. 25 as above was digested by XbaI and SalI to prepare a fragment (SD sequence+PTPS) of 0.5 kb. After that, pUC18ΔESDSPR prepared by the step shown in FIG. 6 as above was digested by SalI and SphI to purify a fragment (SD sequence+SPR) of 0.85 kb. Those fragments were connected to XbaI— and SphI-digested product (3.4 kb) of pSL1180 to prepare pSL1180PS.

(7) Preparation of pSL1180 MPS (refer to FIG. 28)

pUC18ΔESDmtrA prepared by the step shown in FIG. 24 as above was digested by HindIII and XbaI to prepare a 0.63 kb fragment and that was connected to a 4.7 kb fragment obtained by digestion of pSL1180PS by HindIII and XbaI to prepare pSL1180MPS.

Figure 29:
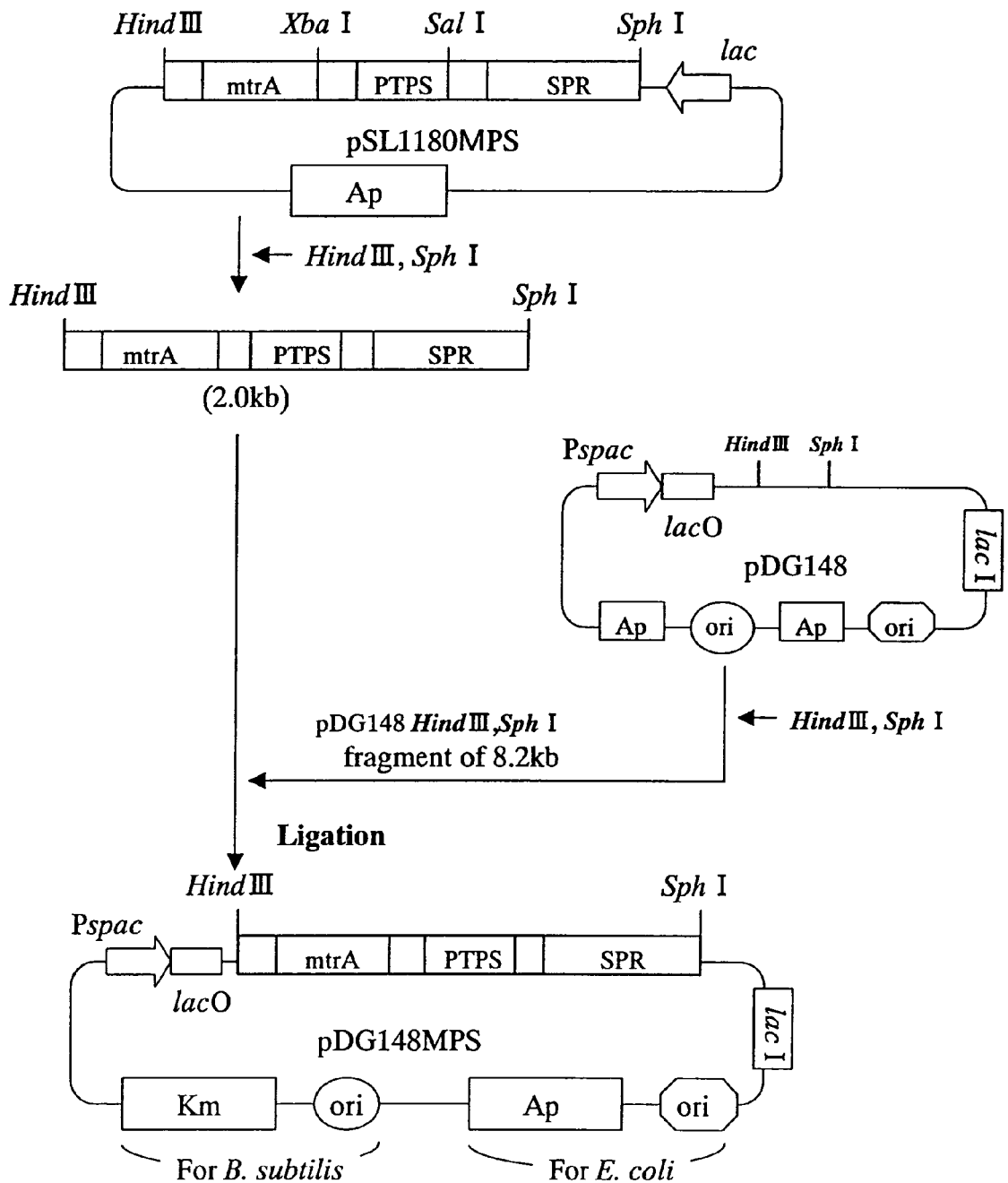
FIG. 29 shows the steps for preparation of pDG148 MPS. Km means kanamycin-resistant gene, Ap means ampicillin-resistant gene, PTPS means PTPS gene, SPR means SPR gene and mtrA means mtrA gene. Pspac means spac promoter, laco means laco promoter and lacI means lacI gene. Ori means origin for replication.

(8) Preparation of pDG148MPS, expression vector for *Bacillus subtilis* (refer to FIG. 29)

pSL1180MPS prepared by the step shown in FIG. 28 as above was digested by HindIII and SphI to prepare a DNA fragment of 2.0 kb where mtrA, PTPS and SPR genes were aligned successively. On the other hand, a shuttle vector pDG148 which was able to be used for *Escherichia coli* and *Bacillus subtilis* (Karmazyn-Campelli, et al., *Cell*, 52, 697-704, 1988) was digested by HindIII and SphI to prepare a DNA fragment of 8.2 kb and that was connected to the previously prepared DNA fragment of 2.0 kb to prepare pDG148 MPS, an expression vector for *Bacillus subtilis*. Incidentally, in FIG. 29, Pspacis spac promoter, lacI is lacI gene, lacO is expression regulatory region by lacI protein, Km is kanamycin-resistant gene, Ap is ampicillin-resistant gene and ori is origin of replication of plasmid.

In this expression vector pDG148MPS, a lacO sequence is coded at the downstream of spac promoter (Pspac) and lacI gene which induces the expression in *Bacillus subtilis* is coded at the downstream of multi-cloning site. Accordingly, in *Bacillus subtilis*, transcription by spac promoter is suppressed by lacI protein. However, when IPTG which is an inducing substance is added to the medium, transcription by spac promoter is activated and expression of gene at the downstream is induced. At the upper stream of mtrA, PTPS and SPR genes, there are aligned SD sequence each being suitable for gene expression of *Bacillus subtilis* and DNA sequence coding for the translation initiation region starting from an amino acid sequence of MSNITNS (methionine-serine-asparagine-isoleucine-threonine-asparagine-serine). Transcription of those three genes aligned in a form of operon is induced by spac promoter.

Figure 30:
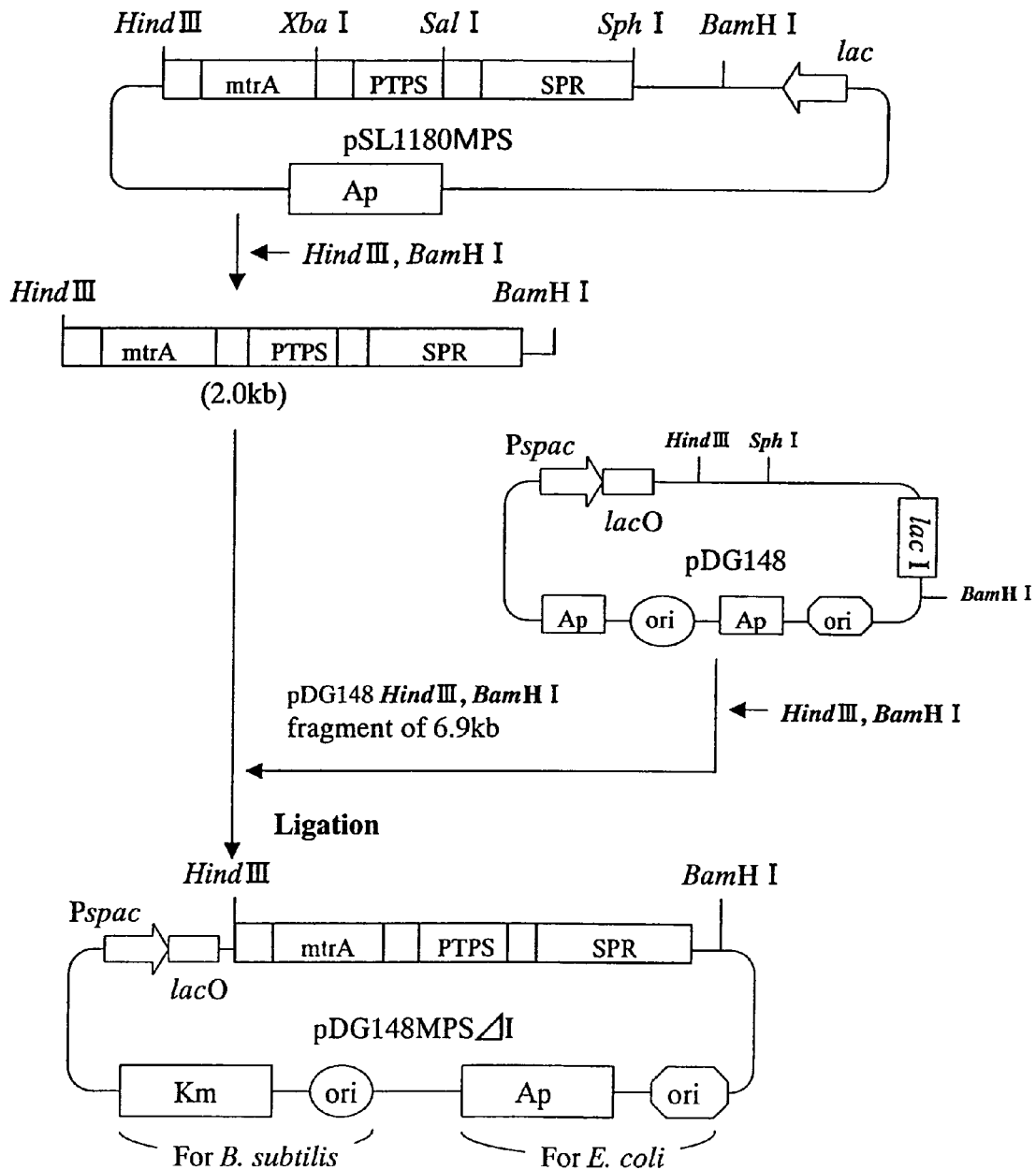
FIG. 30 shows the steps for preparation of pDG148 MPSΔI. Km means kanamycin-resistant gene, Ap means ampicillin-resistant gene, PTPS means PTPS gene, SPR means SPR gene and mtrA means mtrA gene. Pspac means spac promoter, laco means laco promoter and lacI means lacI gene. Ori means origin for replication.

(9) Preparation of pDG148MPSΔI, Expression Vector for *Bacillus subtilis* (Refer to FIG. 30)

The pSL1180 MPS prepared by the step shown in FIG. 28 as above was digested by HindIII and BamHI which were restriction enzymes to prepare a DNA fragment of 2.0 kb where mtrA, PTPS and SPR genes were aligned successively. This was connected to the above digested product (6.9 kb) of pDG148 by HindIII and BamHI to prepare pDG148MPSΔI, an expression vector for *Bacillus subtilis*. Incidentally, in FIG. 30, Pspac is spac promoter, lacO is expression regulatory region by lacI protein, Km is kanamycin-resistant gene, Ap is ampicillin-resistant gene and ori is origin of replication of plasmid.

In this expression vector pDG148MPSΔI, a laco sequence is available at the downstream of spac promoter (Pspac) but, since lacI gene part is deficient from pDG148, no suppression to spac promoter is resulted in *Bacillus subtilis*. Accordingly, expression of gene at downstream is constantly induced. At the upper stream of mtrA, PTPS and SPR genes, there are aligned SD sequence each being suitable for gene expression of *Bacillus subtilis* and DNA sequence coding for the translation initiation region starting from an amino acid sequence of MSNITNS. Transcription of those three genes aligned in a form of operon is induced by spac promoter.

Example 14

Production of the Biopterin Compound by *Bacillus subtilis*

*Bacillus subtilis* 1A1 strain (trpC2) (Fujita, et al., *Microbiology*, 140:6571-6580, 1998) was transformed by pDG148 MPS or pDG148MPSΔI according to the following method. Thus, each of the plasmids of pDG148MPS and pDG148MPSΔI used for the transformation was a vector derived from a shuttle vector pDG148 (Karmazyn-Campelli, et al., *Cell*, 52, 697-704, 1988) which was transformable for both *Escherichia coli* and *Bacillus subtilis* and, in the case of *Escherichia coli*, resistance to ampicillin was able to be used as a selective marker while, in the case of *Bacillus subtilis*, resistance to kanamycin was able to be used as a selective marker.

*Bacillus subtilis* 1A1 strain was streaked on a TBABG plate and a pre-incubation was carried out for 12 hours. [Composition in 1 L of the TBABG plate: 10 g of tryptone, 3 g of beef extract, 5 g of NaCl, 15 g of agar powder and 1.8 g of glucose]

Cells were scraped off from the plate and suspended in 2 ml of a CI medium. [Composition of the CI medium: 0.2% of $(NH_4)_2SO_4$, 1.4% of $K_2HPO_4$, 0.6% of $KH_2PO_4$, 0.1% of $Na_3$ citrate.$2H_2O$, 5 mM of $MgSO_4$, 0.5% of glucose, 0.02% of Casamino acid and 50 μg/ml of tryptophane (trp)].

The resulting suspension was diluted with the CI medium to as to make $OD_{600\ nm}$=0.08 and subjected to a shaking culture at 37° C. During the cultivation, values of $OD_{600\ nm}$ were appropriately measured to confirm that the growth entered the stationary phase.

The culture broth (2.5 ml) was centrifuged (at 2500 rpm and room temperature (RT) for 10 minutes) and the collected cells were suspended in 5 ml of a CII medium and subjected to a shaking culture for about 30 minutes to give competent cells. [Composition of the CII medium: 0.2% of $(NH_4)_2SO_4$, 1.4% of $K_2HPO_4$, 0.6% of $KH_2PO_4$, 0.1% of $Na_3$ citrate.$2H_2O$, 5 mM of $MgSO_4$, 0.5% of glucose, 0.01% of Casamino acid and 5 μg/ml of tryptophane (trp)].

The competent cell (1 ml) was mixed with 1 μg of pDG148 MPS or pDG148MPSΔI prepared from *Escherichia coli* JM101 strain which was a recA$^+$ strain and subjected to a shaking culture gently at 37° C. for 2 hours. After that, the culture broth was streaked to a TBABG plate containing 5 μg/ml of kanamycin and incubated at 37° C. for about 12 hours to give each of the transformants 1A1/pDG148MPS and 1A1/pDG148MPSΔI.

Colony of each of the resulting transformants was pre-cultured in 3 ml of an LB medium containing 5 μg/ml of kanamycin (Km) for about 3 hours. After that, it was inoculated on an NU medium (3.5 ml) containing 2% of glucose, 1 mM of IPTG and 5 μg/ml of Km and subjected to a shaking culture at 37° C. for 20 hours. Similar cultivation was carried out in a medium containing no kanamycin for *Bacillus subtilis* as a control for each strain as well. [Composition of the NU medium (per 1 L): 4 g of yeast extract, 4 g of $KH_2PO_4$, 4 g of $K_2HPO_4$, 2.8 g of $Na_2HPO_4$, 0.2 g of $NH_4Cl$, 2 g of $MgSO_4.7H_2O$, 0.04 g of $FeSO_4$, 0.04 g of $CaCl_2.2H_2O$, 0.01 g of $MnSO_4.5H_2O$, 0.01 g of $AlCl_3.6H_2O$, 0.004 g of $CoCl_2.6H_2O$, 0.002 g of $ZnSO_4.7H_2O$, 0.002 g of $Na_2MoO_4.2H_2O$, 0.001 g of $CuCl_2.2H_2O$ and 0.0005 g of $H_3BO_3$].

The result was that, in all strains including the control strain, values of $OD_{600\ nm}$ were 10 to 12. Growth of the cells was good and any changes by transformation or gene expression induced by IPTG were not observed. The supernatant of culture broth after 20 hours from the start of the culture was oxidized by a method mentioned in Example 4 and subjected to an HPLC analysis.

Figure 34:
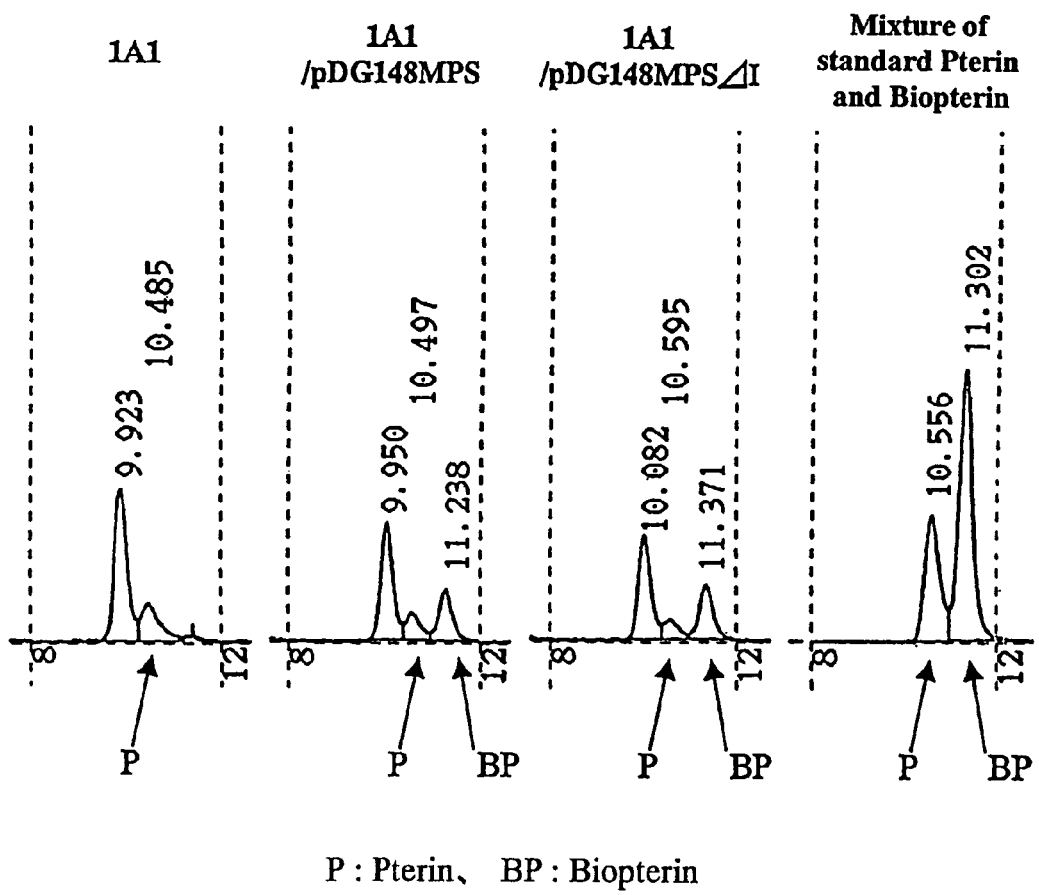
FIG. 34 shows HPLC analysis of culture supernatant of *Bacillus subtilis* strains 1A1/pDG148 MPS and 1A1/pDG148 MPSΔI.

Result of the HPLC analysis is shown in FIG. 34. In the 1A1 strain (right end) where no plasmid was introduced, no peak was noted at the eluted position of the standard BP specimen while, in other two strains (1A1/pDG148MPS and 1A1/pDG148MPSΔI), peaks were noted at the eluting position of the standard BP specimen whereby it became clear that the prepared *Bacillus subtilis* had a BP-producing ability. Upon calculation from the area ratio of the peak areas, amount of the produced BP was about 0.45 μg/ml in all cases.

INDUSTRIAL APPLICABILITY

The present invention achieves an advantage that the biopterin compounds being expected to have pharmacological effect can be produced in large quantities in an industrial scale starting from less expensive medium materials. As a result, studies for the biopterin compounds, particularly for pharmacological action thereof, are now able to be easily carried out and development of new pharmaceuticals is able to be promoted.

The present invention also achieves an advantage that production of DHBP and BP which are oxidized products of THBP becomes possible. As a result, studies for metabolism of biopterin compounds are now able to be easily carried out.

The invention claimed is:

1. A transformed cell used for the production of a biopterin compound made by transforming a host cell with a gene encoding a 6-pyruvoyltetrahydropterin synthase, a gene encoding a sepiapterin reductase and optionally a gene encoding a GTP cyclohydrase I, wherein the host cell is *Escherichia coli*, *Saccharomyces cerevisiae*, or *Bacillus subtilis*,
the gene encoding sepiapterin reductase being (i) a gene having the base sequence set forth in SEQ ID NO: 56 or (ii) a gene having a base sequence having an identity of not less than 95% to the base sequence set forth in SEQ ID NO: 56 and encoding a protein having sepiapterin reductase activity.

2. The transformed cell according to claim 1, wherein the host cell is a mutant cell having a GTP synthesizing activity not less than the GTP synthesizing activity of the corresponding host cell lacking the mutation.

3. The transformed cell according to claim 2, wherein the host cell is a mutant cell having a 8-azaguanine resistance not less than the 8-azaguanine resistance of the corresponding host cell lacking the mutation.

4. The transformed cell according to claim 2, wherein the host cell is a genetically recombinant cell transformed with a gene encoding an IMP dehydrogenase and a gene encoding a GMP synthase.

5. The transformed cell according to claim 2, wherein the host cell (1) is a mutant having GTP cyclohydrase I activity not less than the GTP cyclohydrase I activity of the corresponding host cell lacking the mutation, and (2) is transformed with a gene encoding a 6-pyruvoyltetrahydropterin synthase and a gene encoding a sepiapterin reductase, the gene encoding sepiapterin reductase being (i) a gene having the base sequence set forth in SEQ ID NO: 56; or (ii) a gene having a base sequence having an identity of not less than 95% to the base sequence set forth in SEQ ID NO: 56 and encoding a protein having sepiapterin reductase activity.

6. The transformed cell according to claim 1, wherein the host cell is transformed with the gene encoding a GTP cyclohydrase I and the gene is mtrA gene from *Bacillus subtilis*.

7. A process for production of a biopterin compound comprising
(a) transforming a host cell with a gene encoding a 6-pyruvoyltetrahydropterin synthase, a gene encoding a sepiapterin reductase and optionally a gene encoding a GTP cyclohydrase I,
(b) culturing the transformed cell to produce tetrahydrobiopterin,
(c) optionally oxidizing the resulting tetrahydrobiopterin, and
(d) collecting one or more biopterin compounds selected from the group consisting of tetrahydrobiopterin, dihydrobiopterin and biopterin, wherein the host cell is *Escherichia coli*, *Saccharomyces cerevisiae* or *Bacillus subtilis*,
the gene encoding sepiapterin reductase being (i) gene having the base sequence set forth in SEQ ID NO: 56 or (ii) a gene having a base sequence having an identity of not less than 95% to the base sequence set forth in SEQ ID NO: 56 and encoding a protein having sepiapterin activity.

8. The process for production of the biopterin compound according to claim 7, wherein the gene is a gene having a base sequence having an identity of not less than 95% to the base sequence set forth in SEQ ID NO: 56 and encoding a protein having sepiapterin reductase activity which is isolated from rat.

9. The process for production of the biopterin compound according to claim 7, wherein the gene encoding sepiapterin reductase is a gene that has the base sequence set forth in SEQ ID NO: 56.

10. The process for production of the biopterin compound according to claim 7, which comprises oxidizing tetrahydrobiopterin to produce biopterin.

11. The process for production of the biopterin compound according to claim 7, wherein the collected dihydrobiopterin or biopterin is reduced to produce tetrahydrobiopterin.

12. The process for production of the biopterin compound according to claim 7, wherein the host cell is (1) a mutant having GTP cyclohydrase I activity not less than the GTP cyclohydrase I activity of the corresponding host cell lacking the mutation, and (2) transformed with an expression vector having a gene encoding a 6-pyruvoyltetrahydropterin synthase and a gene encoding a sepiapterin reductase, the gene encoding sepiapterin reductase being (i) a gene having the base sequence set forth in SEQ ID NO: 56; or (ii) a gene having a base sequence having an identity of not less than 95% to the base sequence set forth in SEQ ID NO: 56 and encoding a protein having sepiapterin reductase activity.

13. The process for production of the biopterin compound according to claim 7, wherein the host cell is transformed with the gene encoding a GTP cyclohydrase I and the gene is mtrA gene from *Bacillus subtilis*.

14. The process for production of the biopterin compound according to claim 7, wherein the host cell is a mutant cell having a GTP synthesizing activity not less than the GTP synthesizing activity of the corresponding host cell lacking the mutation.

15. The process for production of the biopterin compound according to claim 14, wherein the host cell is a mutant cell having a 8-azaguanine resistance not less than the 8-azaguanine resistance of the corresponding host cell lacking the mutation.

16. The process for production of the biopterin compound according to claim 14, wherein the host cell is a genetically recombinant cell transformed with a gene encoding an IMP dehydrogenase and a gene encoding a GMP synthase.

* * * * *

SEQUENCE LISTING

```
<160> NUMBER OF SEQ ID NOS: 65

<210> SEQ ID NO 1
<211> LENGTH: 21
<212> TYPE: DNA
<213> ORGANISM: Artificial sequence
<220> FEATURE:
<223> OTHER INFORMATION: Synthetic construct; Primer P1

<400> SEQUENCE: 1
aaatcataaa tgccatcact c                                                  21

<210> SEQ ID NO 2
<211> LENGTH: 21
<212> TYPE: DNA
<213> ORGANISM: Artificial sequence
<220> FEATURE:
<223> OTHER INFORMATION: Synthetic construct; Primer P2

<400> SEQUENCE: 2
gccttttaat cagttgtgat g                                                  21

<210> SEQ ID NO 3
<211> LENGTH: 25
<212> TYPE: DNA
<213> ORGANISM: Artificial sequence
<220> FEATURE:
<223> OTHER INFORMATION: Synthetic construct; Primer P3
```

-continued

```
<400> SEQUENCE: 3
aaagaattca tgccatcact cagta                                          25

<210> SEQ ID NO 4
<211> LENGTH: 23
<212> TYPE: DNA
<213> ORGANISM: Artificial sequence
<220> FEATURE:
<223> OTHER INFORMATION: Synthetic construct; Primer P4

<400> SEQUENCE: 4
gccttttaac tagttgtgat gac                                            23

<210> SEQ ID NO 5
<211> LENGTH: 26
<212> TYPE: DNA
<213> ORGANISM: Artificial sequence
<220> FEATURE:
<223> OTHER INFORMATION: Synthetic construct; Primer P5

<400> SEQUENCE: 5
ccggaattcc atgccatcac tcagta                                         26

<210> SEQ ID NO 6
<211> LENGTH: 31
<212> TYPE: DNA
<213> ORGANISM: Artificial sequence
<220> FEATURE:
<223> OTHER INFORMATION: Synthetic construct; Primer P6

<400> SEQUENCE: 6
gatttgtcga ctatcaggct gaaaatcttc t                                   31

<210> SEQ ID NO 7
<211> LENGTH: 21
<212> TYPE: DNA
<213> ORGANISM: Artificial sequence
<220> FEATURE:
<223> OTHER INFORMATION: Synthetic construct; Primer P7

<400> SEQUENCE: 7
cttgtgggtc tttggtctga a                                              21

<210> SEQ ID NO 8
<211> LENGTH: 21
<212> TYPE: DNA
<213> ORGANISM: Artificial sequence
<220> FEATURE:
<223> OTHER INFORMATION: Synthetic construct; Primer P8

<400> SEQUENCE: 8
gggtaggtga tgactgctgt g                                              21

<210> SEQ ID NO 9
<211> LENGTH: 24
<212> TYPE: DNA
<213> ORGANISM: Artificial sequence
<220> FEATURE:
<223> OTHER INFORMATION: Synthetic construct; Primer P9

<400> SEQUENCE: 9
tttggtctga attccatgaa cgcg                                           24

<210> SEQ ID NO 10
<211> LENGTH: 33
```

<212> TYPE: DNA
<213> ORGANISM: Artificial sequence
<220> FEATURE:
<223> OTHER INFORMATION: Synthetic construct; Primer P10

<400> SEQUENCE: 10
tattaaaact agtatctatt ctcctttgta gac                                  33

<210> SEQ ID NO 11
<211> LENGTH: 30
<212> TYPE: DNA
<213> ORGANISM: Artificial sequence
<220> FEATURE:
<223> OTHER INFORMATION: Synthetic construct; Primer P11

<400> SEQUENCE: 11
gcccaagctt gtttgacagc ttatcatcga                                      30

<210> SEQ ID NO 12
<211> LENGTH: 31
<212> TYPE: DNA
<213> ORGANISM: Artificial sequence
<220> FEATURE:
<223> OTHER INFORMATION: Synthetic construct; Primer P12

<400> SEQUENCE: 12
gatttgtcga ctatcaggct gaaaatcttc t                                    31

<210> SEQ ID NO 13
<211> LENGTH: 21
<212> TYPE: DNA
<213> ORGANISM: Artificial sequence
<220> FEATURE:
<223> OTHER INFORMATION: Synthetic construct; Primer P13

<400> SEQUENCE: 13
ggcaggctag gttgcgctgt c                                               21

<210> SEQ ID NO 14
<211> LENGTH: 21
<212> TYPE: DNA
<213> ORGANISM: Artificial sequence
<220> FEATURE:
<223> OTHER INFORMATION: Synthetic construct; Primer P14

<400> SEQUENCE: 14
gggcttaaat gtcatagaag t                                               21

<210> SEQ ID NO 15
<211> LENGTH: 30
<212> TYPE: DNA
<213> ORGANISM: Artificial sequence
<220> FEATURE:
<223> OTHER INFORMATION: Synthetic construct; Primer P15

<400> SEQUENCE: 15
aaaggatccg gcaggctagg ttgcgctgtc                                      30

<210> SEQ ID NO 16
<211> LENGTH: 26
<212> TYPE: DNA
<213> ORGANISM: Artificial sequence
<220> FEATURE:
<223> OTHER INFORMATION: Synthetic construct; Primer P16

<400> SEQUENCE: 16

```
cctgactagt taaatgtcat agaagt                                          26
```

```
<210> SEQ ID NO 17
<211> LENGTH: 30
<212> TYPE: DNA
<213> ORGANISM: Artificial sequence
<220> FEATURE:
<223> OTHER INFORMATION: Synthetic construct; Primer P17

<400> SEQUENCE: 17
atgaagcttg ggcaggctag gttgcgctgt                                      30
```

```
<210> SEQ ID NO 18
<211> LENGTH: 31
<212> TYPE: DNA
<213> ORGANISM: Artificial sequence
<220> FEATURE:
<223> OTHER INFORMATION: Synthetic construct; Primer P18

<400> SEQUENCE: 18
gatttgtcga ctatcaggct gaaaatcttc t                                    31
```

```
<210> SEQ ID NO 19
<211> LENGTH: 30
<212> TYPE: DNA
<213> ORGANISM: Artificial sequence
<220> FEATURE:
<223> OTHER INFORMATION: Synthetic construct; Primer P19

<400> SEQUENCE: 19
gagcgtcgac tgagggcaac gcaattaatg                                      30
```

```
<210> SEQ ID NO 20
<211> LENGTH: 30
<212> TYPE: DNA
<213> ORGANISM: Artificial sequence
<220> FEATURE:
<223> OTHER INFORMATION: Synthetic construct; Primer P20

<400> SEQUENCE: 20
cgcgggatcc ctattctcct ttgtagacca                                      30
```

```
<210> SEQ ID NO 21
<211> LENGTH: 30
<212> TYPE: DNA
<213> ORGANISM: Artificial sequence
<220> FEATURE:
<223> OTHER INFORMATION: Synthetic construct; Primer P21

<400> SEQUENCE: 21
gagcggatcc tgagcgcaac gcaattaatg                                      30
```

```
<210> SEQ ID NO 22
<211> LENGTH: 30
<212> TYPE: DNA
<213> ORGANISM: Artificial sequence
<220> FEATURE:
<223> OTHER INFORMATION: Synthetic construct; Primer P22

<400> SEQUENCE: 22
cgcggcatgc ttaaatgtca tagaagtcca                                      30
```

```
<210> SEQ ID NO 23
<211> LENGTH: 37
<212> TYPE: DNA
<213> ORGANISM: Artificial sequence
```

<220> FEATURE:
<223> OTHER INFORMATION: Synthetic construct; Primer P23

<400> SEQUENCE: 23
ttcaaggatc ccaaaatgca taacatccaa ttagtgc                    37

<210> SEQ ID NO 24
<211> LENGTH: 38
<212> TYPE: DNA
<213> ORGANISM: Artificial sequence
<220> FEATURE:
<223> OTHER INFORMATION: Synthetic construct; Primer P24

<400> SEQUENCE: 24
ctattactcg agttaataca tacacgatat atcgtcgc                   38

<210> SEQ ID NO 25
<211> LENGTH: 29
<212> TYPE: DNA
<213> ORGANISM: Artificial sequence
<220> FEATURE:
<223> OTHER INFORMATION: Synthetic construct; Primer P25

<400> SEQUENCE: 25
gattggatcc accatgaacg cggcggttg                             29

<210> SEQ ID NO 26
<211> LENGTH: 29
<212> TYPE: DNA
<213> ORGANISM: Artificial sequence
<220> FEATURE:
<223> OTHER INFORMATION: Synthetic construct; Primer P26

<400> SEQUENCE: 26
gcgactcgag tctattctcc tttgtagac                             29

<210> SEQ ID NO 27
<211> LENGTH: 43
<212> TYPE: DNA
<213> ORGANISM: Artificial sequence
<220> FEATURE:
<223> OTHER INFORMATION: Synthetic construct; Primer P27

<400> SEQUENCE: 27
gaccggatcc accatggaag gtggcaggct aggttgcgct gtc             43

<210> SEQ ID NO 28
<211> LENGTH: 31
<212> TYPE: DNA
<213> ORGANISM: Artificial sequence
<220> FEATURE:
<223> OTHER INFORMATION: Synthetic construct; Primer P28

<400> SEQUENCE: 28
ccgcctcgag ttaaatgtca tagaagtcca c                          31

<210> SEQ ID NO 29
<211> LENGTH: 25
<212> TYPE: DNA
<213> ORGANISM: Artificial sequence
<220> FEATURE:
<223> OTHER INFORMATION: Synthetic construct; Primer P29

<400> SEQUENCE: 29
atccgcatgc acggattaga agccg                                 25

<210> SEQ ID NO 30
<211> LENGTH: 29
<212> TYPE: DNA
<213> ORGANISM: Artificial sequence
<220> FEATURE:
<223> OTHER INFORMATION: Synthetic construct; Primer P30

<400> SEQUENCE: 30
atgtactagt ctgcgttatc ccctgattc                                29

<210> SEQ ID NO 31
<211> LENGTH: 25
<212> TYPE: DNA
<213> ORGANISM: Artificial sequence
<220> FEATURE:
<223> OTHER INFORMATION: Synthetic construct; Primer P31

<400> SEQUENCE: 31
atccactagt acggattaga agccg                                    25

<210> SEQ ID NO 32
<211> LENGTH: 29
<212> TYPE: DNA
<213> ORGANISM: Artificial sequence
<220> FEATURE:
<223> OTHER INFORMATION: Synthetic construct; Primer P32

<400> SEQUENCE: 32
atgtactagt ctgcgttatc ccctgattc                                29

<210> SEQ ID NO 33
<211> LENGTH: 23
<212> TYPE: DNA
<213> ORGANISM: Artificial sequence
<220> FEATURE:
<223> OTHER INFORMATION: Synthetic construct; Primer P33

<400> SEQUENCE: 33
gtaaagtacc agtgaccgga agc                                      23

<210> SEQ ID NO 34
<211> LENGTH: 27
<212> TYPE: DNA
<213> ORGANISM: Artificial sequence
<220> FEATURE:
<223> OTHER INFORMATION: Synthetic construct; Primer P34

<400> SEQUENCE: 34
cagctggttt aattaatcga tgttagt                                  27

<210> SEQ ID NO 35
<211> LENGTH: 23
<212> TYPE: DNA
<213> ORGANISM: Artificial sequence
<220> FEATURE:
<223> OTHER INFORMATION: Synthetic construct; Primer P35

<400> SEQUENCE: 35
cagggcattc actttgcttt tag                                      23

<210> SEQ ID NO 36
<211> LENGTH: 23
<212> TYPE: DNA
<213> ORGANISM: Artificial sequence
<220> FEATURE:
<223> OTHER INFORMATION: Synthetic construct; Primer P36

-continued

```
<400> SEQUENCE: 36
ttcgcttacg caggtatcat tat                                    23

<210> SEQ ID NO 37
<211> LENGTH: 30
<212> TYPE: DNA
<213> ORGANISM: Artificial sequence
<220> FEATURE:
<223> OTHER INFORMATION: Synthetic construct; Primer P37

<400> SEQUENCE: 37
attacgaatt ccatgaaaga agttaataaa                             30

<210> SEQ ID NO 38
<211> LENGTH: 30
<212> TYPE: DNA
<213> ORGANISM: Artificial sequence
<220> FEATURE:
<223> OTHER INFORMATION: Synthetic construct; Primer P38

<400> SEQUENCE: 38
atgcctgcag tctagacgca ttagtcctgg                             30

<210> SEQ ID NO 39
<211> LENGTH: 30
<212> TYPE: DNA
<213> ORGANISM: Artificial sequence
<220> FEATURE:
<223> OTHER INFORMATION: Synthetic construct; Primer P39

<400> SEQUENCE: 39
agcttgtgta tccagtaaaa ggagtggttt                             30

<210> SEQ ID NO 40
<211> LENGTH: 30
<212> TYPE: DNA
<213> ORGANISM: Artificial sequence
<220> FEATURE:
<223> OTHER INFORMATION: Synthetic construct; Primer P40

<400> SEQUENCE: 40
cctaaaacca ctccttttac tggatacaca                             30

<210> SEQ ID NO 41
<211> LENGTH: 19
<212> TYPE: DNA
<213> ORGANISM: Artificial sequence
<220> FEATURE:
<223> OTHER INFORMATION: Synthetic construct; Primer P41

<400> SEQUENCE: 41
taggatgacg aatattacg                                         19

<210> SEQ ID NO 42
<211> LENGTH: 19
<212> TYPE: DNA
<213> ORGANISM: Artificial sequence
<220> FEATURE:
<223> OTHER INFORMATION: Synthetic construct; Primer P42

<400> SEQUENCE: 42
aattcgtaat attgctcat                                         19

<210> SEQ ID NO 43
```

<211> LENGTH: 23
<212> TYPE: DNA
<213> ORGANISM: Artificial sequence
<220> FEATURE:
<223> OTHER INFORMATION: Synthetic construct; Primer P43

<400> SEQUENCE: 43
cagggcattc actttgcttt tag                                           23

<210> SEQ ID NO 44
<211> LENGTH: 23
<212> TYPE: DNA
<213> ORGANISM: Artificial sequence
<220> FEATURE:
<223> OTHER INFORMATION: Synthetic construct; Primer P44

<400> SEQUENCE: 44
ttcgcttacg caggtatcat tat                                           23

<210> SEQ ID NO 45
<211> LENGTH: 30
<212> TYPE: DNA
<213> ORGANISM: Artificial sequence
<220> FEATURE:
<223> OTHER INFORMATION: Synthetic construct; Primer P45

<400> SEQUENCE: 45
attacgaatt ccatgaaaga agttaataaa                                    30

<210> SEQ ID NO 46
<211> LENGTH: 30
<212> TYPE: DNA
<213> ORGANISM: Artificial sequence
<220> FEATURE:
<223> OTHER INFORMATION: Synthetic construct; Primer P46

<400> SEQUENCE: 46
gctctagacg cattagtcct ggcgtttaat                                    30

<210> SEQ ID NO 47
<211> LENGTH: 30
<212> TYPE: DNA
<213> ORGANISM: Artificial sequence
<220> FEATURE:
<223> OTHER INFORMATION: Synthetic construct; Primer P47

<400> SEQUENCE: 47
atgcctgcag tctagacgca ttagtcctgg                                    30

<210> SEQ ID NO 48
<211> LENGTH: 30
<212> TYPE: DNA
<213> ORGANISM: Artificial sequence
<220> FEATURE:
<223> OTHER INFORMATION: Synthetic construct; Primer P48

<400> SEQUENCE: 48
gtgcctctag agtgtatcca gtaaaaggag                                    30

<210> SEQ ID NO 49
<211> LENGTH: 30
<212> TYPE: DNA
<213> ORGANISM: Artificial sequence
<220> FEATURE:
<223> OTHER INFORMATION: Synthetic construct; Primer P49

<400> SEQUENCE: 49

```
caggcgtcga cttcgaaagc ggccgcgact                               30
```

<210> SEQ ID NO 50
<211> LENGTH: 24
<212> TYPE: DNA
<213> ORGANISM: Artificial sequence
<220> FEATURE:
<223> OTHER INFORMATION: Synthetic construct; Primer P50

<400> SEQUENCE: 50

```
ctcattaggc accccaggct ttac                                     24
```

<210> SEQ ID NO 51
<211> LENGTH: 30
<212> TYPE: DNA
<213> ORGANISM: Artificial sequence
<220> FEATURE:
<223> OTHER INFORMATION: Synthetic construct; Primer P51

<400> SEQUENCE: 51

```
gtgccgtcga cgtgtatcca gtaaaaggag                               30
```

<210> SEQ ID NO 52
<211> LENGTH: 30
<212> TYPE: DNA
<213> ORGANISM: Artificial sequence
<220> FEATURE:
<223> OTHER INFORMATION: Synthetic construct; Primer P52

<400> SEQUENCE: 52

```
caggcgcatg cttcgaaagc ggccgcgact                               30
```

<210> SEQ ID NO 53
<211> LENGTH: 20
<212> TYPE: DNA
<213> ORGANISM: Artificial sequence
<220> FEATURE:
<223> OTHER INFORMATION: Synthetic construct; Primer P53

<400> SEQUENCE: 53

```
gcaacgcaat taatgtgagt                                          20
```

<210> SEQ ID NO 54
<211> LENGTH: 696
<212> TYPE: DNA
<213> ORGANISM: Artificial sequence
<220> FEATURE:
<223> OTHER INFORMATION: Synthetic construct; GCH cloned on pSTV28-GCH

<400> SEQUENCE: 54

```
atgaccatga ttacgaattc catgccaatg ccatcactca gtaaagaagc ggccctggtt    60
catgaagcgt tagttgcgcg aggactggaa acaccgctgc gcccgcccgt gcatgaaatg   120
gataacgaaa cgcgcaaaag ccttattgct ggtcatatga ccgaaatcat gcagctgctg   180
aatctcgacc tggctgatga cagtttgatg gaaacgccgc atcgcatcgc taaaatgtat   240
gtcgatgaaa ttttctccgg tctggattac gccaatttcc cgaaaatcac cctcattgaa   300
aacaaaatga aggtcgatga atggtcacc gtgcgcgata tcactctgac cagcacctgt   360
gaacaccatt tgttaccat cgatggcaaa gcgacggtgg cctatatccc gaaagattcg   420
gtgatcggtc tgtcaaaaat taaccgcatt gtgcagttct tgccagcg tccgcaggtg   480 caggaacgtc tgacgcagca aattcttatt gcgctacaaa cgctgctggg caccaataac   540
```

```
gtggctgtct cgatcgacgc ggtgcattac tgcgtgaagg cgcgtggcat ccgcgatgca      600
accagtgcca cgacaacgac ctctcttggt ggattgttca aatccagtca gaatacgcgc      660
cacgagtttc tgcgcgctgt gcgtcatcac aactga                                696

<210> SEQ ID NO 55
<211> LENGTH: 462
<212> TYPE: DNA
<213> ORGANISM: Artificial sequence
<220> FEATURE:
<223> OTHER INFORMATION: Synthetic construct; PTPS cloned on pUC18-PTPS

<400> SEQUENCE: 55
atgaccatga ttacgaattc catgaacatg aacgcggcgg ttggccttcg cgccgcgcg       60 cgattgtcgc gcctcgtgtc cttcagcgcg agccaccggc tgcacagccc atctctgagt     120
gctgaggaga acttgaaagt gtttgggaaa tgcaacaatc cgaatggcca tgggcacaac     180
tataaagttg tggtgacaat tcatggagag atcgatccgg ttacaggaat ggttatgaat     240
ttgactgacc tcaaagaata catggaggag gccattatga agccccttga tcacaagaac     300
ctggatctgg atgtgccata cttttgcagat gttgtaagca cgacagaaaa tgtagctgtc     360
tatatctggg agaacctgca gagacttctt ccagtgggag ctctctataa agtaaaagtg     420
tatgaaactg acaacaacat tgtggtctac aaaggagaat ag                        462

<210> SEQ ID NO 56
<211> LENGTH: 810
<212> TYPE: DNA
<213> ORGANISM: Artificial sequence
<220> FEATURE:
<223> OTHER INFORMATION: Synthetic construct; SPR cloned on pUC19-SPR

<400> SEQUENCE: 56
atgaccatga ttacgccaag cttgggcagg ggcaggctag gttgcgctgt ctgcgtgctg      60
accggggctt cccggggctt cggccgcgcc ctggccccgc agctggccgg gttgctgtcg     120
cccggttcgg tgttgcttct aagcgcacgc agtgactcga tgctgcggca actgaaggag     180
gagctctgta cgcagcagcc gggcctgcaa gtggtgctgg cagccgccga tttgggcacc     240
gagtccggcg tgcaacagtt gctgagcgcg gtgcgcgagc tccctaggcc cgagaggctg     300
cagcgcctcc tgctcatcaa caatgcaggc actcttgggg atgtttccaa aggcttcctg     360
aacatcaatg acctagctga ggtgaacaac tactgggccc tgaacctaac ctccatgctc     420
tgcttgacca ccggcacctt gaatgccttc tccaatagcc ctggcctgag caagactgta     480
gttaacatct catctctgtg tgccctgcag ccttttcaagg gctggggact ctactgtgca     540
gggaaggctg cccgagacat gttataccag gtcctggctg ttgaggaacc cagtgtgagg     600
gtgctgagct atgccccagg tcccctggac accaacatgc agcagttggc ccgggaaacc     660
tccatggacc cagagttgag gagcagactg cagaagttga attctgaggg ggagctggtg     720
gactgtggga cttcagccca gaaactgctg agcttgctgc aaagggacac cttccaatct     780
ggagcccacg tggacttcta tgacatttaa                                      810

<210> SEQ ID NO 57
<211> LENGTH: 594
<212> TYPE: DNA
<213> ORGANISM: Artificial sequence
<220> FEATURE:
<223> OTHER INFORMATION: Synthetic construct; mtrA cloned on
      pUC18(DELTA)ESDmtrA
```

<400> SEQUENCE: 57

```
atgagcaata ttacgaattc catgaaagaa gttaataaag agcaaatcga acaagctgtt      60
cgtcaaattt tagaagcgat cggagaagac ccgaatagag aagggcttct tgatactccg     120
aaaagagtcg caagatgta tgccgaagta ttctccggct tgaatgaaga tccaaaagaa      180
catttccaga ctatcttcgg tgaaaaccat gaggagcttg ttcttgtaaa agatatagcg     240
tttcattcta tgtgtgagca tcaccttgtt ccctttatg gaaaagcaca tgttgcatat     300
atcccgcgag gcggaaaggt cacaggactc agcaaactgg cacgtgccgt gaagccgtt     360 gcaaagcgcc cgcagcttca ggaacgcatc acttctacaa ttgcagaaag catcgtagaa     420
acgcttgatc cgcatggcgt aatggtagtg gttgaagcgg aacacatgtg catgacgatg     480
cgcggtgtaa gaaaaccggg tgcgaaaact gtgacttcag cagtcagagg cgttttaaa    540 gatgatgccg ctgcccgtgc agaagtattg gaacatatta aacgccagga ctaa          594
```

<210> SEQ ID NO 58
<211> LENGTH: 456
<212> TYPE: DNA
<213> ORGANISM: Artificial sequence
<220> FEATURE:
<223> OTHER INFORMATION: Synthetic construct; PTPS cloned on pUC18SDPTPS

<400> SEQUENCE: 58

```
atgagcaata ttacgaattc catgaacgcg gcggttggcc ttcggcgccg cgcgcgattg      60
tcgcgcctcg tgtccttcag cgcgagccac cggctgcaca gcccatctct gagtgctgag     120
gagaacttga agtgtttgg gaaatgcaac aatccgaatg ccatgggca caactataaa      180 gttgtggtga caattcatgg agagatcgat ccggttacga gaatggttat gaatttgact     240
gacctcaaag aatacatgga ggaggccatt atgaagcccc ttgatacaa gaacctggat    300 ctggatgtgc catactttgc agatgttgta agcacgacga aaaatgtagc tgtctatatc     360
tgggagaacc tgcagagact tcttccagtg ggagctctct ataaagtaaa agtgtatgaa     420
actgacaaca cattgtggt ctacaaagga gaatag                                456
```

<210> SEQ ID NO 59
<211> LENGTH: 801
<212> TYPE: DNA
<213> ORGANISM: Artificial sequence
<220> FEATURE:
<223> OTHER INFORMATION: Synthetic construct; SPR cloned on pUC18(DELTA)ESDSPR

<400> SEQUENCE: 59

```
atgagcaata ttacgaattc cggcaggcta ggttgcgctg tctgcgtgct gaccggggct      60
tcccggggct tcggccgcgc cctggccccg cagctggccg ggttgctgtc gcccggttcg     120
gtgttgcttc taagcgcacg cagtgactcg atgctgcggc aactgaagga ggagctctgt     180
acgcagcagc cgggcctgca agtggtgctg gcagccgccg atttgggcac cgagtccggc     240
gtgcaacagt gctgagcgc ggtgcgcgag ctccctaggc ccgagaggct gcagcgcctc     300
ctgctcatca acaatgcagg cactcttggg gatgtttcca aaggcttcct gaacatcaat     360
gacctagctg aggtgaacaa ctactgggcc ctgaacctaa cctccatgct gcttgacc      420 accggcacct tgaatgcctt ctccaatagc cctggcctga gcaagactgt agttaacatc     480
tcatctctgt gtgccctgca gccttcaag ggctggggac tctactgtgc agggaaggct     540
gcccgagaca tgttataccca ggtcctggct gttgaggaac ccagtgtgag ggtgctgagc     600
```

```
tatgccccag gtcccctgga caccaacatg cagcagttgg cccgggaaac ctccatggac    660
ccagagttga ggagcagact gcagaagttg aattctgagg gggagctggt ggactgtggg    720
acttcagccc agaaactgct gagcttgctg caaagggaca ccttccaatc tggagcccac    780
gtggacttct atgacattta a                                              801
```

```
<210> SEQ ID NO 60
<211> LENGTH: 231
<212> TYPE: PRT
<213> ORGANISM: Artificial Sequence
<220> FEATURE:
<223> OTHER INFORMATION: Synthetic construct

<400> SEQUENCE: 60
```

Met Thr Met Ile Thr Asn Ser Met Pro Met Pro Ser Leu Ser Lys Glu
 1               5                  10                  15

Ala Ala Leu Val His Glu Ala Leu Val Ala Arg Gly Leu Glu Thr Pro
            20                  25                  30

Leu Arg Pro Pro Val His Glu Met Asp Asn Glu Thr Arg Lys Ser Leu
        35                  40                  45

Ile Ala Gly His Met Thr Glu Ile Met Gln Leu Leu Asn Leu Asp Leu
    50                  55                  60

Ala Asp Asp Ser Leu Met Glu Thr Pro His Arg Ile Ala Lys Met Tyr
65                  70                  75                  80

Val Asp Glu Ile Phe Ser Gly Leu Asp Tyr Ala Asn Phe Pro Lys Ile
                85                  90                  95

Thr Leu Ile Glu Asn Lys Met Lys Val Asp Glu Met Val Thr Val Arg
            100                 105                 110

Asp Ile Thr Leu Thr Ser Thr Cys Glu His His Phe Val Thr Ile Asp
        115                 120                 125

Gly Lys Ala Thr Val Ala Tyr Ile Pro Lys Asp Ser Val Ile Gly Leu
    130                 135                 140

Ser Lys Ile Asn Arg Ile Val Gln Phe Phe Ala Gln Arg Pro Gln Val
145                 150                 155                 160

Gln Glu Arg Leu Thr Gln Gln Ile Leu Ile Ala Leu Gln Thr Leu Leu
                165                 170                 175

Gly Thr Asn Asn Val Ala Val Ser Ile Asp Ala Val His Tyr Cys Val
            180                 185                 190

Lys Ala Arg Gly Ile Arg Asp Ala Thr Ser Ala Thr Thr Thr Thr Ser
        195                 200                 205

Leu Gly Gly Leu Phe Lys Ser Ser Gln Asn Thr Arg His Glu Phe Leu
    210                 215                 220

Arg Ala Val Arg His His Asn
225                 230

```
<210> SEQ ID NO 61
<211> LENGTH: 153
<212> TYPE: PRT
<213> ORGANISM: Artificial Sequence
<220> FEATURE:
<223> OTHER INFORMATION: Synthetic construct

<400> SEQUENCE: 61
```

Met Thr Met Ile Thr Asn Ser Met Asn Met Asn Ala Ala Val Gly Leu
 1               5                  10                  15

Arg Arg Arg Ala Arg Leu Ser Arg Leu Val Ser Phe Ser Ala Ser His
            20                  25                  30

```
Arg Leu His Ser Pro Ser Leu Ser Ala Glu Glu Asn Leu Lys Val Phe
            35                  40                  45

Gly Lys Cys Asn Asn Pro Asn Gly His Gly His Asn Tyr Lys Val Val
        50                  55                  60

Val Thr Ile His Gly Glu Ile Asp Pro Val Thr Gly Met Val Met Asn
 65              70                  75                  80

Leu Thr Asp Leu Lys Glu Tyr Met Glu Ala Ile Met Lys Pro Leu
                85                  90                  95

Asp His Lys Asn Leu Asp Leu Asp Val Pro Tyr Phe Ala Asp Val Val
            100                 105                 110

Ser Thr Thr Glu Asn Val Ala Val Tyr Ile Trp Glu Asn Leu Gln Arg
            115                 120                 125

Leu Leu Pro Val Gly Ala Leu Tyr Lys Val Lys Val Tyr Glu Thr Asp
            130                 135                 140

Asn Asn Ile Val Val Tyr Lys Gly Glu
145                 150

<210> SEQ ID NO 62
<211> LENGTH: 269
<212> TYPE: PRT
<213> ORGANISM: Artificial Sequence
<220> FEATURE:
<223> OTHER INFORMATION: Synthetic construct

<400> SEQUENCE: 62

Met Thr Met Ile Thr Pro Ser Leu Gly Arg Gly Arg Leu Gly Cys Ala
  1               5                  10                  15

Val Cys Val Leu Thr Gly Ala Ser Arg Gly Phe Gly Arg Ala Leu Ala
                 20                  25                  30

Pro Gln Leu Ala Gly Leu Leu Ser Pro Gly Ser Val Leu Leu Leu Ser
             35                  40                  45

Ala Arg Ser Asp Ser Met Leu Arg Gln Leu Lys Glu Glu Leu Cys Thr
         50                  55                  60

Gln Gln Pro Gly Leu Gln Val Val Leu Ala Ala Asp Leu Gly Thr
 65                  70                  75                  80

Glu Ser Gly Val Gln Gln Leu Leu Ser Ala Val Arg Glu Leu Pro Arg
                 85                  90                  95

Pro Glu Arg Leu Gln Arg Leu Leu Ile Asn Asn Ala Gly Thr Leu
             100                 105                 110

Gly Asp Val Ser Lys Gly Phe Leu Asn Ile Asn Asp Leu Ala Glu Val
             115                 120                 125

Asn Asn Tyr Trp Ala Leu Asn Leu Thr Ser Met Leu Cys Leu Thr Thr
130                 135                 140

Gly Thr Leu Asn Ala Phe Ser Asn Ser Pro Gly Leu Ser Lys Thr Val
145                 150                 155                 160

Val Asn Ile Ser Ser Leu Cys Ala Leu Gln Pro Phe Lys Gly Trp Gly
                 165                 170                 175

Leu Tyr Cys Ala Gly Lys Ala Ala Arg Asp Met Leu Tyr Gln Val Leu
             180                 185                 190

Ala Val Glu Glu Pro Ser Val Arg Val Leu Ser Tyr Ala Pro Gly Pro
             195                 200                 205

Leu Asp Thr Asn Met Gln Gln Leu Ala Arg Glu Thr Ser Met Asp Pro
         210                 215                 220

Glu Leu Arg Ser Arg Leu Gln Lys Leu Asn Ser Glu Gly Glu Leu Val
225                 230                 235                 240
```

Asp Cys Gly Thr Ser Ala Gln Lys Leu Leu Ser Leu Leu Gln Arg Asp
                245                 250                 255

Thr Phe Gln Ser Gly Ala His Val Asp Phe Tyr Asp Ile
            260                 265

<210> SEQ ID NO 63
<211> LENGTH: 197
<212> TYPE: PRT
<213> ORGANISM: Artificial Sequence
<220> FEATURE:
<223> OTHER INFORMATION: Synthetic construct

<400> SEQUENCE: 63

Met Ser Asn Ile Thr Asn Ser Met Gly Gln Val Asn Lys Glu Gln Ile
1               5                   10                  15

Glu Gln Ala Val Arg Gln Ile Leu Glu Ala Ile Gly Glu Asp Pro Asn
                20                  25                  30

Arg Glu Gly Leu Leu Asp Thr Pro Lys Arg Val Ala Lys Met Tyr Ala
            35                  40                  45

Glu Val Phe Ser Gly Leu Asn Glu Asp Pro Lys Glu His Phe Gln Thr
        50                  55                  60

Ile Phe Gly Glu Asn His Glu Glu Leu Val Leu Val Lys Asp Ile Ala
65                  70                  75                  80

Phe His Ser Met Cys Glu His His Leu Val Pro Phe Tyr Gly Lys Ala
                85                  90                  95

His Val Ala Tyr Ile Pro Arg Gly Gly Lys Val Thr Gly Leu Ser Lys
                100                 105                 110

Leu Ala Arg Ala Val Glu Ala Val Ala Lys Arg Pro Gln Leu Gln Glu
            115                 120                 125

Arg Ile Thr Ser Thr Ile Ala Glu Ser Ile Val Glu Thr Leu Asp Pro
        130                 135                 140

His Gly Val Met Val Val Val Glu Ala Glu His Met Cys Met Thr Met
145                 150                 155                 160

Arg Gly Val Arg Lys Pro Gly Ala Lys Thr Val Thr Ser Ala Val Arg
                165                 170                 175

Gly Val Phe Lys Asp Asp Ala Ala Ala Arg Ala Glu Val Leu Glu His
            180                 185                 190

Ile Lys Arg Gln Asp
        195

<210> SEQ ID NO 64
<211> LENGTH: 151
<212> TYPE: PRT
<213> ORGANISM: Artificial Sequence
<220> FEATURE:
<223> OTHER INFORMATION: Synthetic construct

<400> SEQUENCE: 64

Met Ser Asn Ile Thr Gln Ser Met Asn Ala Ala Val Gly Leu Arg Arg
1               5                   10                  15

Arg Ala Arg Leu Ser Arg Leu Val Ser Phe Ser Ala Ser His Arg Leu
                20                  25                  30

His Ser Pro Ser Leu Ser Ala Glu Glu Asn Leu Lys Val Phe Gly Lys
            35                  40                  45

Cys Asn Asn Pro Asn Gly His Gly His Asn Tyr Lys Val Val Val Thr
        50                  55                  60

Ile His Gly Glu Ile Asp Pro Val Thr Gly Met Val Met Asn Leu Thr

```
                    65                  70                  75                  80
Asp Leu Lys Glu Tyr Met Glu Ala Ile Met Lys Pro Leu Asp His
                85                  90                  95

Lys Asn Leu Asp Leu Asp Val Pro Tyr Phe Ala Asp Val Val Ser Thr
                100                 105                 110

Thr Gln Asn Val Ala Val Tyr Ile Trp Glu Asn Leu Gln Arg Leu Leu
                115                 120                 125

Pro Val Gly Ala Leu Tyr Lys Val Lys Val Tyr Glu Thr Asp Asn Asn
            130                 135                 140

Ile Val Val Tyr Lys Gly Glu
145                 150

<210> SEQ ID NO 65
<211> LENGTH: 266
<212> TYPE: PRT
<213> ORGANISM: Artificial Sequence
<220> FEATURE:
<223> OTHER INFORMATION: Synthetic construct

<400> SEQUENCE: 65

Met Ser Asn Ile Thr Asn Ser Gly Arg Leu Gly Cys Ala Val Cys Val
 1               5                  10                  15

Leu Thr Gly Ala Ser Arg Gly Phe Gly Arg Ala Leu Ala Pro Gln Leu
                20                  25                  30

Ala Gly Leu Leu Ser Pro Gly Ser Val Leu Leu Ser Ala Arg Ser
            35                  40                  45

Asp Ser Met Leu Arg Gln Leu Lys Glu Glu Leu Cys Thr Gln Gln Pro
    50                  55                  60

Gly Leu Gln Val Val Leu Ala Ala Asp Leu Gly Thr Glu Ser Gly
65                  70                  75                  80

Val Gln Gln Leu Leu Ser Ala Val Arg Glu Leu Pro Arg Pro Glu Arg
                85                  90                  95

Leu Asn Arg Leu Leu Leu Ile Asn Asn Ala Gly Thr Leu Gly Asp Val
                100                 105                 110

Ser Lys Gly Phe Leu Asn Ile Asn Asp Leu Ala Glu Val Asn Asn Tyr
            115                 120                 125

Trp Ala Leu Asn Leu Thr Ser Met Leu Cys Leu Thr Thr Gly Thr Leu
130                 135                 140

Asn Ala Phe Ser Asn Ser Pro Gly Leu Ser Lys Thr Val Val Asn Ile
145                 150                 155                 160

Ser Ser Leu Cys Ala Leu Gln Pro Phe Lys Gly Trp Gly Leu Tyr Cys
                165                 170                 175

Ala Gly Lys Ala Ala Arg Asp Met Leu Tyr Gln Val Leu Ala Val Glu
            180                 185                 190

Glu Pro Ser Val Arg Val Leu Ser Tyr Ala Pro Gly Pro Leu Asp Thr
        195                 200                 205

Asn Met Gln Gln Leu Ala Arg Glu Thr Ser Met Asp Pro Glu Leu Arg
    210                 215                 220

Ser Arg Leu Gln Lys Leu Asn Ser Glu Gly Glu Leu Val Asp Cys Gly
225                 230                 235                 240

Thr Ser Ala Gln Lys Leu Leu Ser Leu Leu Gln Arg Asp Thr Phe Gln
                245                 250                 255

Ser Gly Ala His Val Asp Phe Tyr Asp Ile
            260                 265
```